(12) United States Patent
Oldenburg et al.

(10) Patent No.: US 7,939,250 B2
(45) Date of Patent: May 10, 2011

(54) VITAMIN K EPOXIDE RECYCLING POLYPEPTIDE VKORC1, A THERAPEUTIC TARGET OF COUMARIN AND THEIR DERIVATIVES

(75) Inventors: Johannes Oldenburg, Königswinter (DE); Clemens R. Müller-Reible, Würzburg (DE); Andreas Fregin, Randersacker (DE); Simone Rost, Würzburg (DE); Tim-Matthias Strom, Munich (DE)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 966 days.

(21) Appl. No.: 10/965,694

(22) Filed: Oct. 14, 2004

(65) Prior Publication Data

US 2005/0271644 A1    Dec. 8, 2005

Related U.S. Application Data

(60) Provisional application No. 60/511,041, filed on Oct. 14, 2003.

(51) Int. Cl.
| | |
|---|---|
| *C12Q 1/68* | (2006.01) |
| *C12N 9/02* | (2006.01) |
| *C12N 15/70* | (2006.01) |
| *C12P 21/06* | (2006.01) |
| *C07H 21/04* | (2006.01) |

(52) U.S. Cl. ........ 435/6; 435/189; 435/69.1; 435/320.1; 536/23.2

(58) Field of Classification Search .............. 435/6, 189, 435/69.1, 320.1; 536/23.2
See application file for complete search history.

(56) References Cited

U.S. PATENT DOCUMENTS

| | | | |
|---|---|---|---|
| 4,736,866 A | 4/1988 | Leder et al. | |
| 4,816,397 A | 3/1989 | Boss et al. | |
| 4,816,567 A | 3/1989 | Cabilly et al. | |
| 5,583,278 A | 12/1996 | Alt et al. | |
| 5,625,122 A | 4/1997 | Mak | |
| 5,698,765 A | 12/1997 | Mak | |
| 5,750,825 A | 5/1998 | Yazaki et al. | |
| 7,482,141 B2 * | 1/2009 | Stafford et al. | 435/69.6 |
| 7,524,665 B2 | 4/2009 | Stafford et al. | |
| 7,645,602 B2 | 1/2010 | Stafford et al. | |
| 7,687,233 B2 | 3/2010 | Stafford et al. | |

FOREIGN PATENT DOCUMENTS

| | | |
|---|---|---|
| DE | 196 25 049 | 1/1998 |
| EP | 0 127 839 B1 | 12/1984 |
| EP | 0 154 133 B1 | 9/1985 |
| EP | 0 368 684 B1 | 5/1990 |
| EP | 0 549 721 B1 | 7/1993 |
| EP | 1 842 920 | 10/2007 |
| WO | WO 88/01649 | 3/1988 |
| WO | 90/03496 | 4/1990 |
| WO | 91/01372 | 2/1991 |
| WO | 92/01795 | 2/1992 |
| WO | 92/19636 | 11/1992 |
| WO | WO 93/06213 | 4/1993 |
| WO | WO 98/24884 | 6/1998 |
| WO | WO 99/43003 | 8/1999 |
| WO | WO 00/03015 A | 1/2000 |
| WO | 02/29045 | 4/2002 |
| WO | WO-2005/030039 A2 * | 4/2005 |
| WO | 2005/040367 | 5/2005 |
| WO | 2006/089613 | 8/2006 |
| WO | 2006/101474 | 9/2006 |
| WO | 2007/065173 | 6/2007 |
| WO | 2007/075976 | 7/2007 |

OTHER PUBLICATIONS

Benvenuti et al. Crystallization of soluble proteins in vapor diffusion for x-ray crystallography. Nat Protoc. 2007;2(7):1633-51.*
Scott et al. Warfarin pharmacogenetics: CYP2C9 and VKORC1 genotypes predict different sensitivity and resistance frequencies in the Ashkenazi and Sephardi Jewish populations, Am J Hum Genet 2008, 82(2):495-500.*
Altschul et al., 1997, Nucleic Acids Res., 25: 3389-3402.
Bandyopadhyay, P. K. et al., (2002). gamma -Glutamyl carboxylation: An extracellular posttranslational modification that antedates the divergence of molluscs, arthropods, and chordates, Proc Natl Acad Sci U S A 99, 1264-1269.
Boneh, A. et al. (1996). Hereditary deficiency of vitamin K-dependent coagulation factors with skeletal abnormalities, Am J Med Genet 65, 241-243.
Brenner, B. et al. (1998). A missense mutation in gamma-glutamyl carboxylase gene causes combined deficiency of all vitamin K-dependent blood coagulation factors, Blood 92, 4554-4559.
Cain, D. et al. (1997). Assembly of the warfarin-sensitive vitamin K 2,3-epoxide reductase enzyme complex in the endoplasmic reticulum membrane, J Biol Chem 272, 29068-29075.
Chen, C. A. et al. (1988). Calcium phosphate-mediated transfer: a highly efficient transfection system for stably transforming cells with plasmid DNA. Biotechniques 6, 632-638.
Database EMBL 'Online! Last update Sep. 22, 2003 Feb. 8, 2001, "Mus musculus 13 days embryo head cDNA, RIKEN full-length enriched library, clone: 3110005B16 product: hypothetical protein, full insert sequence." XP002318821.

(Continued)

*Primary Examiner* — Robert B Mondesi
*Assistant Examiner* — Iqbal H Chowdhury
(74) *Attorney, Agent, or Firm* — McAndrews Held & Malloy Ltd.

(57) ABSTRACT

The invention relates to a novel polypeptide vitamin K epoxide recycling polypeptide (VKORC1) as a target for coumarin and its derivatives. The invention further provides methods for identifying coumarin derivatives, and also claims VKORC1 polypeptides and VKORC1 nucleic acids containing a sequence abnormality associated with a VKORC1 associated deficiency such as warfarin resistance, wherein the VKORC1 polypeptides and VKORC1 nucleic acids can be used for diagnosing these deficiencies. Moreover, the invention relates to methods for identifying coumarin derivatives usable in pest control of rodents.

4 Claims, 19 Drawing Sheets

OTHER PUBLICATIONS

Database Genpept 'Online! NCBI; Aug. 25, 2004, Rost et al.: "vitamin K epoxide reductase complex, subunit 1; vitamin K1 epoxide reductase (warfarin-sensitive); phylloquinone epoxide reductase" XP002318820.

Database UniProt 'Online! Jun. 1, 2001, "Mus musculus 13 days embryo head cDNA, RIKEN full-length enriched library, clone:3110005B16 product:hypothetical protein, full insert sequence (Vitamin K epoxide reductase complex, subunit 1) (Mus musculus adult male kidney cDNA, RIKEN full-length enriched library, clone:0610033K05 product:hypotheti" XP002318822.

Dockal, M. et al. (1999). The three recombinant domains of human serum albumin. Structural characterization and ligand binding properties, J Biol Chem 274, 29303-29310.

Dockal, M. et al. (2000). Five recombinant fragments of human serum albumin-tools for the characterization of the warfarin binding site, Protein Sci 9, 1455-1465.

Doetschman. Gene Transfer in Embryonic Stem Cells, p. 115 to 146 in Pinkert, 1994.

Ekelund, H. et al. (1986). Combined deficiency of coagulation factors II, VII, IX, and X: a case of probable congenital origin, Pediatr Hematol Oncol 3, 187-193.

Esmon, C. T. et al. (1975). The functional significance of vitamin K action. Difference in phospholipid binding between normal and abnormal prothrombin, J Biol Chem 250, 4095-4099.

Fasco, M. J. et al. (1983). Warfarin inhibition of vitamin K 2,3-epoxide reductase in rat liver microsomes, Biochemistry 22, 5655-5660.

Fasco, M. J. et al. (1983b). Formation of hydroxyvitamin K by vitamin K epoxide reductase of warfarin-resistant rats. J Biol Chem 258, 4372-4380.

Fischer, M. et al. (1966). Kongenitaler Mangel der Falctoren II, VIII and X, Zeitschrift für Kinderheilkunde 95, 309-323.

Fregin, A. et al. (2002). Homozygosity mapping of a second gene locus for hereditary combined deficiency of vitamin K-dependent clotting factors to the centromeric region of chromosome 16, Blood 100, 3229-3232.

Furie, B. et al. (1988). The molecular basis of blood coagulation, Cell 53, 505-518.

Goldsmith, G. H., Jr. et al. (1982). Studies on a family with combined functional deficiencies of vitamin K-dependent coagulation factors, J Clin Invest 69, 1253-1260.

Gossen M. et al. (1994) Curr. Opin. Biotechnol. 5, 516-20.

Greavses, J. H. et al. (1967). Heritable resistance to warfarin in rats, Nature 215, 877-878.

Guenthner, T. M. et al. (1998). Co-purification of microsomal epoxide hydrolase with the warfarin- sensitive vitamin K1 oxide reductase of the vitamin K cycle, Biochem Pharmacol 55, 169-175.

Harlow & Lane, 1988, Using Antibodies: A Laboratory Manual, Cold Spring Harbor Press, New York, USA, Chapter 5, pp. 53-135.

Jackson, M. R. et al. (1990). Identification of a consensus motif for retention of transmembrane proteins in the endoplasmic reticulum, Embo J 9, 3153-3162.

Jackson, W. B. et al. (1988). Overview of anticoagulant rodenticide usage and resistance. In Current advances in vitamin K research, J. W. Suttie, ed. (New York, Elsevier), pp. 381-397.

Johnson, C. A. et al. (1980). Characterization of a variant prothrombin in a patient congenitally deficient in factors II, VII, IX and X, Br J Haematol 44, 461-469.

Kohn, M. H. et al. (1999). Genomic assignment of the warfarin resistance locus, Rw, in the rat, Mamm Genome 10, 696-698.

Kozak, 1987, Nucleic. Acids Res. 15: 8125-48.

Lee et al. (1981) Nature 214, 228-232.

Leonard, C. O. (1988). Vitamin K responsive bleeding disorder: a genocopy of the warfarin embryopathy, Proceedings of the Greenwood Genetic Center 7, 165-166.

Li, Tao et al.: "Identification of the gene for vitamin K epoxide reductase." Nature. Feb. 5, 2004, vol. 427, No. 6974, Feb. 5, 2004, pp. 541-544, XP002318817.

Manfioletti, G. et al. (1993). The protein encoded by a growth arrest-specific gene (gas6) is a new member of the vitamin K-dependent proteins related to protein S, a negative coregulator in the blood coagulation cascade, Mol Cell Biol 13, 4976-4985.

Martin, A. D. et al. Warfarin-resistance genotype determination in the Norway rat, Rattus norvegicus. Laboratory Animals, 209-214 (1979).

McManus et al. 2002, Nature Reviews 3: 737-747, Gene Silencing in Mammals by small interfering RNAs.

McMillan, C. W. et al. (1966). Congenital combined deficiency of coagulation factors II, VII, IX and X. Report of a case, N Engl J Med 274, 1313-1315.

Mutero, A. et al. (1994). Resistance-associated point mutations in insecticide-insensitive acetylcholinesterase, Proc Natl Acad Sci USA 91, 5922-5926.

Monastersky, Gene Transfer Technology; Alternative Techniques and Applications, p. 177 to 220 in Pinkert, 1994, supra.

Mumberg et al. (1994) Nucl. Acids Res., 22, 5767 5768.

Nellen and Lichtenstein, 1993, Trends Biochem. Sci. 18: 419-23.

Stein, 1992, Leukemia 6: 967-74.

Oldenburg, J. et al. (2000). Congenital deficiency of vitamin K dependent coagulation factors in two families presents as a genetic defect of the vitamin K-epoxide-reductase-complex, Thromb Haemost 84, 937-941.

O'Reilly, R. A. (1970). The second reported kindred with hereditary resistance to oral anticoagulant drugs, N Engl J Med 282, 1448-1451.

O'Reilly, R. A. et al. (1964). Hereditary transmission of exceptional resistance to coumarin anticoagulant drugs: the first reported kindred, N Engl J Med 271, 809-815.

Pauli, R. M. et al. (1987). Association of congenital deficiency of multiple vitamin K-dependent coagulation factors and the phenotype of the warfarin embryopathy: clues to the mechanism of teratogenicity of coumarin derivatives, Am J Hum Genet 41, 566-583.

Pechlaner, C. et al. (1992). A new case of combined deficiency of vitamin K dependent coagulation factors, Thromb Haemost 68, 617.

Petersen, C. E. et al. (2002). Probing the structure of the warfarin-binding site on human serum albumin using site-directed mutagenesis, Proteins 47, 116-125.

Prentice, C. R. (1985). Acquired coagulation disorders, Clin Haematol 14, 413-442.

Presnell, S. R. et al. (2002). The vitamin K-dependent carboxylase, Thromb Haemost 87, 937-946.

Polites and Pinkert, DNA Microinjection and Transgenic Animal Production, p. 15 to 68 in Pinkert, 1994, Transgenic animal technology: a laboratory handbook, Academic Press, London, UK.

Price, P. A. (1988). Role of vitamin-K-dependent proteins in bone metabolism, Annu Rev Nutr 8, 565-583.

Rost, Simone, et al.: "Mutations in VKORC1 cause warfarin resistance and multiple coagulation factor deficiency type 2." Nature. Feb. 5, 2004, vol. 427, No. 6974, Feb. 5, 2004, pp. 537-541, XP002318816.

Rusconi, C.P., et al. (2002). RNA aptamers as reversible antagonists of coagulation factor 1Xa. Nature Sep. 5, 2002; 419 (6902): 90-4.

Russel et al. (1983), J. Biol. Chem. 258, 2674-2682.

Sperling, R. et al. (1978). Metal binding properties of gamma-carboxyglutamic acid. Implications for the vitamin K-dependent blood coagulation proteins, J Biol Chem 253, 3898-3906.

Spronk, H. M. et al. (2000). Novel mutation in the gamma-glutamyl carboxylase gene resulting in congenital combined deficiency of all vitamin K-dependent blood coagulation factors, Blood 96, 3650-3652.

Stitt, T. N. et al. (1995). The anticoagulation factor protein S and its relative, Gas6, are ligands for the Tyro 3/Ax1 family of receptor tyrosine kinases, Cell 80, 661-670.

Suttie, J. W. (1987). The biochemical basis of warfarin therapy, Adv Exp Med Biol 214, 3-16.

Thijssen, H. H. & Pelz, H. J. in Advances in vertebrate pest management (eds. Pelz, H. J., Cowan, D. P. & Feare, C. J.) 181-192 (Filander-Verlag, Fürth, 2001).

Uhlmann, E. & Peyman, A. (1990) Chemical Reviews, 90, 543-584, No. 4.

Vicente, V. et al. (1984). Congenital deficiency of vitamin K-dependent coagulation factors and protein C, Thromb Haemost 51, 343-346.

Wallace, M. E. et al. (1976). A major gene controlling warfarin-resistance in the house mouse, J Hyg (Lond) 76, 173-181.

Wallin, R. et al. (1985). Vitamin K-dependent carboxylation and vitamin K metabolism in liver. Effects of warfarin, J Clin Invest 76, 1879-1884.

Winter and Milstein, 1991, Nature 349:293-299.

Wood, Retrovirus-Mediated Gene Transfer, p. 147 to 176 in Pinkert, 1994, supra.

Zheng and Kemeny, 1995, Clin. Exp. Immunol. 100: 380-2.

Zimmerman, A., et al.: "Biochemical basis of hereditary resistance to warfarin in the rat" Biochemical Pharmacology 1974, vol. 23, No. 6, 1974, pp. 1033-1040, XP002318819.

* cited by examiner

| siRNA sequences for Homo sapiens VKORC1 and primers to express them using for example the siLentGene™ U6 Cassette RNA Interference System. ||||
|---|---|---|---|
| Terminator sequence (underlined) Target sequence (bold) U6 cassette matching (*italics*) ||||
| Sequence of siRNA | Generate scrambled versions of the siRNA to use as controls | Position on sequence entered | Percent GC |
| GGUUGCAUCUUCUACACACUU (SEQ ID NO:29)<br>19 bases<br>UUCCAACGUAGAAGAUGUGUG (SEQ ID NO:30) | | 249-268 | 47% GC |
| Downstream Primer A: 5'<u>CAAAAACTGTAAAAA</u> GGTTGCATCTTCTACACAC *GGTGTTTCGTCCTTTCCACAAGA* 3' (SEQ ID NO:31)<br>Downstream Primer B: 5'<u>CAAAAACTGTAAAAA</u> GTGTGTAGAAGATGCAACC *GGTGTTTCGTCCTTTCCACAAGA* 3'(SEQ ID NO:32) ||||
| GUCUCUCGCUGGUUCUGUCUU (SEQ ID NO:33)<br>19 bases<br>UUCAGAGAGCGACCAAGACAG (SEQ ID NO:34) | | 335-354 | 58% GC |
| Downstream Primer A: 5'<u>CAAAAACTGTAAAAA</u> GTCTCTCGCTGGTTCTGTC *GGTGTTTCGTCCTTTCCACAAGA* 3' (SEQ ID NO:35)<br>Downstream Primer B: 5'<u>CAAAAACTGTAAAAA</u> GACAGAACCAGCGAGAGAC *GGTGTTTCGTCCTTTCCACAAGA* 3' (SEQ ID NO:36) ||||
| GGCCUGGAUCCUGUUCUUCUU (SEQ ID NO:37)<br>19 bases<br>UUCCGGACCUAGGACAAGAAG (SEQ ID NO:38) | | 359-378 | 58% GC |
| Downstream Primer A: 5'<u>CAAAAACTGTAAAAA</u> GGCCTGGATCCTGTTCTTC *GGTGTTTCGTCCTTTCCACAAGA* 3' (SEQ ID NO:39)<br>Downstream Primer B: 5'<u>CAAAAACTGTAAAAA</u> GAAGAACAGGATCCAGGCC *GGTGTTTCGTCCTTTCCACAAGA* 3' (SEQ ID NO:40) ||||
| GAUCCUGUUCUUCGUGCUCUU (SEQ ID NO:41)<br>19 bases<br>UUCUAGGACAAGAAGCACGAG (SEQ ID NO:42) | | 365-384 | 53% GC |
| Downstream Primer A: 5'<u>CAAAAACTGTAAAAA</u> GATCCTGTTCTTCGTGCTC ||||

FIGURE 6B

| | | | |
|---|---|---|---|
| GGTGTTTCGTCCTTTCCACAAGA 3' (SEQ ID NO:43) | | | |
| Downstream Primer B: 5'CAAAAACTGTAAAAA GAGCACGAAGAACAGGATC GGTGTTTCGTCCTTTCCACAAGA 3' (SEQ ID NO:44) | | | |
| GCAUUGUUUGUAUCACCACUU (SEQ ID NO:45)<br>                    19 bases<br>UUCGUAACAAACAUAGUGGUG (SEQ ID NO:46) | | 394-413 | 42% GC |
| Downstream Primer A: 5'CAAAAACTGTAAAAA GCATTGTTTGTATCACCAC GGTGTTTCGTCCTTTCCACAAGA 3' (SEQ ID NO:47)<br>Downstream Primer B: 5'CAAAAACTGTAAAAA GTGGTGATACAAACAATGC GGTGTTTCGTCCTTTCCACAAGA 3' (SEQ ID NO:48) | | | |
| GCUCAGUUUCCGGAAGGUCUU (SEQ ID NO:49)<br>                    19 bases<br>UUCGAGUCAAAGGCCUUCCAG (SEQ ID NO:50) | | 440-459 | 58% GC |
| Downstream Primer A: 5'CAAAAACTGTAAAAA GCTCAGTTTCCGGAAGGTC GGTGTTTCGTCCTTTCCACAAGA 3' (SEQ ID NO:51)<br>Downstream Primer B: 5'CAAAAACTGTAAAAA GACCTTCCGGAAACTGAGC GGTGTTTCGTCCTTTCCACAAGA 3' (SEQ ID NO:52) | | | |

Figure 7

Locations of siRNA targets in the coding sequence of
Homo sapiens vitamin K epoxide reductase complex subunit 1 (Hs_VKORC1)

```
  1  ATGGGCAGCA  CCTGGGGGAG  CCTGGCTCGG  GTGCGGCTCG  CTCTTTGCCT  GACGGGCTTA
 61  GTGCTCTCGC  TCTACGCGCT  GCACGTGAAG  GCGGCGCGCG  CCCGGACCG   GGATTACCGC
121  GCGCTCTGCG  ACGTGGGCAC  CGCCATCAGC  CGTTCGGCG   TCTTCTCCTC  CAGGTGGGGC
181  AGGGGTTTCG  GGCTGGTGGA  GCATGTGCTG  GGACAGGACA  GCATCCTCAA  TCAATCCAAC
241  AGCATATTCG  GTGCTCTCTA CTACACA TA  CAGCTATTGT  TAGGTTGCCT  GCGGACACGC
301  TGGGCCCTCTG  TCCTGATGCT  GCTGAGCTCC  CTGGTTGTC TGGTC TTG TAC TTG
361  CCTGC TGTGC  GCTCTATGAT  TTCTCATTC TTGTA TC  CTATGCT
421  ATCAACGTGA  GCCTGATGTG                        AAGAACCCCA  GGGCAAGCT
481  AAGAGGCACT  GA
```

Figure 8

Primer sequences and PCR conditions for Homo sapiens VKORC1 and Homo sapiens VKORC1L1

| SEQ ID No: | Primer | Sequence | Annealing temperature |
|---|---|---|---|
| 55 | Hs_VKORC1-Ex1-F | CAATTCCGAGTCAGAG | 58°C |
| 56 | Hs_VKORC1-Ex1-R | TAATCATCGGCTCCGGC | |
| 57 | Hs_VKORC1-Ex2-F | CAAGGCACTGGGTTGACAG | 58°C |
| 58 | Hs_VKORC1-Ex2-R | GAGTGGGGCTGAGCTGAC | |
| 59 | Hs_VKORC1-Ex3-F | CACATCATGCAGTCTTCCC | 58°C |
| 60 | Hs_VKORC1-Ex4-R | CTTAGCAGCGGTCACATCC | |
| 61 | Hs_VKORC1-cDNA-F | GGCACGAGGGTTTTCTCC | 55°C |
| 62 | Hs_VKORC1-cDNA-R | CTCACATGCAAAGCAAAG | |
| 63 | Rn_VKORC1-cDNA-F | GGCGGTTGTTCCCTCTT | 55°C |
| 64 | Rn_VKORC1-cDNA-R | CATGTGCTAACCGAAGGAA | |
| 65 | Rn_VKORC1-cDNA-F-nes | TTGTGTCTGCGCTGTACTGTC | 60°C |
| 66 | Rn_VKORC1-cDNA-R-nes | GTCAGCCTGGCATGAGGT | |
| 67 | Fr_VKORC1-cDNA-F | TCTTTCAGTCCATGGTCCTC | 55°C |
| 68 | Fr_VKORC1-cDNA-R | TCAGTTAGTCCGACCTCCTG | |
| 69 | Fr_VKORC1-cDNA-F-nes | GTGGCCATCTGAGCAGAAAC | 60°C |
| 70 | Fr_VKORC1-cDNA-R-nes | TGCTGGATTTCAGTGGGAAC | |
| 71 | Hs_VKORC1L1-cDNA-F | TGCCTGGCCTCCGACCC | 55°C |
| 72 | Hs_VKORC1L1-cDNA-R | GTTAAATCCATCGGCTAAAAAC | |
| 73 | Hs_VKORC1L1-cDNA-F-nes | GGCGGCTGAGGTGGAG | 60°C |
| 74 | Hs_VKORC1L1-cDNA-R-nes | AGCAATGGTTGCTCACTTAC | |
| 75 | Fr_VKORC1L1-cDNA-F | CGACTCCTGCGCTATGTAC | 55°C |
| 76 | Fr_VKORC1L1-cDNA-R | CATGTTGTTGTTTGTTATTTGAT TT | |
| 77 | Fr_VKORC1L1-cDNA-F-nes | CGTATGTATGCGTGTCTCCAG | 60°C |
| 78 | Fr_VKORC1L1-cDNA-Rnes | TTTTCACGGCCGTTCTGA | |
| 79 | Rn_VKORC1L1-cDNA-F | TGCTGCCTCGAGCGGAG | 60°C |
| 80 | Rn_VKORC1L1-cDNA-R | ACAGGTTAAATGATGGC | |
| 81 | Rn_VKORC1L1-cDNA-F-nes | CTGAGTGGAGGCGGAGG | 60°C |
| 82 | Rn_VKORC1L1-cDNA-R-nes | TTTCATGTTCATGATCACATTTTG | |
| 83 | Rn_VKORC1L1-cDNA-R-short | CTGGCTGTCATGCCAAGTAA | |
| 84 | Mm_VKORC1L1-cDNA-F | GGAACATGCCCCCCCG | 58°C |
| 85 | Mm_VKORC1L1-cDNA-R | TCTTGTCTAAGAGTGGACC | |
| 86 | Mm_VKORC1L1-cDNA-F-nes | GGTATGCAGTGTGCGCC | 58°C |
| 87 | Mm_VKORC1L1-cDNA-R-nes | GCATTTCCCAAGATGTTCTG | |

Hs, Homo sapiens; Rn, rattus norvegicus; Fr, fugu rubripes; Mm, mus musculus; nes, primer for nested PCR

FIGURE 9A

| TABLE OF SEQUENCES | | |
|---|---|---|
| SEQ ID No: | Name | Species |
| 1 | protein sequence of vitamin K epoxide reductase complex subunit 1 (Hs_VKORC1) | Homo sapiens |
| 2 | coding sequence of Homo sapiens vitamin K epoxide reductase complex subunit 1 Hs_VKORC1 | Homo sapiens |
| 3 | vitamin K-dependent clotting factor type 2 (VKCFD2)-mutation (292C>T; R98W) of the Hs_VKORC1 sequence | Homo sapiens |
| 4 | Warfarin resistance (WR)-mutation sequence 1 (85G>T; V29L) of the Hs_VKORC1 sequence | Homo sapiens |
| 5 | Warfarin resistance (WR)-mutation sequence 2 (134T>C; V45A) of the Hs_VKORC1 sequence | Homo sapiens |
| 6 | Warfarin resistance (WR)-mutation sequence 3 (172A>G; R58G) of the Hs_VKORC1 sequence | Homo sapiens |
| 7 | Warfarin resistance (WR)-mutation sequence 4 (383T>G; L128R) of the Hs_VKORC1 sequence | Homo sapiens |
| 8 | Single nucleotide polymorphism (SNP) 1 (129C>T, C43C) of the Homo sapiens vitamin K epoxide reductase complex subunit 1 (Hs_VKORC1) sequence | Homo sapiens |
| 9 | SNP 2 (358C>T, L120L) of the Homo sapiens vitamin K epoxide reductase complex subunit 1 (Hs_VKORC1) sequence | Homo sapiens |
| 10 | protein sequence of Homo sapiens VKORC1 like protein 1 (Hs_VKORC1L1) | Homo sapiens |
| 11 | coding sequence of Homo sapiens VKORC1 like protein 1 (Hs_VKORC1L1) | Homo sapiens |
| 12 | protein sequence of Rattus norvegicus vitamin K epoxide reductase complex subunit 1 (Rn_VKORC1) | Rattus norvegicus |
| 13 | coding sequence of Rattus norvegicus vitamin K epoxide reductase complex subunit 1 (Rn_VKORC1) | Rattus norvegicus |
| 14 | Rat warfarin resistance (Rw)-mutation sequence (416A>G; Y139C) of the Rn_VKORC1 sequence | Rattus norvegicus |
| 15 | protein sequence of Rattus norvegicus VKORC1 like protein 1 (Rn_VKORC1L1) | Rattus norvegicus |
| 16 | coding sequence of Rattus norvegicus VKORC1 like protein 1 | Rattus norvegicus |

FIGURE 9B

| | | |
|---|---|---|
| | (Rn_VKORC1L1) | |
| 17 | protein sequence of Mus musculus vitamin K epoxide reductase complex subunit 1 (Mm_VKORC1) | Mus musculus |
| 18 | coding sequence of Mus musculus vitamin K epoxide reductase complex subunit 1 (Mm_VKORC1) | Mus musculus |
| 19 | protein sequence of Mus musculus VKORC1 like protein 1 (Mm_VKORC1L1) | Mus musculus |
| 20 | coding sequence of Mus musculus VKORC1 like protein 1 (Mm_VKORC1L1) | Mus musculus |
| 21 | protein sequence of Fugu rubripes vitamin K epoxide reductase complex subunit 1 (Fr_VKORC1) | Fugu rubripes |
| 22 | coding sequence of Fugu rubripes vitamin K epoxide reductase complex subunit 1 (Fr_VKORC1) | Fugu rubripes |
| 23 | protein sequence of Fugu rubripes VKORC1 like protein 1 (Fr_VKORC1L1) | Fugu rubripes |
| 24 | coding sequence of Fugu rubripes VKORC1 like protein 1 (Fr_VKORC1L1) | Fugu rubripes |
| 25 | protein sequence of Xenopus laevis vitamin K epoxide reductase complex subunit 1 (Xl_VKORC1) | Xenopus laevis |
| 26 | coding sequence of Xenopus laevis vitamin K epoxide reductase complex subunit 1 (Xl_VKORC1) | Xenopus laevis |
| 27 | protein sequence of Anopheles gambiae vitamin K epoxide reductase complex subunit 1 (Ag_VKORC1) | Anopheles gambiae |
| 28 | coding sequence of Anopheles gambiae vitamin K epoxide reductase complex subunit 1 (Ag_VKORC1) | Anopheles gambiae |
| 29 | siRNA sequence 1 Homo sapiens vitamin K epoxide reductase complex subunit 1 (Hs_VKORC1) | |
| 30 | siRNA sequence 2 of Homo sapiens vitamin K epoxide reductase complex subunit 1 (Hs_VKORC1) | |
| 31 | Downstream primer 1 for Homo sapiens vitamin K epoxide reductase complex subunit 1 (Hs_VKORC1) siRNA sequence | |
| 32 | Downstream primer 2 for Homo sapiens vitamin K epoxide reductase complex subunit 1 (Hs_VKORC1) siRNA sequence | |
| 33 | siRNA sequence 3 Homo sapiens vitamin K epoxide reductase complex subunit 1 (Hs_VKORC1) | |
| 34 | siRNA sequence 4 Homo sapiens | |

FIGURE 9C

| | | |
|---|---|---|
| | vitamin K epoxide reductase complex subunit 1 (Hs_VKORC1) | |
| 35 | Downstream primer 3 for Homo sapiens vitamin K epoxide reductase complex subunit 1 (Hs_VKORC1) siRNA sequence | |
| 36 | Downstream primer 4 for Homo sapiens vitamin K epoxide reductase complex subunit 1 (Hs_VKORC1) siRNA sequence | |
| 37 | siRNA sequence 5 Homo sapiens vitamin K epoxide reductase complex subunit 1 (Hs_VKORC1) | |
| 38 | siRNA sequence 6 Homo sapiens vitamin K epoxide reductase complex subunit 1 (Hs_VKORC1) | |
| 39 | Downstream primer 5 for Homo sapiens vitamin K epoxide reductase complex subunit 1 (Hs_VKORC1) siRNA sequence | |
| 40 | Downstream primer 6 for Homo sapiens vitamin K epoxide reductase complex subunit 1 (Hs_VKORC1) siRNA sequence | |
| 41 | siRNA sequence 7 Homo sapiens vitamin K epoxide reductase complex subunit 1 (Hs_VKORC1) | |
| 42 | siRNA sequence 8 Homo sapiens vitamin K epoxide reductase complex subunit 1 (Hs_VKORC1) | |
| 43 | Downstream primer 7 for Homo sapiens vitamin K epoxide reductase complex subunit 1 (Hs_VKORC1) siRNA sequence | |
| 44 | Downstream primer 8 for Homo sapiens vitamin K epoxide reductase complex subunit 1 (Hs_VKORC1) siRNA sequence | |
| 45 | siRNA sequence 9 Homo sapiens vitamin K epoxide reductase complex subunit 1 (Hs_VKORC1) | |
| 46 | siRNA sequence 10 Homo sapiens vitamin K epoxide reductase complex subunit 1 (Hs_VKORC1) | |
| 47 | Downstream primer 9 for Homo sapiens vitamin K epoxide reductase complex subunit 1 (Hs_VKORC1) siRNA sequence | |
| 48 | Downstream primer 10 for Homo sapiens vitamin K epoxide reductase complex subunit 1 (Hs_VKORC1) siRNA sequence | |
| 49 | siRNA sequence 11 Homo sapiens vitamin K epoxide reductase complex subunit 1 (Hs_VKORC1) | |

FIGURE 9D

| 50 | siRNA sequence 12 Homo sapiens vitamin K epoxide reductase complex subunit 1 (Hs_VKORC1) | |
|---|---|---|
| 51 | Downstream primer 11 for Homo sapiens vitamin K epoxide reductase complex subunit 1 (Hs_VKORC1) siRNA sequence | |
| 52 | Downstream primer 12 for Homo sapiens vitamin K epoxide reductase complex subunit 1 (Hs_VKORC1) siRNA sequence | |
| 53 | PCR primer for amplification of the complete coding sequence of Homo sapiens vitamin K epoxide reductase complex subunit 1 (VKORC1-HindIII-F) | |
| 54 | PCR primer for amplification of the complete coding sequence of Homo sapiens vitamin K epoxide reductase complex subunit 1 (VKORC1-HindIII-F) | |
| 55 | PCR primer for amplification of the Homo sapiens Hs_VKORC1-Ex1-F sequence | |
| 56 | PCR primer for amplification of the Homo sapiens Hs_VKORC1-Ex1-R sequence | |
| 57 | PCR primer for amplification of the Homo sapiens Hs_VKORC1-Ex2-F sequence | |
| 58 | PCR primer for amplification of the Homo sapiens Hs_VKORC1-Ex2-R sequence | |
| 59 | PCR primer for amplification of the Homo sapiens Hs_VKORC1-Ex3-F sequence | |
| 60 | PCR primer for amplification of the Homo sapiens Hs_VKORC1-Ex3-R sequence | |
| 61 | PCR primer for amplification of the Homo sapiens Hs_VKORC1-cDNA-F sequence | |
| 62 | PCR primer for amplification of the Homo sapiens Hs_VKORC1-cDNA-R sequence | |
| 63 | PCR primer for amplification of the Rattus norvegicus Rn_VKORC1-cDNA-F sequence | |
| 64 | PCR primer for amplification of the Rattus norvegicus Rn_VKORC1-cDNA-R sequence | |
| 65 | PCR primer for amplification of the Rattus norvegicus Rn_VKORC1-cDNA-F-nes sequence | |
| 66 | PCR primer for amplification of the Rattus norvegicus Rn_VKORC1-cDNA-R-nes sequence | |

FIGURE 9E

| | | |
|---|---|---|
| 67 | PCR primer for amplification of the Fugu rubripes Fr_VKORC1-cDNA-F sequence | |
| 68 | PCR primer for amplification of the Fugu rubripes Fr_VKORC1-cDNA-R sequence | |
| 69 | PCR primer for amplification of the Fugu rubripes Fr_VKORC1-cDNA-F-nes sequence | |
| 70 | PCR primer for amplification of the Fugu rubripes Fr_VKORC1-cDNA-R-nes sequence | |
| 71 | PCR primer for amplification of the Homo sapiens Hs_VKORC1L1-cDNA-F sequence | |
| 72 | PCR primer for amplification of the Homo sapiens Hs_VKORC1L1-cDNA-R sequence | |
| 73 | PCR primer for amplification of the Homo sapiens Hs_VKORC1L1-cDNA-F-nes sequence | |
| 74 | PCR primer for amplification of the Homo sapiens Hs_VKORC1L1-cDNA-R-nes sequence | |
| 75 | PCR primer for amplification of the Fugu rubripes Fr_VKORC1L1-cDNA-F sequence | |
| 76 | PCR primer for amplification of the Fugu rubripes Fr_VKORC1L1-cDNA-R sequence | |
| 77 | PCR primer for amplification of the Fugu rubripes Fr_VKORC1L1-cDNA-F-nes sequence | |
| 78 | PCR primer for amplification of the Fugu rubripes Fr_VKORC1L1-cDNA-Rnes sequence | |
| 79 | PCR primer for PCR primer for Rattus norvegicus Rn_VKORC1L1-cDNA-F sequence | |
| 80 | PCR primer for amplification of the Rattus norvegicus Rn_VKORC1L1-cDNA-R sequence | |
| 81 | PCR primer for amplification of the Rattus norvegicus Rn_VKORC1L1-cDNA-F-nes sequence | |
| 82 | PCR primer for amplification of the Rattus norvegicus Rn_VKORC1L1-cDNA-R-nes sequence | |
| 83 | PCR primer for amplification of the Rattus norvegicus Rn_VKORC1L1-cDNA-R-short sequence | |
| 84 | PCR primer for amplification of the Mus musculus Mm_VKORC1L1-cDNA-F sequence | |
| 85 | PCR primer for amplification of the | |

FIGURE 9F

|  | Mus musculus Mm_VKORC1L1-cDNA-R sequence |  |
|---|---|---|
| 86 | PCR primer for amplification of the Mus musculus Mm_VKORC1L1-cDNA-F-nes sequence |  |
| 87 | PCR primer for amplification of the Mus musculus Mm_VKORC1L1-cDNA-R-nes sequence |  |
| 88 | rVKORC1-outerF PCR Primer |  |
| 89 | rVKORC1-outerR PCR Primer |  |
| 90 | rVKORC1-innerF PCR Primer |  |
| 91 | rVKORC1-innerR PCR Primer |  |
| 92 | VKORC1-pcdna3-F PCR Primer |  |
| 93 | VKORC1-pcdna3-R PCR Primer |  |
| 94 | Homo sapiens VKORC1 with rat warfarin resistance mutation 416A>G |  |

Figure 10

VKOR activities[1] of HEK293 cells transfected with VKORC1 cDNA constructs

| | | Warfarin [µM] | | | | | |
|---|---|---|---|---|---|---|---|
| Mutation | Phenotype | 0 | 5 | 10 | 20 | 40 | 80 |
| WT | normal | 20.29 | 8.66 | 6.39 | 4.33 | 2.71 | 0.88 |
| R98W | VKCFD2 | 1.81 | 0.73 | 0.42 | 0.16 | <0.10 | <0.10 |
| V29L | WR | 19.59 | 6.34 | 5.08 | 5.26 | 4.69 | 2.19 |
| V45A | WR | 4.67 | 1.12 | 1.14 | 0.57 | <0.10 | <0.10 |
| R58G | WR | 4.20 | 1.02 | 1.03 | 0.72 | 0.40 | <0.10 |
| L128R | WR | 1.05 | 0.30 | 0.30 | 0.31 | <0.10 | <0.10 |
| Y139C | Rw | 9.74 | 10.44 | 9.47 | 8.77 | 8.23 | 6.71 |

FIGURE 11

Amino acid sequence of Homo sapiens vitamin K epoxid recycling polypeptide (HS_VKORC1; SEQ ID NO: 1)

```
Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
            35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
            85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Trp Ile Leu Phe Phe Val Leu
            115                 120                 125

Tyr Asp Phe Cys Ile Val Cys Ile Thr Thr Tyr Ala Ile Asn Val Ser
            130                 135                 140

Leu Met Trp Leu Ser Phe Arg Lys Val Gln Glu Pro Gln Gly Lys Ala
145                 150                 155                 160

Lys Arg His
```

FIGURE 12

Nucleic acid coding sequence of Homo sapiens vitamin K epoxid recycling polypeptide
(HS_VKORC1; SEQ ID NO: 2)

```
atgggcagca cctgggggag ccctggctgg gtgcggctcg ctctttgcct gacgggctta
60 gtgctctcgc tctacgcgct gcacgtgaag gcggcgcgcg cccgggaccg ggattaccgc
120 gcgctctgcg acgtgggcac cgccatcagc tgttcgcgcg tcttctcctc caggtggggc
180 aggggtttcg gctggtgga gcatgtgctg ggacaggaca gcatcctcaa tcaatccaac
240 agcatattcg gttgcatctt ctacacacta cagctattgt taggttgcct gcggacacgc
300 tgggcctctg tcctgatgct gctgagctcc ctggtgtctc tcgctggttc tgtctacctg
360 gcctggatcc tgttcttcgt gctctatgat ttctgcattg tttgtatcac cacctatgct
420 atcaacgtga gcctgatgtg gctcagtttc cggaaggtcc aagaacccca gggcaaggct
480 aagaggcact ga
492
```

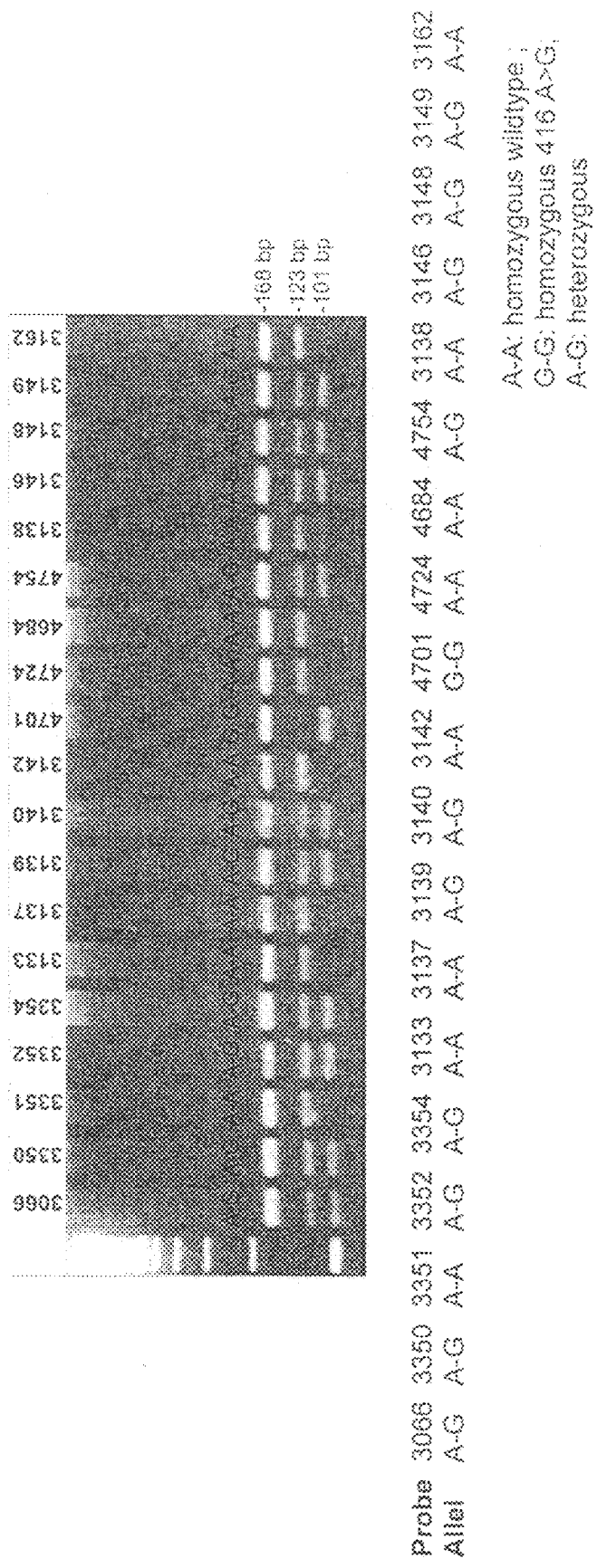
Figure 13. Detecting the warfarin resistance mutation Y139C (416A>G) of the VKORC1 gene in the genome of *Rattus norvegicus* using ARMS-PCR

VITAMIN K EPOXIDE RECYCLING POLYPEPTIDE VKORC1, A THERAPEUTIC TARGET OF COUMARIN AND THEIR DERIVATIVES This application claims priority to U.S. provisional application No. 60/511,041 filed Oct. 14, 2003.

FIELD OF THE INVENTION

The invention relates to a novel polypeptide vitamin K epoxide recycling polypeptide (VKORC1) as a target for coumarin and its derivatives. The invention further provides methods for identifying coumarin derivatives, and also claims VKORC1 polypeptides and VKORC1 nucleic acids containing a sequence abnormality associated with aVKORC1 associated deficiency such as warfarin resistance, wherein the VKORC1 polypeptides and VKORC1 nucleic acids can be used for diagnosing these deficiencies. Moreover, the invention relates to methods for identifying coumarin derivatives usable in pest control of rodents.

BACKGROUND OF THE INVENTION

Repression of untimely blood coagulation is the therapeutic option of choice for acute treatment and long-term prevention of thrombolic events. Among the anti-coagulants coumarins are widely used for the prevention of thrombosis such as in patients immobilized after surgery, patients having a chronic heart failure, patients having atherosclerotic vascular disease, patients having a malignancy, and patients that are pregnant. Moreover, coumarins are the most widely used oral anticoagulants for the treatment and prophylaxis of thrombosis [Suttie, 1987]. Coumarins are typically derivatives of 6-hydroxycoumarin, such as 3-(acetonylbenzyl)-4-hydroxycoumarin (COUMADIN®).

The coumarins target the blood coagulation cascade indirectly by inhibition of the vitamin K cycle.

Vitamin K is an essential cofactor for the post-translational activation by gamma-carboxylation of a group of regulatory proteins, the Gla-proteins. In several metabolic pathways, some key proteins require carboxylation for proper function. The blood coagulation cascade is the best-studied example. Here, the procoagulant factors II, VII, IX and X, and the anticoagulant factors protein C, protein S, protein Z are dependent on gamma-carboxylation. This post-translational modification enables the attachment of the modified proteins—in the presence of calcium—to phospholipid-bilayer membranes which is an essential step in the activation of blood coagulation [Sperling et al., 1978] [Esmon et al., 1975]. Other proteins requiring gamma-carboxylation are the matrix gla protein and osteocalcin, both regulators of bone metabolism [Price, 1988] and the "growth arrest specific gene", a signal transduction protein of the cell cycle [Manfioletti et al., 1993] [Stitt et al., 1995].

During gamma-carboxylation, a carboxyl group is introduced into glutamate residues of the target proteins by the enzyme gamma-glutamyl carboxylase (GGCX) in liver microsomes [Furie & Furie, 1988] [Suttie, 1987]. The reaction requires as a cofactor stoichiometric amounts of reduced vitamin. K1 hydroquinone (vitamin K1H2) which is oxidized to vitamin K-2,3 epoxide [Cain et al., 1997]. The regeneration of the active cofactor is mediated by a multi-protein complex termed vitamin K-2,3-epoxide reductase (VKOR) [Wallin & Martin, 1985]. The same complex is targeted by the coumarin-type poisons used in rodent pest control. This "vitamin K cycle" has been characterized biochemically in great detail but the molecular components have not yet been purified to homogeneity [Guenthner et al., 19981]. Moreover, the molecular nature of coumarin activity and the molecules interacting with coumarins are still elusive.

It is generally appreciated in the art that although largely effective, there are a number of limitations to the use of coumarins. First of all; there are humans that are inert to coumarin treatment. The term warfarin resistance (WR) is used for individuals who maintain normal clotting factor activities despite oral anticoagulation by coumarins (OMIM Access. No. 122700). Autosomal dominant transmission has been observed in several pedigrees [O'Reilly et al., 1964] [O'Reilly, 1970]. Combined deficiency of all vitamin K dependent clotting factors (VKCFD) is a very rare bleeding disorder in humans of autosomal recessive inheritance with 14 cases described as yet [McMillan & Roberts, 1966] [Fischer, 1966] [Johnson et al., 1980] [Goldsmith et al., 1982] [Vicente et al., 1984] [Ekelund et al., 1986] [Pauli et al., 1987] [Leonard, 1988] [Pechlaner et al., 1992] [Boneh & Bar-Ziv, 1996] [Brenner et al., 1998] [Spronk et al., 2000] [Oldenburg et al., 2000]. Clinical symptoms of the disease include episodes of perinatal intracerebral hemorrhage sometimes with fatal outcome. The bleeding tendency is usually completely reversed by oral administration of vitamin K. Additional symptoms in newborns can resemble warfarin embryopathy with nasal and distal phalangeal hypoplasia and premature calcification of epiphyses [Pauli et al., 1987]. The disease may result either from a defective resorption/transport of vitamin K to the liver [Prentice, 1985] or from mutations in one of the genes involved in gamma-carboxylation. In subtype 1 (VKCFD1, OMIM # 277450), mutations in the GGCX gene on chromosome 2p12 result in insufficient carboxylation of clotting factors [Brenner et al., 1998] [Spronk et al., 2000]. There has been described a linkage of two kindreds with familial multiple coagulation factor deficiency (FMFD, now re-named: VKCFD2, OMIM #607473) to a 20 Mb interval of the pericentric region of chromosome 16p12-q21 [Fregin et al., 2002]. Patients with VKCFD2 showed significantly increased serum levels of vitamin K epoxide, thus suggesting a defect in one of the subunits of the VKOR complex. Taken together, there is evidence that there are patients that display warfarin resistance. As a result, there is a need to identify novel coumarins derivatives that are effective anticoagulants for treating these patients, and methods for identifying these coumarin derivatives.

The use of coumarins is associated with a risk of spontaneous bleedings, with a significant mortality rate. Moreover, the prediction of the accurate coumarin maintenance dose is difficult. In the absence of the target molecule which coumarin exerts an effect on, the treatment regimen has to be established, on a patient-by-patient basis. During the time the optimum regimen is yet not established the patient either suffers from an increased risk of thrombogenesis or of an increased risk of bleeding. Therefore there is a need for a method of determining the optimal treatment regimen that is faster and saver. Further, establishing an optimal treatment regimen is complicated by the fact, that there is a considerable delay between the administration of coumarins and the onset of its anticoagulant activity. Given the delayed action of coumarin and given the fact that coumarin tends to accumulate in time there is a need for coumarin derivatives that effect blood coagulation faster than the coumarins known in the art. By the same token there is also a need for coumarins that are metabolized more rapidly so that accumulation of coumarin may be prevented or ameliorated and as a result the danger of overdosing is decreased or abolished.

It is well appreciated that if coumarin treatment is initiated during a thrombic state, the levels of protein C and S decline, thus temporarily creating a thrombogenic potential which is usually compensated for by overlapping heparin and coumarin administration for a number of days. Again, there is a need to identify the molecular target of coumarin action in order to be able to screen for novel coumarin derivatives that do not possess these limitations or at least to a lesser extend.

A coumarin therapy sometimes induces skin necrosis in patients and if applied during pregnancy may cause embryopathy creating a need for novel coumarin derivatives which do not cause these effects.

There are a number of interactions between drugs and coumarins. Some of these drugs like Phenobarbital induce lower plasma levels of coumarins due to an increased metabolization of coumarin which is believed to be caused by the mixed-function oxidases like the cytochrome P450 mixed-function oxidases. Such interaction is of clinical relevance if the appropriate regimen of e.g. Phenobarbital and coumarin has been determined and later on only administration of Phenobarbital is discontinued leading to a rise of the plasma level of coumarin which causing excessive anticoagulation. Other drugs like Amiodarone cause a delayed metabolization of coumarin leading again to excessive anticoagulation if co-administered with coumarins. Since the molecules affected by coumarins are not known in the art there is a need to develop novel coumarins and tools to identify the latter in order to solve these problems.

Finally, coumarins, especially warfarin, are not only used in humans but since the 1950s, coumarins have been in use as an active ingredient in rodenticidal compositions. The basis for the effectiveness of warfarin as a rodenticide lies in the fact that it is an effective anti-coagulant in small, multiple doses. One or two doses of the compound are seldom fatal if taken at the recommended concentration; thus the hazard of acute toxicity to man, domestic animals, and wildlife is greatly reduced. Usually the rodents begin to die after four or five daily doses of the materials, and the population is greatly reduced or eradicated in approximately three weeks. Death is caused by hemorrhages, brought about by the action of the warfarin in reducing the clotting power of the blood. These hemorrhages may be external or internal and can be initiated by very slight injury or capillary damage. One of the other advantages of coumarins is that, because multiple ingestions are required to kill the rodents, they do not develop bait shyness. Beginning in 1969, rodents—particularly rats and, to a somewhat lesser extent, mice—began showing resistance to warfarin baits. The general assumption was that such resistance had a genetic basis. As for the mechanism, it is the VKORC1 complex mentioned above that is targeted by derivatives of warfarin in use for rodent pest control [Jackson et al., 1988]. Resistance to coumarin derivatives has arisen spontaneously in several wild rodent populations rendering the use of these drugs locally ineffective for pest control. Autosomal dominant loci for warfarin resistance have been mapped in the mouse (War) to chromosome 7 [Wallace et al., 1976] and in rat (Rw) to the long arm of chromosome 1[Greavses & Ayres, 1967] [Kohn & Pelz, 1999]. Since the VKOR complex is the target of the coumarin drugs resistance is thought to be mediated by alterations in one of its protein components [Jackson, 1988]. The development of resistance in rodents has created a need for identifying the target of coumarins action which would facilitate the development of novel coumarin-derivatives for use in pest control.

Taken together it is an object of the present invention to provide a target molecule for coumarin and its derivatives in mammals. It is another object of the present invention to provide methods for identifying novel coumarins which solve at least one of the problems mentioned above. It is a further object of the present invention to identify polypeptides and nucleic acids coding for them which cause warfarin resistance in human and non-human mammals, preferably rodents. It is also an object of the present invention to diagnose, prevent and/or treat disorders and diseases selected from diseases from warfarin resistance, familial multiple factor deficiency, a disorder or disease associated with increased blood coagulation such as patients suffering from a thrombus and/or patients having an increased risk of developing a thrombus, such as an inherited increased risk of thrombogenesis, preferably an increased risk of thrombogenesis due to a surgery or due to pregnancy, and increased vascular calcification. Moreover, it is also an object of the present invention to diagnose, prevent and/or treat diseases or disorders associated with attenuated blood coagulation, such as hemophilia, disorder associated decreased vascular calcification and disorders and diseases with an increased risk of bleeding. Finally, it is an object of the present invention to provide a method for identifying coumarin and its derivatives which are effective in pest control of non-human mammal and compositions for killing rodents.

SUMMARY OF THE INVENTION

In solving the above objects a vitamin K epoxide recycling polypeptide (VKORC1) is provided, comprising or consisting of a polypeptide sequence selected from the group consisting of:
(a) a polypeptide sequence selected from the group consisting of a sequence according to SEQ ID No. 1, 12, 17, 21, 25, and 27;
(b) a polypeptide sequence of an allele of the polypeptide sequence defined in (a);
(c) a polypeptide sequence having at least 80% homology with the polypeptide sequence defined in (a) or (b), which polypeptide sequence has VKORC1 activity; and
(d) a polypeptide sequence of a fragment of the polypeptide sequence defined in (a), (b) or (c) having VKORC1 activity.

Moreover, according to another aspect of the present invention there is provided a nucleic acid coding for the VKORC1 polypeptide according to the invention (VKORC1 nucleic acid).

In addition, according to another aspect of the present invention there is provided a method of identifying a coumarin derivative which exerts an effect onto the activity of VKORC1 polypeptide according to the invention comprising the steps of:
(I) providing a host cell having been introduced the VKORC1 nucleic acid or a vector containing the VKORC1 nucleic acid;
(II) expressing the VKORC1 polypeptide in the host cell;
(III) administering a candidate coumarin derivative;
(IV) determining the activity of VKORC1 polypeptide (candidate activity value);
(V) comparing the candidate activity value with a control activity value; and
(VI) identifying the candidate coumarin derivative as a coumarin derivative exerting an effect onto the activity of the VKORC1 polypeptide, provided the candidate activity value is significantly different from the control activity value.

Furthermore, according to another aspect of the present invention there is provided a method of determining a VKORC1 polypeptide sequence which conveys a coumarin effect exerted onto VKORC1 activity, comprising the steps of:
(I) providing a cell expressing the VKORC1 polypeptide according to the invention, which VKORC1 polypeptide has at least one sequence abnormality;
(II) administering coumarin or a derivative thereof to the cell;
(III) determining the activity of the VKORC1 polypeptide (sequence abnormality activity value); and
(IV) comparing the sequence abnormality activity value with the control sequence activity value,
wherein a significant deviation of the sequence abnormality activity value from to the control sequence activity value is indicative that the sequence abnormality of the VKORC1 polypeptide conveys the coumarin effect exerted onto VKORC1 polypeptide.

In another aspect of the present invention there is provided a VKORC1 polypeptide according to the invention, wherein the VKORC1 polypeptide contains at least one sequence abnormality, which exerts an effect on the activity of the VKORC1 polypeptide.

Moreover, according to another aspect of the present invention there is provided a method of diagnosing a VKORC1 associated deficiency in a patient comprising the steps of:
(I) amplifying a DNA sample obtained from the patient or reverse transcribing a RNA sample obtained from the patient into a DNA and amplifying the DNA; and
(II) analyzing the amplified DNA of step (I) to determine at least one sequence abnormality in a nucleic acid sequence coding for the VKORC1 polypeptide of claim 1 or in an amino acid sequence of the VKORC1 polypeptide;
wherein the determined sequence abnormality is indicative of the patient suffering from a VKORC1 associated deficiency; preferably the sequence abnormality exerts an effect on the activity of the VKORC1 polypeptide.

In addition, according to another aspect of the present invention there is provided a method of identifying a coumarin derivative which is toxicologically effective in warfarin-resistant rodents comprising the steps of:
(I) providing a warfarin-resistant rodent;
(II) administering a candidate coumarin derivative to the rodent;
(III) determining the toxicity of the candidate coumarin derivative onto the rodent (candidate coumarin derivative toxicity value);
(IV) comparing the candidate coumarin derivative toxicity value with a control coumarin toxicity value;
(V) identifying the candidate coumarin derivative as a rodenticidally effective coumarin derivative provided that the candidate coumarin derivative toxicity value is significantly larger than the control coumarin toxicity value.

According to another aspect of the present invention, the identified coumarin derivatives can be included into a composition for killing rodents.

BRIEF DESCRIPTION OF THE DRAWINGS

FIG. 3 shows a sequence alignment of VKORC1 and VKORC1 like protein 1 (VKORC1L1) polypeptides. The alignment was generated with CLUSTALW and PRETTYBOX. Human (hVKORC1) (SEQ ID NO:1), mouse (mVKORC1) (SEQ ID NO:17) and rat VKORC1 (rVKORC1) (SEQ ID NO:12) and VKORC1L1 polypeptides, i.e. VKORC1L1 of human (hVKORC1L1) (SEQ ID NO:10), mouse (mVKORC1L1) (SEQ ID NO:19) and *Fugu rubripes* (fVKORC1L1) (SEQ ID NO:23), share approximately 84% sequence identity within both groups and approximately 50% identity between both groups of proteins, xVKORC1 (SEQ ID NO:25) depicts the VKORC1 polypeptide sequence of *Xenopus laevis*, fVKORC1 (SEQ ID NO:21) the VKORC1 polypeptide sequence of *Fugu rubripes*, and aVKORC1 (SEQ ID NO:27) the VKORC1 polypeptide sequence of *Anopheles gambiae*. Tree analysis allows grouping the *Fugu rubripes, Xenopus laevis* and *Anopheles gambiae* proteins to the appropriate group. The locations of the predicted transmembrane domains are underlined. Residues 29, 45, 58 and 128 mutated in WR patients are conserved in all species. The arginine at position 98 mutated in the VKCFD2 patients is conserved in human, rat and mouse (plus sign).

FIG. 6 displays a list of siRNA sequences for homo sapiens VKORC1 and primers endoding these siRNAs which can be used to express them using for example the siLentGene™ U6 Cassette RNA Interference System.

FIG. 7 displays locations of siRNA targets in the coding sequence of homo sapiens vitamin K epoxide reductase complex subunit 1 (Hs_VKORC1) (SEQ ID NO:2), which are shown in light grey; regions which are part of two possible siRNA targets are shown in darker grey; and regions with two or more possible siRNA sequences are shown in an even darker grey.

FIG. 8 provides a list of PCR primer sequences and PCR conditions for amplification of Homo sapiens VKORC1 and Homo sapiens VKORC1L1.

FIG. 9 provides a listing of the sequences their respective SEQ ID NOs.

FIG. 10 shows VKOR activities of HEK293 cells transfected with VKORC1 cDNA. Values are given as percent vitamin K epoxide converted into vitamin K quinone (product/residual substrate+product). Wildtype VKORC1 activity is also defined by being sensitive to warfarin (4.3% residual activity at 80 µM warfarin compared to not inhibited). Mutations Y139C and V29L leading to resistance to warfarin exhibit 69 and 11% residual activity at 80 µM warfarin respectively). All tests were run in duplicate. Untransfected and mock-transfected showed 1.49 and 0.96% activities, and were >90% inhibited by 10 µM warfarin. For further details see Example 7.

FIG. 11 shows the amino acid sequence of Homo sapiens vitamin K epoxide recycling polypeptide (HS_VKORC1; SEQ ID NO: 1)

FIG. 12 shows the nucleic acid coding sequence of Homo sapiens vitamin K epoxide recycling polypeptide (HS_VKORC1; SEQ ID NO: 2)

FIG. 13 shows the result of an ARMS-PCR experiment to determine whether or not a tested rat is warfarin resistant. Wildtype rats exhibited a band at 123 bp (probe# 3351, 3133, 3137, 3142, 4724, 4684, 3138, 3162), rats homozygous to the mutation (probe# 4701) exhibited a band at 101 bp and finally, rats with the heterozygous mutation (probe# 3066, 3350, 3352, 3354, 3139, 3140, 4754, 3146, 3148, 3149) showed two bands, one at 101 and another band at 123 bp. For further details see Example 9.

DETAILED DESCRIPTION OF THE INVENTION

Figure 5:
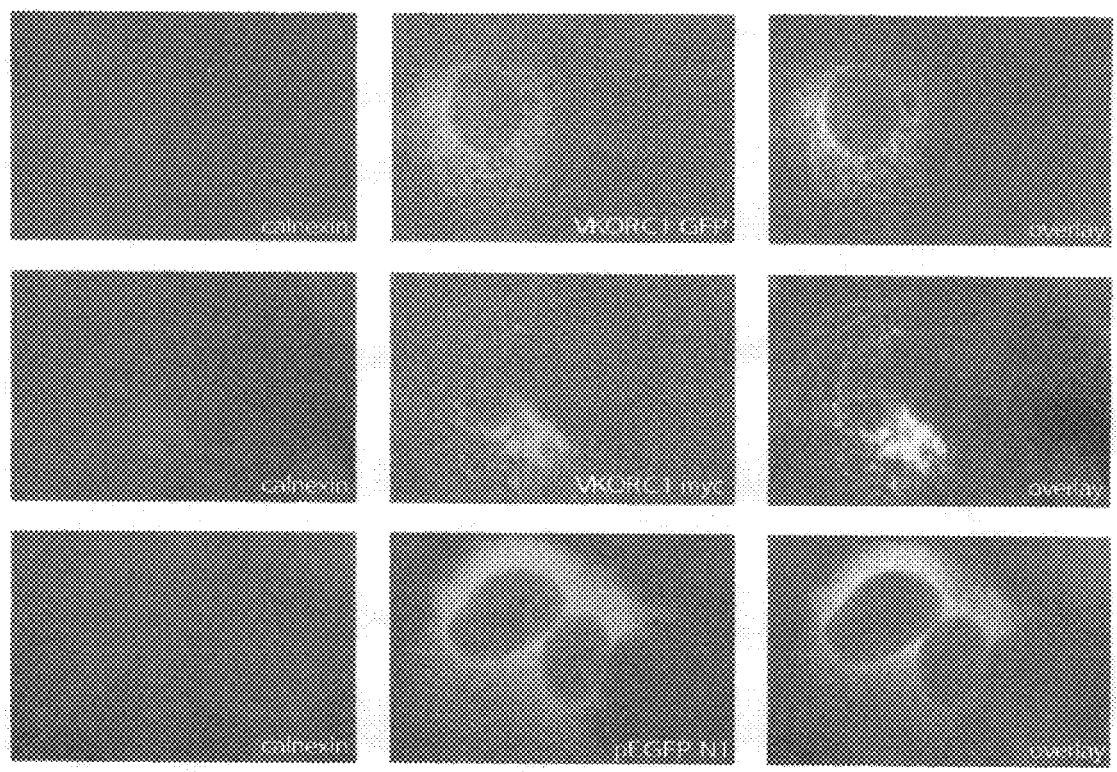
FIG. 5 shows the subcellular location of VKORC1. For more details see example 6. To this end, COS-7 cells transiently transfected with VKORC1 constructs were stained with anti-calnexin (red; left column) and anti-GFP or anti-myc, respectively (green; middle column). Merged figures of the double-stained cells are shown in the right column. Both VKORC1 constructs (tagged with GFP or myc) co-localize with the ER specific calnexin staining. The control construct (pEGFP-N1) shows a diffuse staining pattern throughout the cytoplasm.

In order to meet the needs for developing novel coumarin derivatives and for identifying the target of coumarin and its derivatives the vitamin K epoxide recycling polypeptide (VKORC1) was cloned. This gene was previously unknown spanning a genomic region of 5126 bp and comprising three exons coding for a protein of 163 amino acids. Topology analysis suggests a highly hydrophobic protein with at least two transmembrane domains. This is compatible with the known location of the VKORC1 complex activity in ER membranes and with immunofluorescence data in COS-7 cells transfected with VKORC1 constructs (FIG. 5).

The VKORC1 gene was surprisingly identified in a mutant screen of warfarin resistant patients (for details cf. examples 1 and 2). According to the present invention, there has been surprisingly identified a gene, VKORC1, which is mutated in patients with a combined deficiency of all vitamin K dependent coagulation factors (VKCFD2) and with warfarin resistance (WR), respectively, showing that VKORC1 polypeptide contains a binding site for warfarin and is a target of coumarin and its derivatives. The evidence that the mutations are causative of the two phenotypes is as follows:
(i) an R98W mutation segregates with the disease in two unrelated families with VKCFD2;
(ii) this arginine at position 98 is conserved in the human and in the homologous mouse and rat genes, respectively;
(iii) three warfarin resistant brothers share an R58G substitution;
(iv) this amino acid and the other residues found mutated in two more unrelated WR patients (V29L and L128R) are conserved in all species analyzed except for three bacterial genes (see FIG. 3); and
(v) none of the 5 presumed mutations was found in 192 control DNA samples.

Figure 3:
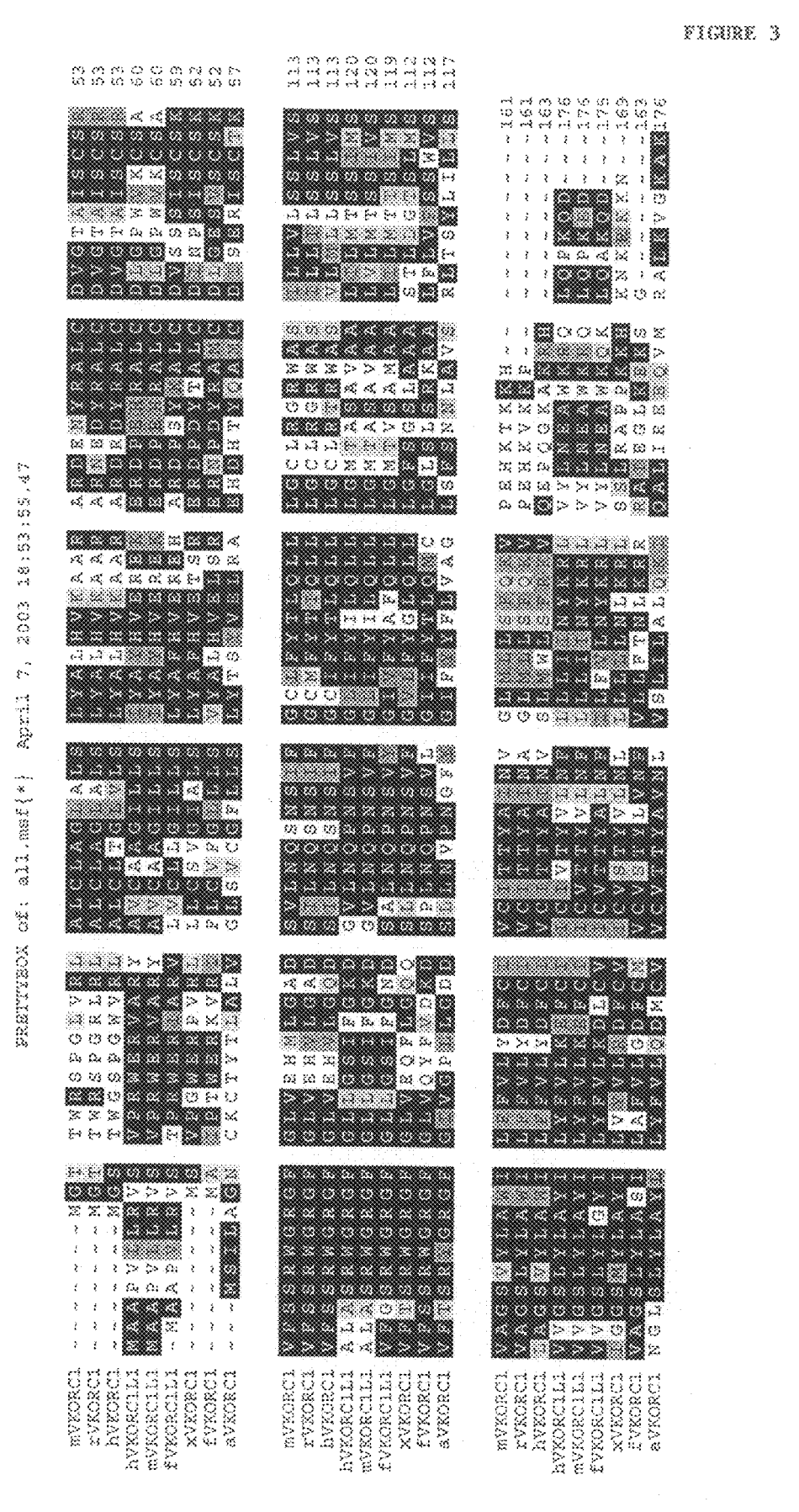

Moreover, homology searches in genome and protein databases have not revealed any similarities of VKORC1 to any protein or peptide domain of annotated function. However, homologous genes are found in vertebrates (rat, mouse, *Xenopus, Fugu*), insects (Anopheles) and bacteria (FIG. 3). Surprisingly, the three mammals and Fugu each have a second VKORC1-like gene of moderate similarity to the cognate gene. A number of amino acid positions within these genes are conserved throughout evolution. This is in accordance with the well established fact that gamma-carboxylation—and thus the use of vitamin K as a cofactor of this process—is an evolutionary old post-translational protein modification [Bandyopadhyay et al., 2002].

A substitution of valine 29, arginine 58 leucine 128—although dispersed over the entire VKORC1 polypeptide—obviously renders the inhibition of VKORC1 activity by warfarin ineffective. It can be speculated that these amino acids functionally co-operate in the tertiary structure of the VKORC1 protein 1. Taken together the mutation data in patients with two different phenotypes provide VKORC1 as the target protein, both for vitamin K and warfarin binding.

In one aspect of the present invention there is provided a vitamin K epoxide recycling polypeptide (VKORC1) comprising, preferably consisting of, a polypeptide sequence selected from the group consisting of:
(a) a polypeptide sequence selected from the group consisting of a sequence according to SEQ ID No. 1, 12, 17, 21, 25, and 27;
(b) a polypeptide sequence of an allele of the polypeptide sequence defined in (a);
(c) a polypeptide sequence having at least 80% homology with the polypeptide sequence defined in (a) or (b), which polypeptide sequence has VKORC1 activity; and
(d) a polypeptide sequence of a fragment of the polypeptide sequence defined in (a), (b) or (c) having VKORC1 activity.

Preferably, the VKORC1 polypeptide is a target for coumarin and its derivatives in mammals.

Within the meaning of the invention the term "VKORC1 polypeptide" refers to the full length sequence of the VKORC1 polypeptide as defined in the preceding paragraph. The term "VKORC1 polypeptide" also encompasses isolated VKORC1 polypeptides and VKORC1 polypeptides that are prepared by recombinant methods, e.g. by isolation and purification from a sample, from a host cell expressing the VKORC1 polypeptide, by screening a library and by protein synthesis, all of these methods being generally known to the person skilled in the art. Preferably, the entire VKORC1 polypeptide or parts thereof can be synthesized, for example, with the aid of the conventional synthesis such as the Merrifield technique. More preferably, the term "VKORC1 polypeptide" also encompasses polypeptides which have a sequence homology of about 80%, preferably about 90%, in particular about 95%, especially about 98% with the VKORC1 polypeptide according to one of SEQ ID No. 1, 12, 17, 21, 25, and 27, provided that such VKORC1 polypeptide has VKORC1 activity. Moreover, it is preferred that the term "VKORC1 polypeptide" also encompasses homologous polypeptides which originate from organisms other than human, preferably from non-human mammals such as, rodents, e.g. mouse, rats, or monkeys and pigs and other vertebrates and invertebrates, such as those amino acid sequences according to SEQ ID Nos. 12, 17, 21, 25, 27, provided that such VKORC1 polypeptide has VKORC1 activity. It is even more preferred that the term "VKORC1 polypeptide" also includes VKORC1 polypeptides which are encoded by different alleles of the gene, in different individuals, in different organs of an organism or in different developmental phases, provided that such VKORC1 polypeptide has VKORC1 activity. It is further intended that the term "VKORC1 polypeptide" preferably also encompasses naturally occurring or synthetic mutations that exert no or only insignificant effects onto the activity of the VKORC1 polypeptide. Other polypeptides preferably encompassed by the term "VKORC1 polypeptide" include VKORC1 polypeptides that may arise from differential splicing of the VKORC1 transcript, provided that such VKORC1 polypeptide has VKORC1 activity.

The term "fragment of the polypeptide sequence" is intended to encompass partial sequences of VKORC1 polypeptides, which fragments comprise, preferably consist of at least about 60%, preferably at least about 70%, more preferably at least about 80%, more preferably at least about 90%, even more preferably at least about 95% of the full length sequence of the VKORC1 polypeptide. In particular, it is preferred that the fragment consists of a single contiguous sequence of the VKORC1 polypeptide but it may also contain at least two, at least three or at least about five different sequence portions of a VKORC1 polypeptide according to the invention which may or may not be interspaced by a heterologous sequence or contain no extra polypeptide sequence at all.

The term "sequence homology" is understood as the degree of identity (% identity) of two sequences, that in the case of polypeptides can be determined by means of for example BlastP 2.0.1 and in the case of nucleic acids by means of for example BLASTN 2.014, wherein the Filter is set off and BLOSUM is 62 (Altschul et al., 1997).

"VKORC1 activity" within the meaning of the present invention is intended to mean the biological activity of the VKORC1 polypeptide of SEQ ID No.1. More preferably, "VKORC1 activity" is defined as the activity of the VKORC1 polypeptide to enzymatically convert (or support the enzymatic conversion) of vitamin K2,3-epoxide to vitamin K-quinone and/or the conversion of vitamin k quinone to vitamin K hydroquinone. VKORC1 activity may be determined using an assay based on the experiments described in detail in example 7 and FIG. 10. Using that assay, a measured percentage of vitamin K epoxide converted into vitamin K quinone (product/substrate+product) in cells expressing a given VKORC1 polypeptide, or a nucleic acid molecule coding for such VKORC1 polypeptide, which raises the basal VKOR-activity of HEK293 cells from about 1% (1.49 and 0.96% for untransfected and mock-transfected HEK293 cells, respectively) to about 15% or more, preferably to about 18% or more, preferably to about 20% or more, most preferably to about 25% or more is considered a VKORC1 activity within the meaning of the invention.

The VKORC1 polypeptides according to the present invention may be produced by a method described in more detail below. Among others, the VKORC1 polypeptides are useful for identifying coumarin derivatives that avoid the problems described above. In particular they are useful for identifying coumarin derivatives, that effectively inhibit VKORC1 activity and that in independent assays are tested for (1) their metabolic half life in order to identify coumarin derivatives that are metabolized faster than the coumarins known in the art, (2) their ability to cause skin necrosis to identify coumarin derivatives that do not cause skin necrosis or to a lesser extend than the coumarins known in the art, (3) coumarin derivative-drug interactions in order to identify coumarin derivatives with lesser side effects than the coumarins known in the art. Moreover, the VKORC1 polypeptides according to the present invention are useful for identifying a VKORC1 sequence interacting with coumarin and its derivatives, and for treating patients having a decreased or increased VKORC1 activity relative to control levels.

In another aspect the present invention relates to a VKORC1 nucleic acid comprising, preferably consisting essentially of a nucleic acid sequence selected from the group consisting of:
(a) a nucleic acid sequence coding for the VKORC1 polypeptide according to the invention;
(b) a nucleic acid sequence selected from the group consisting of a sequence according to SEQ ID No. 2, 13, 18, 22, 26, and 28;
(c) a nucleic acid sequence which hybridizes under stringent conditions to the nucleic acid sequence defined in (a) or (b), which nucleic acid sequence codes for a polypeptide having VKORC1 activity;
(d) a nucleic acid sequence which, but for the degeneracy of the genetic code, would hybridize, preferably under stringent conditions, to the nucleic acid defined in (a), (b) or (c) and which nucleic acid sequence codes for a polypeptide having VKORC1 activity; and
(e) a fragment of the nucleic acid sequence defined in (a), (b), (c) or (d), which fragment codes for a polypeptide having VKORC1 activity.

Preferably, the VKORC1 nucleic acid is a target for coumarin and its derivatives in mammals.

The term "VKORC1 nucleic acid" relates to RNA or DNA, which may be a single or preferably a double stranded molecule. The sequence of the VKORC1 nucleic acid may further comprise at least one intron and/or one polyA sequence. The term "VKORC1 nucleic acid" may also encompass a precursor stage, for example a propolypeptide or prepropolypeptide, thereof. It is also understood that untranslated sequences can be present at the 5' end and/or the 3' end of the nucleic acid, without the activity of the encoded polypeptide being significantly altered. However, the DNA region encoding the VKORC1 polypeptide is particularly preferred. In eukaryotes, this region begins with the first start codon (ATG) which is located in a Kozak sequence (Kozak, 1987) and extends to the next stop codon (TAG, TGA or TAA) which is located in the same reading frame as the ATG. In the case of prokaryotes, this region begins with the first AUG (or GUG) after a Shine-Dalgarno sequence and ends with the next stop codon (TAG, TGA or TAA) which is located in the same reading frame as the ATG. Moreover, the term "VKORC1 nucleic acid" may also encompass sequences which exhibit at least about 70%, in particular at least about 80%, especially at least about 90%, sequence homology with the sequence according to SEQ ID No. 2, 13, 18, 22, 26, and 28, preferably to the sequence according to SEQ ID No. 2, provided that the VKORC1 polypeptide encoded by such nucleic acid has VKORC1 activity. In a preferred embodiment of the invention the nucleic acid comprises a nucleic acid having a sequence complementary and/or antisense to a VKORC1 nucleic acid as defined in the preceding paragraph. The VKORC1 nucleic acid may also comprises a non-functional mutant variant of the VKORC1 nucleic acid as defined above, such a variant containing a single nucleotide polymorphism (SNP) such as the nucleic acid sequences according to SEQ ID No. 8 and 9, provided that the VKORC1 polypeptide encoded by such nucleic acid has VKORC1 activity.

The term "stringent hybridization conditions" is to be understood, in particular, as meaning those conditions in which a hybridization takes place, for example, at 60° C. in 2.5×SSC buffer followed by several washing steps at 37° C. in a lower buffer concentration and remains stable.

The term "fragment of the nucleic acid sequence coding for a polypeptide having VKORC1 activity" is understood to encompass nucleic acid sequence fragments comprising, preferably consisting of at least about 60%, preferably at least about 70%, more preferably at least about 80%, more preferably at least about 90%, even more preferably at least about 95% of the full length sequence coding for VKORC1 polypeptide according to the invention, preferably coding for the polypeptide according to SEQ ID No. 1, provided that the polypeptide encoded by such fragment has VKORC1 activity. In particular, it is preferred that the fragment consists of a single contiguous sequence coding for the VKORC1 polypeptide but it may also contain at least two, at least three or at least about five different sequence portions, which may or may not be interspaced by a heterologous sequence or contain no extra nucleic acid sequence at all, provided that all the sequence portions are arranged in the same reading frame. It is essential to the definition of these fragments that they display VKORC1 activity.

The VKORC1 nucleic acids can be produced by methods generally known to the skilled artisan. Nucleic acids may be prepared synthetically. Thus, the VKORC1 nucleic acids can, for example, be synthesized chemically, e.g. according to the phosphotriester method, with the aid of the DNA sequences as defined above and/or with the aid of the polypeptide sequences which are likewise defined above such as the SEQ ID No. 1 and by referring to the genetic code (see, e.g., Uhlmann, & Peyman, 1990). Preferably the VKORC1 nucleic acids are produced by recombinant gene technology methods generally known to the person skilled in the art.

Among others, the VKORC1 nucleic acids are useful (1) for identifying coumarin derivatives that avoid the problems described above, (2) for producing PCR primers, DNA and RNA probes, siRNA or shRNA, and for VKORC1 polypeptide, (3) for treating patients having a decreased or increased VKORC1 activity relative to control values, and (4) for identifying coumarin derivatives that may be employed for pest control of rodents, all of which are described in detail below.

The present invention further provides in another aspect a method of producing a VKORC1 polypeptide, preferably a polypeptide according to SEQ ID No. 1, 12, 17, 21, 25, and 27, comprising the steps of:
(I) providing a host cell having been introduced the VKORC1 nucleic acid, preferably a nucleic acid according to SEQ ID No. 2, 13, 18, 22, 26, and 28, or a vector containing the VKORC1 nucleic acid;
(II) expressing the VKORC1 polypeptide in the host cell; and
(III) isolating the VKORC1 polypeptide from the host cell.

The host cell can be any host cell as defined below. Methods for selecting and culturing the host cells and for causing the host cells to express a polypeptide are generally known to the person skilled in the art. The same is true for methods of isolating the expressed polypeptide from the host cell; to this end an antibody according to the invention may be used for immunoaffinity precipitation. As an alternative the vector may contain a (poly)peptide tag that allows immunoaffinity precipitation by tag specific antibodies according to standard protocols known to the skilled worker (see also below).

In another aspect the present invention relates to a fusion protein comprising, preferably consisting essentially of,
(a) the VKORC1 polypeptide as defined above, preferably according to SEQ ID No.1, 12, 17, 21, 25, 27 or a polypeptide encoded by the VKORC1 nucleic acid, preferably a nucleic acid according to SEQ ID No. 2, 13, 18, 22, 26, 28 and
(b) a heterologous part.

This involves fusion proteins which contain the above-described VKORC1 polypeptide, with the fusion proteins themselves already being active or only becoming active after the heterologous part has been eliminated. To this end the heterologous part may further comprise a peptide cleavable by a protease. The heterologous part may be a proteinaceous compound, a peptide or a different compound. These fusion proteins include in particular, fusion proteins having a content of about 1-300, preferably about 1-200, particularly preferably about 1-150, in particular about 1-100, especially about 1-50 foreign amino acids constituting the heterologous part. The heterologous part can be located N-terminally, C-terminally and/or internally relative to the VKORC1 polypeptide. Examples of such peptide sequences are prokaryotic peptide sequences which can be derived, for example, from *E. coli* galactosidase.

Other preferred examples of peptide sequences for fusion proteins are peptides which facilitate detection of the fusion protein; examples of these are the green fluorescent protein or functional variants thereof. It is also possible to add on at least one further "polypeptide tag" e.g. for the purpose of purifying the previously described VKORC1 polypeptides. For example, suitable protein tags enable the fusion proteins which are to be purified, to be absorbed with high affinity to a matrix. This is then followed, for example, by stringent washing with suitable buffers without eluting the fusion proteins to any significant extent, and, subsequently, specific elution of the fusion proteins. Examples of the protein tags which are known to the skilled person are a (His)6 tag, a Myc tag, a FLAG tag, a hemagglutinin tag, a glutathione transferase (GST) tag, intein having an affinity chitin-binding tag and a maltose-binding protein (MBP) tag. These protein tags can be located N-terminally, C-terminally and/or internally relative to the VKORC1 polypeptide. Fusion proteins are for example useful for the production of VKORC1 production and subsequent isolation. Moreover, the fusion proteins may be employed for detecting the localization of the expression product in the cell or the organism.

In another aspect the present invention relates to a vector comprising a VKORC1 nucleic acid as defined above, preferably the VKORC1 nucleic acid according to SEQ ID No. 2. Preferably the vector is an expression vector. In order to enable the VKORC1 nucleic acids to be used according to the present invention they may be introduced into a eukaryotic or prokaryotic cell by means of transfection, transformation or infection, and thereby enable the polypeptide to be expressed. The VKORC1 nucleic acid can be present as a plasmid, or as a part of a viral or non-viral vector. Particularly suitable viral vectors in this connection are: baculoviruses, vaccinia viruses, adenoviruses, adeno-associated viruses and herpes viruses. Particularly suitable non-viral vectors are for example: virosomes, liposomes, cationic lipids and polylysine-conjugated DNA. The vectors can be prokaryotic or eukaryotic expression vectors. Examples of prokaryotic expression vectors are the pGEM vectors or pUC derivatives, which are used for expression in *E. coli*, and examples of eukaryotic expression vectors are the vectors p426Met25 or p426GAL1 (Mumberg et al., 1994) which are used for expression in *Saccharomyces cerevisiae*, the Baculovirus vectors, as disclosed in EP B1 0 127 839 or EP B1 0 549 721, which are used for expression in insect cells, and the vectors Rc/CMV and Rc/RSV, or SV40 vectors, which are used for expression in mammalian cells, with all these vectors being generally available. In general, the expression vectors also contain promoters which are suitable for the respective cell, such as the trp promoter for expression in *E. coli* (see, e.g., EP-B1-0 154 133), the Met 25, GAL 1 or ADH2 promoter for expression in yeasts (Russel et al, 1983; Mumberg, see above), and the baculovirus polyhedrin promoter for expression in insect cells (see, e.g., EP B1 0 127 839).

Promoters which permit constitutive, regulatable, tissue-specific, cell type-specific, cell cycle-specific or metabolism-specific expression in eukaryotic cells are suitable, for example, for expression in mammalian cells. Regulatable elements in accordance with the present invention are promoters, activator sequences, enhancers, silencers and/or repressor sequences. Examples of preferred regulatable elements which permit constitutive expression in eukaryotes are promoters which are recognized by RNA polymerase III or viral promoters, CMV enhancer, CMV promoter, SV40 promoter or LTR promoters, e.g. derived from MMTV (mouse mammary tumor virus; Lee et al., 1981) and other viral promoter and activator sequences which are derived from, for example, HBV, HCV, HSV, HPV, EBV, HTLV or HIV. Examples of regulatable elements which permit inducible expression in eukaryotes are the tetracycline operator in combination with an appropriate repressor (Gossen et al., 1994). The expression of VKORC1 nucleic acids preferably takes place under the control of tissue-specific promoters. The expression vectors may be used for preparing a VKORC1 polypeptides, DNA or RNA probes, or siRNA or shRNA, which can be used in accordance with the invention.

In another preferred embodiment of the present invention the vector is a knock-out gene construct. The construction of such constructs and methods for constructing knock-out animals are known to the person skilled in the art, for example, from the U.S. Pat. No. 5,625,122; U.S. Pat. No. 5,698,765; U.S. Pat. No. 5,583,278 and U.S. Pat. No. 5,750,825. Such vectors are for example useful for generating knock-out cells and animals which in turn can be used to identify disorders and diseases associated with impaired VKORC1 activity.

"Impaired VKORC1 activity" within the meaning of the invention relates to a level of activity and/or expression of the VKORC1 protein that is less than control level activity (as defined above) and/or expression determined in a healthy subject; the respective levels of activity may also be determined based on the assay as described in Example 7.

In another aspect the present invention relates to a host cell, preferably a non-human embryonic stem cell, containing one of the aforementioned vectors, preferably an expression vector or a knock-out gene construct. The host cell can be any cell suitable for expression of VKORC1 polypeptides and/or VKORC1 nucleic acids, preferably a HEK293-EBNA cell. Cells can be either prokaryotic or eukaryotic cells, heterologeous or autologous cells. Examples of prokaryotic cells are *E. coli* and examples of eukaryotic cells include primary hepatocytes cells, yeast cells, for example *Saccharomyces cerevisiae* or insect cells. More preferably the host cell is a cell line, e.g. a COS-cell such as COS-7 cells or hepatocytes cell lines such as HepG2 cells. Moreover, the host cell is preferably a non-human embryonic stem cell. Methods for selecting and culturing host cells and for causing the host cells to express a polypeptide are generally known to the person skilled in the art. Processes for the transformation of cells and/or stem cells are likewise well known to a person skilled in the art and include, for example, electroporation or micro-injection. The host cells of the present invention can for example be employed for methods of identifying coumarin derivatives, for producing VKORC1 polypeptides and VKORC1 nucleic acids, siRNAs and shRNAs according to the invention, and for screening new drugs such as coumarin derivatives effecting VKORC1 activity and/or expression.

In another aspect the present invention relates to the provision of a transgenic non-human mammal containing a host cell according to the invention, preferably a non-human embryonic stem cell, as defined above. Transgenic animals in general show a tissue-specifically increased expression of the VKORC1 polypeptides and/or VKORC1 nucleic acids and can be used for the analysis of coagulation disorders and warfarin resistance and for development and evaluation of therapeutic strategies for such disorders. Transgenic animals may further be employed in the production of VKORC1 polypeptides. The polypeptide produced by the animal may for example be enriched in a body fluid of the animal.

In another preferred embodiment of the present invention it is provided a transgenic non-human mammal which is transgenic for a VKORC1 polypeptide which contains at least one sequence abnormality exerting an effect on the activity of the VKORC1 polypeptide as defined in detail below. Preferably the animal is transgenic for the VKORC1 polypeptide according to SEQ ID No. 1, 12, 17, 21, 25, and 27, and preferably the sequence abnormality is selected from the group consisting of V29L, V45A R58G, R98W, L128R, and Y139C. These transgenic animals are for example useful (1) for testing coumarin derivatives for warfarin resistance; (2) for identifying novel coumarin derivatives that are effective anticoagulants in organisms that are resistant or less susceptible to anticoagulant treatment with coumarins known in the art, such as warfarin resistance patients; and (3) as a source of cells expressing VKORC1 polypeptide and/or VKORC1 nucleic acids. Moreover, these animals can be used for identifying novel coumarin derivatives.

Methods for the preparation of transgenic animals, in particular of transgenic mice, are likewise known to the person skilled in the art from DE 196 25 049 and U.S. Pat. No. 4,736,866; U.S. Pat. No. 5,625,122; U.S. Pat. No. 5,698,765; U.S. Pat. No. 5,583,278 and U.S. Pat. No. 5,750,825 and include transgenic animals which can be produced, for example, by means of direct injection of expression vectors according to the present invention into embryos or spermatocytes or by injection of the expression vectors into the pronucleus of the fertilized ovum or by means of the transfection of expression vectors into embryonic stem cells or by nuclear transfer into appropriate recipient cells (Polites & Pinkert, 1994; Doetschman, in Pinkert, 1994, supra; Wood in Pinkert, 1994, supra; Monastersky in Pinkert, 1994, supra).

Within the meaning of the term "VKORC1 associated deficiency" is intended to encompass a disorder or disease that is associated with warfarin resistance, i.e. the patient displays a reduced or abolished susceptibility to treatment with coumarin or its derivatives, preferably the warfarin resistance results from a sequence abnormality of the VKORC1 polypeptide. Moreover, the term preferably also encompasses disorders or diseases associated with a level of activity and/or expression of VKORC1 that differs significantly from the condition in healthy patients, preferably the expression of VKORC1 polypeptide and/or its activity is significantly reduced or abolished which can e.g. be determined by measuring the prothrombin time, e.g. by international normalized ration (INR) protocol. Such VKORC1 associated deficiency may be caused by a sequence abnormality in the VKORC1 polypeptide or VKORC1 nucleic acid as described in detail below. Moreover, when the level of expression and/or activity of VKORC1 polypeptide or VKORC1 nucleic acid is reduced or even completely abolished, gamma-carboxylation of vitamin K dependant proteins may also be impaired as well. Thus, in this context the term "VKORC1 associated deficiency"

also encompasses diseases and/or disorder selected from familial multiple factor deficiency, a disorder or disease associated with decreased blood coagulation, such as hemophilia and a disorder associated decreased vascular calcification, diseases and/or disorders associated with impaired gamma-carboxylation of vitamin K dependant proteins.

It is also conceivable that the level of expression and/or activity of VKORC1 polypeptide will be increased relative to the condition in healthy patients. Such deficiencies which are also encompassed by the term the "VKORC1 associated deficiency" may be caused by a sequence abnormality in the VKORC1 polypeptide and/or the corresponding gene. Moreover, when the level of expression and/or activity of VKORC1 polypeptide or VKORC1 nucleic acid is increased, gamma-carboxylation of vitamin K dependant proteins may be facilitated as well. Thus, in this context the term "VKORC1 associated deficiency" may further comprise deficiencies selected from diseases or disorders associated with increased blood coagulation including patients suffering from a thrombus and/or patients having an increased risk of developing a thrombus, preferably due to a sequence abnormality in the VKORC1 polypeptide or its gene, diseases and/or disorders associated with improved gamma-carboxylation of vitamin K dependant proteins.

It is also possible that a sequence abnormality in the VKORC1 polypeptide and/or the corresponding gene may increase the susceptibility to treatment with coumarin and its derivatives in a patient having such sequence abnormality. As a result patients undergoing coumarin treating may show very low blood coagulation values. Such disorders associated with increased susceptibility to treatment with coumarin are also intended to be encompassed by the term "VKORC1 associated deficiency". Patients carrying a VKORC1 gene having a stop-mutation suffer from such deficiency associated with a increased coumarin sensitivity.

In another aspect the present invention relates to a DNA or a RNA probe directed against the VKORC1 nucleic acid according to the invention, preferably against the VKORC1 nucleic acid selected from according to SEQ ID No.2, 13, 18, 22, 26, and 28. A probe is a nucleic acid molecule that allows detection of a VKORC1 nucleic acid it is directed against it. The probe has a sequence which hybridizes to the target sequence, i.e. the VKORC1 nucleic acid. Preferably the probe allows specific detection of the VKORC1 nucleic acid, i.e. at least under stringent hybridization conditions it does not bind to molecules other than the particular VKORC1 nucleic acid. Suitable probes are, for example, DNA or RNA fragments having a length of about 10 to about 492 nucleotides, preferably having a length of about 10 to about 400 nucleotides, preferably about 10 to about 250 nucleotides, in particular having a length of about 10 to about 150 nucleotides, in particular having the full length of the coding sequence, which sequence can be derived from the VKORC1 polypeptides, preferably selected from the VKORC1 polypeptide according to SEQ ID No. 1, 12, 17, 21, 25, and 27 or taken directly from the VKORC1 nucleic acid, preferably selected from SEQ ID No. 2, 13, 18, 22, 26, and 28. The probes may additionally contain a label suitable for direct or indirect detection such as biotin, a fluorescent label such as fluorescein or a radioactive label such as $[H]^3$ or other labels known to the skilled worker. Detection may be carried out by methods generally known to the skilled worker including northern blotting and cDNA library blotting techniques. The construction of the probes according to the present invention is also known to the skilled worker (cf. construction of nucleic acids described above). Such probes can for example be used for diagnostic purposes and may preferably comprise or consist of the probes suitable for detection of a sequence abnormality such as those selected from the sequences according to SEQ ID NO: 3, 4, 5, 6, 7, 8, 9, 14, and 94.

In another aspect the present invention relates to a PCR primer, preferably a set of at least two PCR primers directed against the VKORC1 nucleic acid, preferably against the VKORC1 nucleic acid according to SEQ ID No. 2, 13, 18, 22, 26, and 28. Suitable primers are, for example, DNA fragments having a length of about 10 to about 100 nucleotides, preferably having a length of about 15 to about 50 nucleotides, in particular having a length of 15, 16, 17, 18, 19, 20, 21, 22, 23, 24, 25, 26, 27, 28, 29, preferably about 30 nucleotides. The design and synthesis of such primers is generally known to the person skilled in the art. The primers may additionally contain restriction sites, e.g. suitable for integration of the amplified sequence into vectors, or other adapters or overhang sequences, e.g. having a label as described in the preceding section. For example, according to the present invention it is possible to prepare a diagnostic based on the polymerase chain reaction (PCR), suitable for detection of VKORC1 sequence abnormalities, preferably based on the assay described in Example 9 (ARMS PCR).

If the amount of expressed VKORC1 is to be determined, PCR primers specific for a VKORC1 nucleic acid will be utilized for diagnostic or therapeutic purposes. To this end RT-PCR technique, preferably quantitative RT-PCR, may be carried out, wherein upon isolation of total or mRNA from the sample the RNA is reverse transcribed into cDNA and subsequently subjected to a PCR reaction using the specific primers according to the invention. This technique is well known to the skilled worker. This opens up a further possibility of obtaining the described VKORC1 nucleic acids, for example by isolation from a suitable gene or cDNA library, for example from a liver disorder-specific or liver specific gene bank, with the aid of a suitable primer. A preferred set of PCR primers and condition for isolating a VKORC1 nucleic acid are provided in Example 5. Examples of preferred PCR primers according to the invention directed against SEQ ID No. 2, are the primers according to SEQ ID No. 53-70 and preferred conditions for using these PCR primers are provided in FIG. 8.

The term "sample" is intended to refer to a biomaterial comprising fetal or adult tissue or cell, preferably tissue or cells, preferably isolated or derived from heart, kidney and lung, pancreas, brain, placenta and skeletal muscle and blood, preferably from liver. The sample can be isolated from a patient or another subject by means of methods including invasive or non-invasive methods. Invasive methods are generally known to the skilled artisan and comprise for example isolation of the sample by means of puncturing, surgical removal of the sample from the opened body or by means of endoscopic instruments. Minimally invasive and non-invasive methods are also known to the person skilled in the art and include for example, collecting body fluids such as blood, preferably by venopuncture, or urine or feces. The term "sample" may also encompass a genomic or an expression library, preferably constructed based on an sample isolated from a patient, in which case techniques for isolation of the cDNA that are generally known to the skilled worker may be used.

In another aspect the present invention provides a small interfering RNA molecule (siRNA) and/or a short hairpin RNA (shRNA) directed against the VKORC1 nucleic acid, preferably against a sequence derived from SEQ ID No. 1, 12, 17, 21, 25, and 27, or a nucleic acid according to SEQ ID No. 2, 13, 18, 22, 26, and 28, which allows decreasing the stability of the VKORC1 nucleic acid and/or inhibiting the translation of the VKORC1 nucleic acid in a cell culture or in vivo. The double-stranded siRNAs mediate sequence-specific, post-transcriptional silencing of a gene's expression by double-stranded RNA. The siRNAs have a very specific structure: 17 to 25, preferably 19, 20, 21, 22, 23, 24, or 25 nucleotides double stranded RNAs with 2 nucleotides 3'-end overhangs. siRNAs are usually derived from longer double stranded RNA molecules by enzymatic cleavage but siRNAs can also be synthesized chemically or enzymatically outside of cells and then delivered to cells (e.g., by transfection). Thus, using siRNA or shRNA the expression of the corresponding genes in cells can be decreased or even silenced both in vivo and in vitro (McManus et al. 2002). shRNAs consist of a first stem portion comprising (I) a sequence of at least 18, preferably a least 19, more preferably at least 20 nucleotides that is complementary to the mRNA sequence of a VKORC1 nucleic acid, preferably a sequence complementary to the SEQ ID No. 2, 13, 18, 22, 26, and 28; and (II) a second stem portion comprising a sequence of at least 18, preferably a least 19, more preferably at least 20 nucleotides that is sufficiently complementary to the first stem portion to hybridize with the first stem portion to form a duplex stem; and (III) a loop portion that connects the two stem portions. The loop portion may comprise at least 4, preferably at least 7, more preferably at least 11 nucleotides. The siRNA or shRNAs may also be included into a vector allowing constitutive expression of the siRNA or shRNAs in the host cell upon transformation of the host cell (cf. WO 03/006477). Strategies to the design of siRNA or shRNAs sequences and methods of constructing and producing these molecules are generally known to the person skilled in the art (cf. McManus et al., supra). The siRNA and shRNA molecules according to the present invention are for example useful for therapeutic regulation of VKORC1 gene expression and for inclusion into methods for identifying coumarin derivatives, e.g. as a positive control for coumarin action. Preferred examples of siRNA sequences according to the invention are listed in FIGS. 6 and 7 and are selected from SEQ ID No. 29, 20, 33, 34, 37, 38, 41, 42, 45, 46, 47, 50. FIG. 6 also provides the respective downstram primers of these siRNA molecules which can be used for integration into vectors so that the siRNA may be expressed in a cell targeted for siRNA expression.

As an alternative approach to silencing VKORC1 activity and/or expression, the present invention provides antisense oligonucleotides directed against the VKORC1 nucleic acid as defined above, preferably according to SEQ ID No 2, 13, 18, 22, 26, and 28, preferably against a sequence derived from SEQ ID No. 1, 12, 17, 21, 25, and 27 (Zheng & Kemeny, 1995; Nellen & Lichtenstein, 1993).

According to another aspect of the present invention there is provided an RNA-aptamere directed against a VKORC1 polypeptide, preferably against a sequence according to SEQ ID No. 1, which RNA-aptamere exerts an effect on the activity of the VKORC1 polypeptide. RNA-aptameres are effective agonists or antagonists of proteins that are targeted by the aptameres, as has been shown for the coagulation factor IXa (Rusconi et al. 2002). An aptamere according to the invention may be used as an anticoagulant by reducing VKORC1-activity in a more fine-tuned manner than the coumarins. For testing aptameres they can be added to a VKORC1-reaction and analyzed by HPLC as described in Example 7.

In another aspect of the present invention there is provided an antibody which specifically recognizes and binds a VKORC1 polypeptide as defined above, preferably a VKORC1 polypeptide according to SEQ ID No.1, 12, 17, 21, 25, and 27, or a fragment of the antibody. The antibody or antibody fragment preferably is a polyclonal or a monoclonal antibody, specific for the VKORC1 polypeptides. The antibody or antibody fragment is produced according to methods generally known to the person skilled in the art by immunizing a mammal, for example a rabbit, with a VKORC1 nucleic acid, or with a VKORC1 polypeptide according to the invention or parts thereof having at least 6 amino acid length, preferably having at least 8 amino acid length, in particular having at least 12 amino acid length, if appropriate in the presence of, for example, Freund's adjuvant and/or aluminum hydroxide gels (see, for example, Harlow & Lane, 1998). The polyclonal antibodies formed in the animal as a result of an immunological reaction can then be easily isolated from the blood according to generally known methods and purified, for example, by means of column chromatography. Monoclonal antibodies can be produced, for example, according to the known method of Winter & Milstein (1991). The antibodies according to the present invention can for example be used for diagnosis of VKORC1 associated deficiencies. Moreover, the antibodies may be useful for elucidating coumarin-VKORC1 interactions. Finally the antibodies may be used to isolate and and/or purify VKORC1 polypeptide from a tissue or cell sample isolated from a patient.

According to the present invention, the term "antibody" or "antibody fragment" is understood as also meaning antibodies or antigen-binding parts thereof prepared by genetic engineering and optionally modified, such as, for example, chimeric antibodies, humanized antibodies, multifunctional antibodies, bi- or oligospecific antibodies, single-stranded antibodies, F(ab) or F(ab)2 fragments (see, for example, EP-B1-0 368 684, U.S. Pat. No. 4,816,567, U.S. Pat. No. 4,816,397, WO 88/01649, WO 93/06213, WO 98/24884).

In another aspect the present invention provides a method of identifying a coumarin derivative which exerts an effect onto the activity of VKORC1 polypeptide as defined above, preferably the VKORC1 polypeptide having the sequence selected from SEQ ID No. 1, 12, 17, 21, 25, and 27, comprising the steps of:

(I) providing a host cell having been introduced the VKORC1 nucleic acid or a vector containing the VKORC1 nucleic acid;
(II) expressing the VKORC1 polypeptide in the host cell;
(III) administering a candidate coumarin derivative;
(IV) determining the activity of VKORC1 polypeptide (candidate activity value);
(V) comparing the candidate activity value with a control activity value; and
(VI) identifying the candidate coumarin derivative as a coumarin derivative exerting an effect onto the activity of the VKORC1 polypeptide, provided the candidate activity value is significantly different from the control activity value.

The determined activity of VKORC1 polypeptide is dithiothreitol-dependent conversion of vitamin K 2,3-epoxide to vitamin K quinone and wherein the significantly different activity value is a candidate activity value which is significantly higher than the control activity value, as described in further detail above and in Example 7 and FIG. 10. If essentially the same concentration of candidate coumarin derivative yields a lower percentage of vitamin K epoxide converted into vitamin K quinone (product/substrate+product) as warfarine does in this concentration, this is indicative of the candidate coumarin derivative having a stronger inhibitory effect than warfarin, and vice versa.

Preferably in the method of identifying a coumarin derivative according to the present invention the control activity value is determined by a method comprising the steps of:

(A) providing a host cell according to step (I);
(B) expressing the VKORC1 polypeptide in the host cell; and
(C) determining the activity of VKORC1 polypeptide (control activity value).

Even more preferably in the method of identifying a coumarin derivative according to the present invention at least one additional compound is introduced into the host cell, which compound is selected from the group consisting of vitamin K, cytochrome B5, a nucleic acid coding for gamma-glutamyl-carboxylase, for microsomal epoxidehydrolase, for calumenin, or for glutathion-S-transferase. Methods for introducing nucleic acids into host cells have been described in detail above. Preferably the nucleic acids are expressed under the control of a constitutively active promoter or a promoter which can be specifically activated in the host cell chosen.

The methods of identifying a coumarin derivative are useful for developing novel coumarin derivatives that avoid at least one of the limitations of coumarin and its derivatives known in the art. If analysis of the kinetics of blood coagulation is included as a separate assay into the determination of VKORC1 polypeptide activity, the method according to the invention may be useful in identifying coumarin derivatives which mediate blood coagulation faster than coumarin and its derivatives known in the art and/or that are metabolized more rapidly so that accumulation of coumarin and its derivatives may be prevented or ameliorated and as a result the danger of overdosing is substantially decreased or even abolished. Moreover, such method of identifying may be combined with other assays such that coumarin derivatives may be identified which have a stronger (weaker) effect onto VKORC1 activity and thus in turn onto the blood coagulation and which coumarin derivatives in independent assays prove (1) to be metabolized more rapidly so that accumulation of coumarin may be prevented or ameliorated and as a result the danger of overdosing is substantially decreased or even abolished, (2) not to cause or to cause to lesser extend skin necrosis in patients or embryopathy if applied during pregnancy, and/or (3) to be metabolized faster or to be less more stabil and/or to be affected less by other drugs like Phenobarbital or amiodarone. The assays which are suitable to screen for such properties of the coumarin derivatives and which are to be combined into a screen with the method of identifying a coumarin derivative according to the invention are generally known to the person skilled in the art.

The term "coumarin" is understood as meaning 3-(acetonylbenzyl)-4-hydroxycoumarin, i.e. COUMADIN® or sodium warfarin.

The term "derivative of coumarin" is understood to encompass organic or inorganic compounds, peptides, polypeptides or complexes thereof, provided that they exert an effect onto the activity and/or expression of VKORC1 polypeptide, preferably an effect that inhibits the activity of the VKORC1 polypeptide, even more preferably a VKORC1 polypeptide-specific effect, i.e the coumarin derivative does not directly interact with other molecules involved in the coagulation pathway. Examples of such compounds are organic molecules that are derived from libraries of compounds, preferably those that have been analyzed for their pharmacological activity. On account of their interaction, the derivatives of coumarin can influence the activity of the VKORC1 polypeptide in vivo and/or in vitro and enter into interactions of covalent or non-covalent manner with them. If the coumarin derivative is a chiral compound it is understood that "derivative of coumarin" also encompasses the respective R- and L-enantiomeril forms of the compound like those disclosed in WO 00/43003. In particular the term "derivative of coumarin" refers to compounds derived from 4-hydroxycoumarin, especially compounds derived from COUMADIN. More preferably, "derivative of coumarin" also includes any coagulants which inhibits the regeneration of active vitamin K.

The term "candidate coumarin derivative" is understood to encompass organic or inorganic compounds, peptides, polypeptides or complexes. Examples of such compounds are organic molecules that are derived from libraries of compounds, preferably those that have been analyzed for their pharmacological activity. Preferably the term refers to compounds that are structurally related or derived from 4-hydroxycoumarin, especially compounds related or derived from COUMADIN. If the candidate coumarin derivative is a chiral compound it is understood that the respective R- and L-enantiomeric forms of the compound like those disclosed in WO 00/43003 are also encompassed by the term "candidate coumarin derivative".

In another aspect the present invention provides a method of determining a VKORC1 polypeptide sequence which conveys a coumarin effect exerted onto VKORC1 activity, comprising the steps of:
(I) providing a cell expressing the VKORC1 polypeptide according to the invention, preferably a polypeptide according to SEQ ID NO. 1, 12, 17, 21, 25, and 27, which VKORC1 polypeptide has at least one sequence abnormality, preferably a sequence abnormality selected from the group consisting of V29L, V45A, R58G, R98W, L128R and Y139C;
(II) administering coumarin or a derivative thereof to the cell;
(III) determining the activity of the VKORC1 polypeptide (sequence abnormality activity value); and
(IV) comparing the sequence abnormality activity value with the control sequence activity value,
wherein a significant deviation of the sequence abnormality activity value from the control sequence activity value is indicative that the sequence abnormality of the VKORC1 polypeptide conveys the coumarin effect exerted onto VKORC1 polypeptide. The activity of the VKORC1 polypeptide may be determined as described in detail above.

More preferably, in the method of determining a VKORC1 polypeptide sequence the control sequence activity value is determined by a method comprising the steps of:
(I) providing a cell expressing the VKORC1 polypeptide, preferably a polypeptide according to SEQ ID NO. 1, 12, 17, 21, 25, and 27;
(II) administering coumarin or a derivative thereof to the cell;
(III) determining the activity of the VKORC1 polypeptide (control sequence activity value).

The determined VKORC1 activity is dithiothreitol-dependent conversion of vitamin K 2,3-epoxide to vitamin K quinone and the significantly different value is a sequence abnormality activity value which is significantly higher than the control sequence activity value. Further details are provided above and in Example 7 and FIG. 10. The method may be useful in identifying VKORC1 polypeptides that are less sensitive to coumarins. By introducing VKORC1 polypeptides with different sequence abnormalities this method allows identification of sites of the polypeptide which are critical for the interaction of a tested coumarin and VKORC1. Such knowledge will for example be useful for designing new coumarins.

It is particularly preferred in the method of determining a VKORC1 polypeptide sequence that at least one additional compound is introduced into the cell which compound is selected from the group consisting of vitamin K, cytochrome B5, and a nucleic acid coding for gamma-glutamyl-carboxylase, for microsomal epoxidehydrolase, for calumenin, or for glutathion-S-transferase.

A further aspect of the present invention relates to a VKORC1 polypeptide as defined above, preferably to the VKORC1 polypeptide according to SEQ ID No. 1, wherein the VKORC1 polypeptide contains at least one sequence abnormality, which exerts an effect on the activity of the VKORC1 polypeptide. More preferably the VKORC1 polypeptide is the polypeptide according to SEQ ID No. 1 and the sequence abnormality is selected from the group consisting of V29L, V45A, R58G, R98W, L128R and Y139C. In another embodiment, the invention relates to the *Rattus norvegicus* VKORC1 polypeptide according to SEQ ID No. 12 having a sequence abnormality, preferably the sequence abnormality Y139C (416A>G). In another embodiment the invention relates to a *Rattus norvegicus* nucleic acid encoding the *Rattus norvegicus* VKORC1 polypeptide according to SEQ ID No. 12 having a sequence abnormality, preferably the VKORC1 nucleic acid according to SEQ ID No. 12 having a sequence abnormality, preferably the 416A>G sequence abnormality. The nucleic acid VKORC1 sequence containing the abnormality is 416A>G is the nucleic acid sequence according to SEQ ID No. 14.

Such VKORC1 polypeptide containing at least one sequence abnormality can be generated by methods generally known to the skilled worker, including recombinant techniques and e.g. site directed mutagenesis, or by isolation the VKORC1 polypeptide having the at least one sequence abnormality from a sample obtained from a patient, preferably from a patient suffering from VKORC1 associated deficiencies. Methods for isolating proteins from a sample have been described in detail above.

The VKORC1 polypeptide containing at least one sequence abnormality, which exerts an effect on the activity of the VKORC1 polypeptide can, for example, be used for generating antibodies binding specifically to these VKORC1 polypeptides. These antibodies in turn can be utilized for diagnosing VKORC1 associated deficiencies.

The term "sequence abnormality" is meant to encompass additions, insertions, deletions, substitutions of at least one amino acid that result in an alteration of the VKORC1 polypeptide sequence, preferably of the VKORC1 polypeptide sequence according to SE ID No. 1. Also encompassed are additions, insertions, deletions, substitutions of at least one nucleotide that lead to an altered amino acid sequence encoded by the VKORC1 nucleic acid sequence. Also encompassed are changes of the VKORC1 nucleic acid sequence that lead to a change in the reading frame of the nucleic acid sequence.

The sequence abnormalities are indicated in the single letter amino acid code with the original amino acid being placed to the left of the number indicating the number of the amino acid in the polypeptide sequence according to SEQ ID No. 1. The number to the right of the amino acid number indicates the amino acid that replaces the original amino acid. For example, the sequence abnormality V29L indicates that in position 29 of the VKORC1 polypeptide of SEQ ID No. 1 the amino acid valine (V) has been replaced by leucine (L). In case the sequence abnormality occurs in a VKORC1 polypeptide other than the VKORC1 polypeptide of SEQ ID No. 1 the number in the code refers to the sequence position according to the numbering of the amino acids in that particular other polypeptide.

In another aspect the present invention provides a VKORC1 nucleic acid selected from the group consisting of:

(a) a nucleic acid coding for the VKORC1 polypeptide containing at least one sequence abnormality, which exerts an effect on the activity of the VKORC1 polypeptide, wherein the VKORC1 polypeptide is preferably the polypeptide according to SEQ ID No. 1 and the sequence abnormality is selected from the group consisting of V29L, V45A, R58G, R98W, L128R and Y139C;

(b) a nucleic acid sequence selected from the group consisting of a sequence according to SEQ ID No. 3, 4, 5, 6, and 7, 14, and 94; and (c) a nucleic acid sequence which, but for the degeneracy of the genetic code, would hybridize to the nucleic acid defined in (a) or (b) and which nucleic acid sequence codes for the polypeptide containing at least one sequence abnormality as defined above.

These nucleic acids are for example useful for isolating VKORC1 polypeptides and nucleic acids having such sequence abnormality, for producing DNA and/or RNA probes, for producing antibodies, for the construction of transgenic animals and knock-out animals, and for inclusion into screens for identifying coumarin derivatives.

In a further aspect the present invention provides a vector containing the VKORC1 nucleic acid containing at least one sequence abnormality as defined above. Such vectors may be selected from the vectors described in detail above. The methods for constructing such vectors are also described in detail above. Such vectors are for example useful for preparing probes described in the next paragraph, especially in a diagnostic context.

In another aspect of the present invention there is provided a DNA or a RNA probe directed against VKORC1 nucleic acid containing at least one sequence abnormality as defined above, preferably a nucleic acid sequence according to SEQ ID No. 3, 4, 5, 6, and 7, 14, and 94. Methods of designing and producing such DNA and RNA probes have been described to a great extend above. Such probes are useful for example for detecting sequence abnormalities in the VKORC1 gene in a gene library, in an expression library, or in a sample isolated from a patient, for example in the context of diagnosis of VKORC1 associated deficiencies and for site directed mutagenesis for producing VKORC1 nucleic acids containing a sequence abnormality. Techniques for screening libraries are generally known to the skilled worker.

In another aspect of the present invention there is provided a PCR primer directed against VKORC1 nucleic acid containing at least one sequence abnormality as defined above. Preferred PCR primers for detecting the Y139C (416A>G) sequence abnormality are the primers according to SEQ ID No. 88 to 91 (see Example 9). It is generally known to the person skilled in the art to design the PCR primers such that they may be used for detecting other sequence abnormalities such as those mentioned above (V29L, V45A, R58G, R98W, L128R) for the purpose of the invention. Methods of designing and producing such PCR primers, techniques to carry out PCR amplification have been described to a great extend above, the major difference being that the primers have to be designed such that only those VKORC1 nucleic acid sequences containing the sequence abnormality are specifically amplified, whereas native VKORC1 nucleic acids and other VKORC1 nucleic acid sequences that do not contain the sequence abnormality, such as the VKORC1 nucleic acid of SEQ ID No. 2 remains undetected. Such primers are useful for example for detecting sequence abnormalities in the VKORC1 gene in a gene library, in an expression library, or in a sample isolated from a patient, for example in the context of diagnosis of VKORC1 associated deficiencies. Techniques for screening libraries are generally known to the skilled worker.

In a further aspect the present invention relates to an antibody which specifically recognizes and binds the VKORC1 polypeptide containing at least one sequence abnormality as defined above, the VKORC1 polypeptide preferably being the polypeptide according to SEQ ID No. 1 and the sequence abnormality being selected from the group consisting of V29L, V45A, R58G, R98W, L128R, and Y139C, or a fragment of the antibody. The types of antibodies encompassed, methods of constructing and producing such antibodies and fragments thereof have been described in great detail above. Such antibodies are e.g. useful for the detection and isolation of VKORC1 polypeptide containing at least one sequence abnormality as defined above, especially in the context of diagnosis of VKORC1 associated deficiencies and for detection of Warfarine resistance in humans and rodents such as rats.

According to another aspect the present invention relates to a diagnostic comprising a compound selected from the group consisting of the VKORC1 nucleic acid containing at least one sequence abnormality, preferably at least one sequence abnormality selected from V29L, V45A, R58G, R98W, L128R, and Y139C; the DNA or the RNA probe directed against the VKORC1 nucleic acid containing at least one sequence abnormality, the PCR primer directed against the VKORC1 nucleic acid containing at least one sequence abnormality, and an antibody directed against the VKORC1 polypeptide containing at least one sequence abnormality; all of which have been defined above. In the case the VKORC1 associated deficiency is due to or correlated with a sequence abnormality, it is the principle of the diagnostic to be used for detection of that sequence abnormality in a probe obtained from a patient. The suitable methods for using the diagnostic according to the invention are mentioned below. Optionally the diagnostic further comprises a pharmaceutically acceptable additive and/or auxiliary. Such diagnostic is useful for diagnosing VKORC1 associated deficiencies especially warfarin resistance.

In on the other hand the VKORC1 associated deficiency is to be diagnosed based on the detection of the level of expression of VKORC1 mRNA, VKORC1 cDNA or VKORC1 polypeptide in the sample, such levels of expression can be determined by methods generally known to the person skilled in the art. Examples of such methods for detecting the presence of a VKORC1 mRNA include RNA blot (Northern) analysis, nuclease protection, in situ hybridization, reverse transcriptase PCR (RT-PCR; including quantitative kinetic RT-PCR). cDNA and oligonucleotide microarrays are also included as such methods. An expression library derived from a patient may as well be screened for the purpose of diagnosis using techniques generally known to the skilled worker. The presence of VKORC1 polypeptide can also be determined by methods generally known to the skilled worker, some of which are described below. Optionally the diagnostic further comprises a pharmaceutically acceptable additive and/or auxiliary.

Within the meaning of the present invention "additive" and "auxiliary" are not particularly limited and generally known to the person skilled in the art and comprise, for example, physiological saline solution, demineralized water, gelatin or glycerol-based protein stabilizing reagents. Alternatively, the VKORC1 nucleic acids, probes, primers or polypeptide according to the present invention may be lyophilized for stabilization.

In another aspect the invention provides a method of diagnosing a VKORC1 associated deficiency in a patient comprising the steps of:
(I) amplifying a DNA sample obtained from the patient or reverse transcribing a RNA sample obtained from the patient into a DNA and amplifying the DNA; and
(II) analyzing the amplified DNA of step (I) to determine at least one sequence abnormality in a nucleic acid sequence coding for the VKORC1 polypeptide or in an amino acid sequence of the VKORC1 polypeptide;
wherein the determined sequence abnormality is indicative of the patient suffering from a VKORC1 associated deficiency; preferably Warfarine resistance; preferably the sequence abnormality exerts an effect on the activity of the VKORC1 polypeptide, preferably the sequence abnormality is selected from V29L, V45A, R58G, R98W, L128R, and Y139C.

Methods for obtaining samples from a patient and for isolating total RNA or mRNA are generally known to the skilled worker, some of which have been described above. Techniques for amplifying of DNA are not particularly limited and include PCR techniques which have also been described above. By the same token, techniques for reverse transcribing have been mentioned above and are not particularly limited and include reverse transcription using conventional protocols and commercially available kits that usually employ reverse transcriptase and oligo dT primers. The analysis may as well be based on genomic DNA isolated from a sample obtained from a patient.

Upon amplification, the DNA is subjected to analysis in order to determine at least one sequence abnormality in a nucleic acid sequence coding for the VKORC1 polypeptide. Methods for analyzing the amplified DNA are not particularly limited. Preferably the amplified DNA is analyzed by a technique selected from the group consisting of PCR-based analysis, preferentially using PCR primers specific for the sequence abnormality, restriction digestion analysis, and DNA sequencing analysis. In a preferred embodiment the nucleic acid carrying the sequence abnormality is coding for a VKORC1 sequence having a sequence abnormality is selected from the group consisting of V29L (85 G>T), V45A (134 T>C), R58G (172 A>G), R98W (292 C>T), and L128R (383 T>G), Y139C (416 A>G). In a preferred embodiment of the method of diagnosing the amplified DNA encodes at least a partial sequence of the VKORC1 polypeptide according to SEQ ID No. 1. One way of determining a sequence abnormality which is associated with a VKORC1 associated deficiency is provided in Example 8.

The VKORC1 sequences according to the invention containing the mutations 85 G>T, 134 T>C, 172 A>G, 292 C>T, and 383 T>G, are provided in SEQ ID Nos. 3 to 7 and may be used as probes for diagnosing a VKORC1 associated deficiency using hybridization technique based analysis of nucleic acid samples obtained from a patient.

As an alternative VKORC1 expression may be detected on the level of the VKORC1 polypeptide. Therefore, in another aspect the present invention provides a method of diagnosing a VKORC1 associated deficiency in a patient comprising the steps of:
(I) providing a sample obtained from the patient; and
(II) detecting a VKORC1 polypeptide having a sequence abnormality in the sample using the antibody directed against the VKORC1 polypeptide having a sequence abnormality as defined above,
wherein the determined sequence abnormality is indicative of the patient suffering from a VKORC1 associated deficiency.

Preferably the sequence abnormality is selected from the group consisting of V29L, V45A, R58G, R98W, L128R, and Y139C.

Methods for obtaining samples have been described in detail already. Methods for detection of VKORC1 polypeptide having a sequence abnormality are not particularly limited, provided that the method allows specific detection of the protein carrying the sequence abnormality(ies). Examples of such methods preferably include immunohistochemical detection, immunoblotting, preferably Western blotting, and ELISA of the polypeptide, particularly preferred with antibodies specific for the VKORC1 polypeptide having a sequence abnormality as defined above. Analysis of sequence abnormalities on the level of the amino acid sequence is not particularly limited and may for example be carried out using VKROP1 antibodies which specifically recognize and bind a VKORC1 polypeptide having one or more sequence abnormalities.

Preferably the methods of diagnosing are used for diagnosing diseases and/or disorder selected from warfarin resistance, familial multiple factor deficiency, a disorder or disease associated with reduced or abolished blood coagulation, such as hemophilia and a disorder associated with decreased vascular calcification, diseases and/or disorders associated with impaired gamma-carboxylation of vitamin K dependant proteins.

Moreover, the methods of diagnosing may also be used to diagnose disorders and diseases associated with increased blood coagulation including patients and/or patients having an increased risk of developing a thrombus due to a sequence abnormality in the VKORC1 polypeptide or its gene, diseases and/or disorders associated with improved gamma-carboxylation of vitamin K dependant proteins.

In another aspect the present invention provides a method of identifying a coumarin derivative which exerts an inhibitory effect onto the activity of a VKORC1 polypeptide having at least one sequence abnormality, comprising the steps of:

(I) providing a cell expressing the VKORC1 polypeptide, preferably a polypeptide encoded by a sequence selected from the group consisting of 3, 4, 5, 6, 7, 14, and 94;
(II) administering a candidate coumarin derivative to the cell;
(III) determining the activity of the VKORC1 polypeptide (sequence abnormality activity value); and
(IV) comparing the sequence abnormality activity value with the control sequence activity value,
(V) identifying the candidate coumarin derivative as the coumarin derivative exerting an inhibitory effect onto the activity of a VKORC1 polypeptide, if the administration of the candidate coumarin derivative results in a sequence abnormality activity value which is significantly lower than the control sequence activity value.

More preferably, the control sequence activity value is determined by a method comprising the steps of:

(I) providing a cell expressing the VKORC1 polypeptide of claim 1, preferably a polypeptide according to SEQ ID No. 1 or 12;
(II) administering coumarin to the cell;
(III) determining the activity of the VKORC1 polypeptide (control sequence activity value).

The activity of the VKORC1 polypeptide may be determined as described in detail above. And the method may be adopted from the method described in Example 7. Such method of identifying a coumarin derivative is useful for identifying coumarin derivatives that can be used as anticoagulants in warfarin resistance patients.

In another aspect the present invention provides a method of identifying a coumarin derivative which is toxicologically effective in warfarin-resistant rodents comprising the steps of:

(I) providing a warfarin-resistant rodent;
(II) administering a candidate coumarin derivative to the rodent;
(III) determining the toxicity of the candidate coumarin derivative onto the rodent (candidate coumarin derivative toxicity value);
(IV) comparing the candidate coumarin derivative toxicity value with a control coumarin toxicity value; and
(V) identifying the candidate coumarin derivative as a toxicologically effective coumarin derivative, provided that the candidate coumarin derivative toxicity value is significantly larger than the control coumarin toxicity value.

Preferably, the warfarin-resistant rodent is a rodent transgenic for VKORC1 polypeptide as defined above, wherein the VKORC1 polypeptide contains at least one sequence abnormality, which causes warfarin resistance, preferably a polypeptide encoded by the sequence according to SEQ ID No.14 or a commercially available Warfarine resistant rat or a wild catch rat having Warfarine resistance. More preferably, the VKORC1 polypeptide is the polypeptide according to SEQ ID No. 12 and the sequence abnormality is selected from the group consisting of V29L (85 G>T), V45A (134 T>C), R58G (172 A>G), R98W (292 C>T), and L128R (383 T>G), and Y139C (416 A>G).

The sample can be any organ, tissue, body fluid or probe provided that it contains genomic DNA or mRNA from the rat to be tested. Preferably the sample is blood, tissue from tail or ear urine or feces. Further details of the method are provided in Example 9.

Warfarin-resistant rodents have been described (Kohn & Pelz, 1999) and may be obtained from commercial suppliers (e.g. The Federal Biological Research Center for Agriculture and Forestry, Institute for Nematology and Vertebrate Research, Toppheideweg 88, 48161 Münster, Germany). In a preferred embodiment the warfarin-resistant rodent is a rodent transgenic for VKORC1 polypeptide containing at least one sequence abnormality, which sequence abnormality causes warfarin resistance. More preferred, the VKORC1 polypeptide containing at least one sequence abnormality is the polypeptide encoded by the nucleic acid sequence according to SEQ ID Nos. 3 to 7, and 15, and the sequence abnormality is selected from the group consisting of V29L (85 G>T), V45A (134 T>C), R58G (172 A>G), R98W (292 C>T), and L128R (383 T>G), Y139C (416 A>G). Methods for generating rodent, in particular mice transgenic for the recited VKORC1 polypeptides have been described above.

According to another aspect the invention relates to the use of PCR primers according to SEQ ID No. 88 to 91 for determining whether or not a rat has a warfarin resistance genotype in a sample obtained from a rat.

The administration of coumarin and its derivatives is not particularly limited. Typically coumarin (warfarin)-containing toxicologically effective compositions are formulated as granular bait compositions containing from about 50-300 ppm, preferably about 250 ppm, of coumarin and its derivatives. The bait is typically formulated with from 0.5% to 2.5% of warfarin concentrate in a suitable binder such as corn oil. If corn oil is used as a binder, it can be present in an amount of from about 0.5% to about 2% of the total composition. The binder and warfarin are then mixed in e.g. with a product based on cereal products, corn meal, rolled oats, mixed animal feeds, and similar products known in the art. The administration, i.e. the amount, formulation and frequency and duration of administration may follow standard protocols for assessing the toxicity of warfarin in rodents, more preferred follow standard protocols for assessing the lethal dose 50 ($LD_{50}$) value for a given poison to be tested, all of which are generally known to the skilled person and described in example 9

In order for the coumarin derivative to be toxicologically effective it is desirable that multiple ingestions are required to kill the rodent so that they do not develop bait shyness. Therefore, it is preferred to repeat the administration of the candidate coumarin derivative compositions a number of times. Usually the rodents begin to die after four or five daily doses of the compositions. Moreover, it may be preferred to suppress pain in the rats in order to ameliorate the suffering during the experiments by administration of pain suppressing agents generally known to the skilled worker. Inclusion of pain-suppressors in the coumarin and coumarin derivative composition may further be advantageous in order to further suppress the chance that rodents develop bait shyness.

Following administration the toxicity of the candidate coumarin derivative onto the rodent is determined which yields the candidate coumarin derivative toxicity value. Methods for determining the toxicity of candidate coumarin derivatives are generally known to the skilled worker and include $LD_{50}$ analysis, analysis of the blood coagulation by determining the prothrombin time, e.g. by international normalized ration (INR) protocol. The determined candidate coumarin derivative toxicity value is then compared with an appropriate control coumarin toxicity value determined on the basis of subjecting a different specimen of the warfarin-resistant rodent to the same treatment but exchanging the coumarin derivative administration with an administration of a standard rodent coumarin composition which the rodents are resistant for, commonly used for pest control. The same experimental conditions described above for the candidate coumarin derivative administration are used for the control. If the candidate coumarin derivative toxicity value is equal or preferably statistical significantly larger than the control coumarin toxicity value, the candidate coumarin derivative represents a toxicologically effective coumarin derivative.

In another aspect of the invention the invention provides a composition for killing rodents, comprising a toxicologically effective amount of the coumarin derivatives identified by the method described above. The formulation of bait compositions containing coumarin and its coumarin derivative have been described above. A typical formulation has the following constituents: Ingredient %: Grain carrier 94%, Corn oil 1.0%, coumarin or coumarin derivative concentrate (0.5%) 5.0; total 100.0%.

The invention further relates to the following embodiments: A coagulant pharmaceutical composition comprising a compound selected from the group consisting of the VKORC1 polypeptide, the VKORC1 nucleic acid, the fusion protein according to the invention, the vector according to the invention, the host cell according to the invention, optionally combined with a pharmaceutically acceptable carrier.

A method of treating a patient in need of such treatment comprising the step of administering to the patient a therapeutically effective amount of the coagulant pharmaceutical composition. The method can be used for treating a patient suffering from a VKORC1 associated deficiency.

An anticoagulant pharmaceutical composition comprising a compound selected from the group consisting of the siRNA and/or shRNA according to the invention, the antisense RNA or DNA according to the invention, the RNA-aptamere according to the invention, the antibody according to the invention, optionally combined with a pharmaceutically acceptable carrier.

A method of treating a patient in need or such treatment comprising the step of administering to the patient a therapeutically effective amount of the anticoagulant pharmaceutical composition.

The use of a VKORC1 polypeptide or a VKORC1 nucleic acid for gamma-carboxylating vitamin-K dependant polypeptides. Preferably the gamma-carboxylated vitamin-K dependant polypeptide is a polypeptide selected from the group consisting of blood coagulation factor II, VII, IX, X, protein C, protein S, protein Z, matrix gla protein, and osteocalcin. In a preferred embodiment the VKORC1 is used in combination with at least one additional compound preferably in a cellular setting, which additional compound is selected from the group consisting of vitamin K, cytochrome B5, and a nucleic acid coding for gamma-glutamyl-carboxylase, for microsomal epoxidehydrolase, for calumenin, or for glutathion-S-transferase.

The invention will now be further illustrated below with the aid of the figures and examples, representing preferred embodiments and features of the invention without the invention being restricted thereto.

EXAMPLES

Example 1

Characterization of the Genomic Candidate Region

Figure 1:
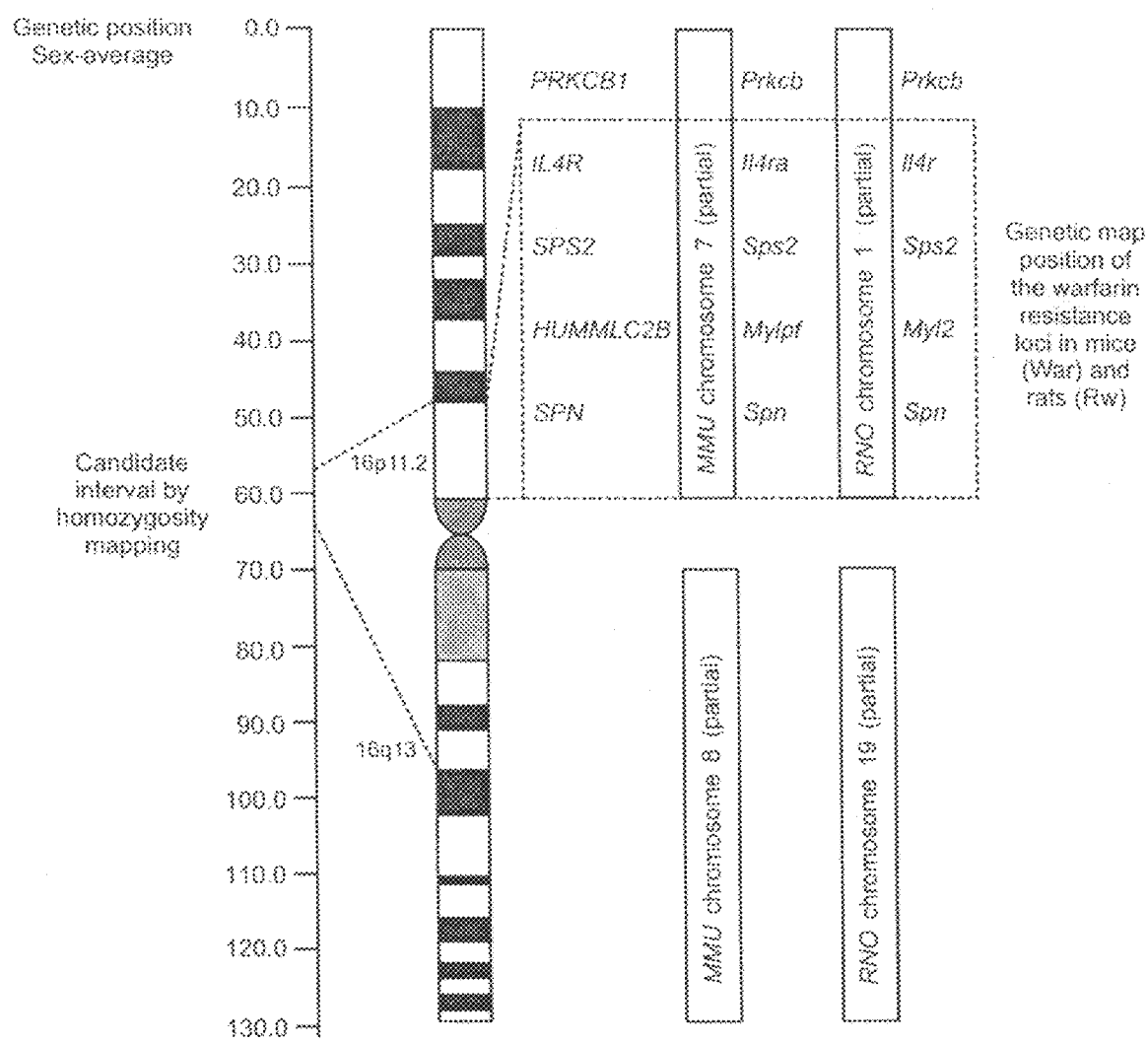
FIG. 1 depicts a comparison of the candidate interval of 3 cM in the genetic map containing the VKORC1 gene locus in human, rat and mouse. The ideogram of human chromosome 16 is shown, the area of homozygosity in the families 1 and 2 extends from 16p11.2 to 16q13 corresponding to approximately 25 Mb. In the right part of the figure there are homologous parts of mouse and rat-chromosomes. Synthenic genes of 16p11.2 and 16q12.1 with homologous counterparts in *Mus musculus* (MMU) and *Rattus norvegicus* (RNO) are depicted. The loci for phenotype resistance to warfarin in the mouse (War) and rat (Rw) are mapped to regions homologous to 16p11.2. MMU: *Mus musculus*; RNO: *Rattus norvegicus*; PRKCB1; Prkcb; IL4R: Interleukin4 receptor α (human); Il4ra: Interleukin4 receptor α (murin); Il4r: Interleukin4 receptor α (rat); SPS2: Selenophosphate synthetase (human); Sps2: Selenophosphate synthetase (murin/rat); HUMMLC2B: Myosin light Chain2 (human); Mylpf: Myosin light chain 2 (murin); Myl2: Myosin light chaun 2 (rat); SPN: Sialophorine (human); Spn: Sialophorine (murin/rat).

The locus for combined deficiency of vitamin K-dependent clotting factor type 2 (VKCFD2) to the pericentromeric region of chromosome 16 between the markers D16S3131 and D16S419 has been mapped [Fregin et al., 2002]. This region comprises approximately 20 Mb. The genes responsible for warfarin resistance in rats (Rw) and mice (War) had been mapped to chromosome 1 [Kohn et al., 1999] and chromosome 7 [Wallace, 1976] [Greavses & Ayres, 1967] in close linkage to the myosin light chain 2 gene (Myl2). The human ortholog of Myl2, HUMMLC2B, is located on chromosome 16p11 within the VKCFD2 candidate region and is part of a conserved linkage group of genes. Based on this synteny and on biochemical considerations, it is hypothesized that VKCFD2 and warfarin resistance may be due to allelic mutations in the same gene. If so, this would narrow down the critical interval in humans to a region of approximately 4.5 Mb between the interleukin 4 receptor gene (IL4R) and the integrin alpha M chain gene (ITGAM) on the short arm of chromosome 16 (FIG. 1).

According to the genome assembly, this region contains 141 Ensembl genes with approximately 1000 exons. Of these genes, 117 were annotated as known. Many of these genes could be excluded from further analysis because their function was well established and obviously not related to the metabolic steps of the vitamin K cycle. On the other side, genes upstream and downstream of this region are included that were regarded as functional candidates into the mutation screen.

Example 2

Mutation Screening

Using genomic DNA from two VKCFD2 and three WR subjects, a systematic mutation screen was initiated by comparative sequencing of the remaining candidate genes. Clinical data of the VKCFD2 families have been described previously [Oldenburg et al., 2000]. Warfarin resistant patients were ascertained due to their abnormal response to oral warfarin administration during thrombosis treatment or prevention. Patient C and E are sporadic cases. Patient D has two brothers also suffering from warfarin resistance. Patients C and D required approximately 150-250 mg warfarin per week to achieve a therapeutic range of oral anticoagulation whereas patient E did not show any response at all. All patients gave informed consent before participating.

Figure 2:
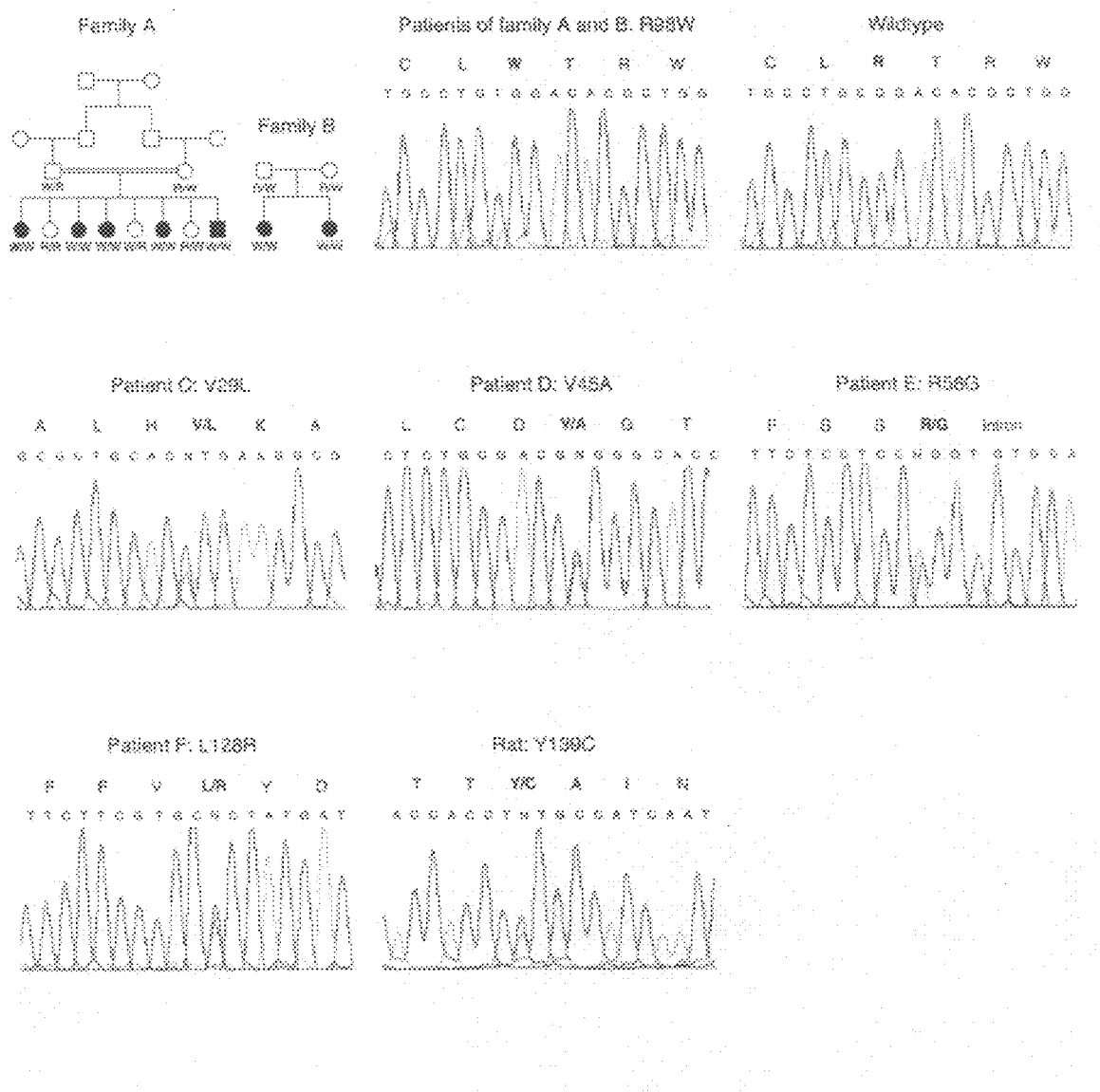
FIG. 2 displays VKORC1 mutations in human vitamin K dependent clotting factor 2 (VKCFD2) and warfarin resistance (WR) patients. The upper part of the figure shows the segregation of the R98W mutation in two VKCFD2 families and the electropherograms of a homozygous mutant (left) compared to a control (right). The bottom part of the figure shows the heterozygous mutations of four WR patients. (85G>T, 134T>C, 172A>G, 383T>G) and a Rw rat (416A>G).

Surprisingly, missense mutations were found in a gene of unknown function in all investigated VKCFD2 and WR subjects (FIG. 2). This gene (IMAGE3455200) spans a genomic region of 5126 bp and comprises three exons coding for a protein of 163 amino acids. It was named vitamin K epoxide recycling protein 1 (VKORC1). Both non-related VKCFD2 patients and their affected siblings were found to harbor the same homozygous point mutation in the third exon (292C>T) whereas the parents were found to be heterozygous. The mutation is caused by the replacement of arginine by tryptophan at amino acid residue 98 (R98W). The families are of German and Lebanese origin. The haplotypes in the region of homozygosity around the mutated gene were different in both families indicating independent mutation events. In the WR patients, three different heterozygous mutations were found leading to a valine by leucine substitution (patient C: V29L), an arginine by glycine substitution (patient D: R58G) and an exchange of leucine to arginine (patient E: L128R). The R58G mutation is shared by the two affected brothers of index patient D. The missense mutations were not present in 384 control chromosomes. Sequencing of the control chromosomes revealed two non-synonymous single nucleotide polymorphisms (C43C; L120L).

Genome sequences and annotation were obtained from NCBI, UCSC and Ensembl. Primers for mutation screening were designed using Primer3 software integrated into a script, ExonPrimer, to allow automatic primer design. For mutation screening, exons with intronic primers were amplified and amplified fragments were analyzed by direct sequencing with the BigDye Terminator Cycle sequencing kit (ABI)). Primer sequences were available on request. Topology predictions were performed using TMPRED and TMHM.

Example 3

Homology and Protein Structure

An orthologue of the VKORC1 gene was present in mouse (NM_178600) and the orthologues in rat and in *Fugu rubripes* were established by homology searches and RT-PCR (FIG. 3). The corresponding proteins share 79% to 84% identity with the human protein. Database searches did not show any homology to a known gene nor to any characterized protein domain. Topology prediction programs anticipated three transmembrane domains (TM). The first TM is placed between residues 10 to 29 by all programs tested. The predictions are discordant for the second and the third TM, which are located between amino acids 100 and 150. The PSORT II server predicted an ER membrane retention signal (KKXX or KXKXX) at position 159-163 of human VKORC1 with a probability of 67%[Jackson et al., 1990]. The consensus sequence was also present in the other VKORC1 proteins. This is in accordance with the likely location of the VKORC1 complex within the ER membrane system [Cain et al., 1997].

Tblastn searches with VKORC1 detected a homologous human (BC027734) and mouse gene (AK009497) showing 50% protein identity each. Both mRNA were wrongly predicted to code for proteins that show no homology with VKORC1. The predicted human protein starts at the third methionine. The mouse mRNA sequence is incomplete with a protein predicted in a different reading frame. The complete cDNA was established in mouse as well as in *Fugu rubripes* and partially in rat. These proteins were designated VKORC1 like protein 1 (VKORC1L1). Human, mouse and rat VKORC1 L1 proteins share approximately 84% identity between each other and approximately 50% identity with the corresponding VKORC1 proteins. A homologous protein was further detected in *Xenopus laevis* (AAH43742) and—with weaker homology (1e-14)—in *Anopheles gambiae* (EAA06271). Tree analysis suggested that both these proteins are orthologues to the VKORC1 gene.

Example 4

Expression Analysis

VKORC1 seems to be widely expressed. The corresponding Unigene entry contains more than 100 ESTs in various tissues. The expression of VKORC1 in fetal and adult human tissues is examined by Northern blot analysis. To this end Human multiple tissue northern blots (Fetal Blot 1, Stratagene; Human 12-Lane, BD Clontech) contained 2 µg of poly(A)+-RNA. Full-length human VKORC1 cDNA was radiolabeled using random primers DNA labeling system (Invitrogen life technologies). and hybridized using miracle-Hyb High-Performance Hybridization Solution (Stratagene). A β-actin probe supplied with the multiple tissue northern blot was used for control hybridization.

Figure 4:
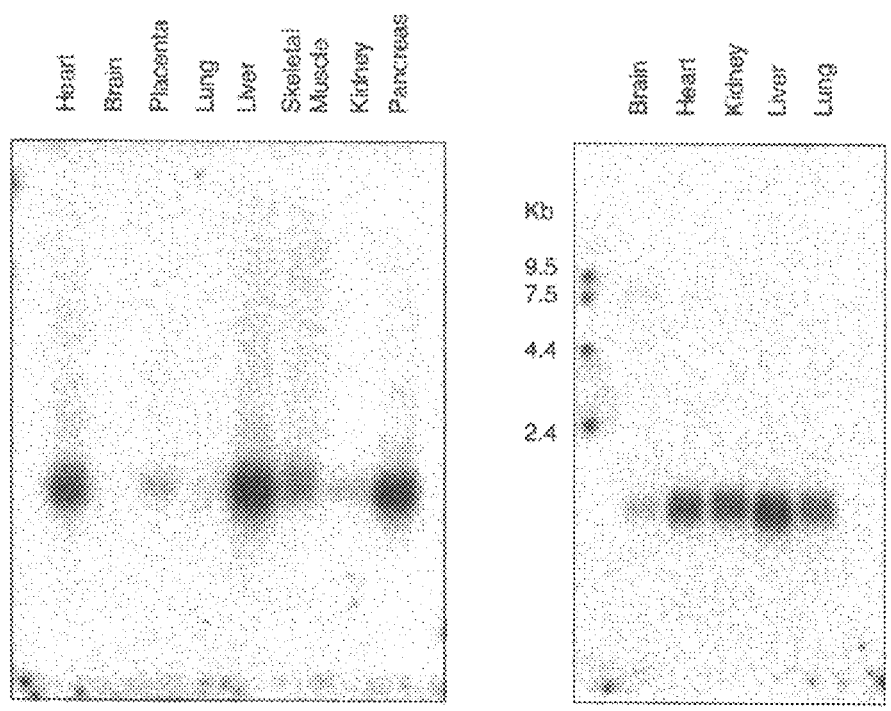
FIG. 4 displays a northern blot analysis of VKORC1 in fetal and adult human tissues. The upper blot depicts a northern blot of adult tissue, whereas the lower blot depicts a northern blot of fetal tissue. For more details see Example 4. The lines with fragments of the sizes 2.4, 4.4, 7.5, UND 9.5 KB indicate molecular weight markers and allow estimation of the size of the all visible bands)

The highest VKORP expression levels can be observed in fetal and adult liver (FIG. 4). High expression levels were also observed in fetal heart, kidney and lung, as well as in adult heart and pancreas. Fetal brain, adult placenta and skeletal muscle showed intermediate levels of expression. Minor expression levels were detected in adult brain, lung and kidney.

Example 5

Cloning of VKORC1 and Construction of Expression Vectors

Amplification of the complete coding sequence of VKORC1 was performed from human liver and kidney cDNA (Marathon-Ready cDNA, BD Biosciences Clontech) with the following primers including cleavage sites for HindIII and EcoRI:

```
VKORC1-HindIII-F:
                                          (SEQ ID No. 53)
ATTAAGCTTCACCATGGGCAGCACCTGGGGGAGCCCT VKORC1-EcoRI-R:
                                          (SEQ ID No. 54)
ATTGAATTCCGTGCCTCTTAGCCTTGCCCTG.
```

The product was cloned into the pBluescript 11 vector (Stratagene) that was cleaved with the corresponding restriction enzymes and verified by direct sequencing. For immunocytochemistry experiments, the insert was re-cloned into the mammalian expression vectors pEGFP-N1 (BD Biosciences Clontech) and pcDNA3.1/myc-His (Invitrogen).

For expression studies, the VKORC1 cDNA was cloned into the pcDNA3 vector (Invitrogen) after amplification with the primers VKORC1-pcdna3-F: GGGCGGAAGCT-TGAGATAATGGGCA (SEQ ID No. 92) and VKORC1- pcdna3-R: GCTTGAATTCAGGGCTCAGTGC (SEQ ID No. 93). Mutagenesis was performed using the QuikChange mutagenesis Kit (Stratagene). Wildtype and mutated cDNAs were re-cloned for expression in pCEP4 (Invitrogen) using the HindIII and XhoI-sites. All constructs were verified by sequencing.

Example 6

Cell Culture, Transient Transfection and Immunocytochemistry and Subcellular Localization From biochemical fractionation experiments it is known that the VKORC1 activity purifies with the microsomal membrane fraction [Cain et al., 1997]. Furthermore, the gamma-glutamyl-carboxylase has been localized to the membrane of the endoplasmic reticulum by immunocytochemistry [Presnell, 2002 #31]. In order to study the subcellular localization of human VKORC1 GFP- and myc-epitope tagged VKORC1 fusion protein constructs were generated for transient transfection experiments of COS-7 cells. Primary antibodies against the epitope tags and fluorochrome labeled secondary antibodies were used to visualize the fusion proteins. An antibody against the ER-specific protein calnexin served as a control. To this end COS-7 cells (DSMZ, Braunschweig) were maintained in Dulbecco's modified eagle's medium with 10% fetal calf serum. Cells were plated on glass cover slips in six-well plates and after 18-24 h in culture transfected with the expression vector constructs using Effectene (QIAGEN) according to the manufacturer's specifications. After 48-60 h of further culturing, the cells were washed with PBS and fixed in 70% acetone/30% methanol at $-20°$ C. for 15 min. Following fixation, the cells were permeabilized in PBS, 0.1% Nonidet P-40 (SIGMA N-6507), and then blocked with PBS, 2% BSA and 0.1% NP-40 at 37° C. Primary antibodies, Living Colors A.v. (JI-8) (BD Biosciences Clontech), anti-myc antibody (Invitrogen), and anti-calnexin (SIGMA) were diluted (1:100) in the blocking solution and incubated for 45 min at 37° C. Cover slips were washed in PBS, 0.1% NP-40 for 30 min. The same incubation and washing procedures were used for the secondary antibodies, i.e. anti-mouse-IgG-FITC (SIGMA) and anti-rabbit-IgG F(ab')2 fragment-Cy3 (SIGMA). Cover slips were counterstained with DAPI (1:500) for 1 min, washed with deionized water, mounted on slides using Vectashield (Vector) and visualized using a Leica fluorescence microscope.

The green immunofluorescence of the VKORC1 fusion proteins decorated the mesh-like structures of the ER within the cytoplasm and perfectly co-localized with the label of the ER-marker calnexin (red) (FIG. 5).

Example 7

An Assay for Determining Enzymatic VKORC1 Activity

HEK293-EBNA cells (Invitrogen) were grown in MEM with 10% FCS. For each experiment, $6 \times 10^5$ cells were plated onto 94 mm Petri dishes. After 30 h at 37° C. and 5% $CO_2$, transfection (20 µg of DNA construct per dish) was performed using the calcium phosphate method. After 40 h at 35° C., 3% $CO_2$ transfected cells (nearly grown to confluence) were washed in PBS, harvested and lysed in 450 µl 0.25 mM imidazole, (pH=7.6), 0.5% CHAPS. Transfection efficiency was checked by sequencing of RT-PCR products of an aliquot of cells.

VKOR enzymatic activity was measured with 30 µl of the whole-cell extracts which were resuspended in 500 µl buffer A (0.25 mM imidazole, (pH=7.6), 0.5% CHAPS). Then 20 µl 125 mM DTT were added with one minute incubation. Then 5 µl 400 mM $CaCl_2$, and Warfarin in 10 µl DMSO (final concentration 0-80 µM) were added. The reaction was started by addition of 2 µl vitamin K2,3-epoxide (final concentration 5 µM) and incubated at 30° C. for one hour. Reaction was stopped by extraction of the substrate (Vitamin K2,3-epoxide) and the reaction products (Vitamin K-quinone and hydroquinone) using 1 ml 2-Propanol/Hexane (3:2, v/v); the organic supernatant was collected, dried and resolved in 50 µl methanol and analyzed with an HPLC at 254 nm. The vitamin K quinone was separated from the epoxide by HPLC on a reversed phase C-18 column. During the extraction procedure vitamin K hydroquinone was quantitatively oxidized to the quinone form. The output of the HPLC was analyzed automatically by calculating the area under the line of extinction of each peak. The percentage of conversion of substrate was estimated by setting the area of the residual substrate-peak (epoxide) plus the product-peak (quinone) as 100 percent. Measurements were run in duplicate and the activity is given as percent of substrate converted into quinone. Vitamin K 2,3-epoxide was prepared by oxidation of vitamin K quinone (Sigma-Aldrich) with $H_2O_2$. Warfarin (Sigma-Aldrich) was added in DMSO (<1 Vol %).

Dose-response to warfarin inhibition was measured at 5 to 80 µM final concentration (Walin & Martin 1985). Untransfected and mock-transfected cells showed a low basal activity which was warfarin sensitive. Overexpression of Wildtype VKORC1 resulted in a striking stimulation of VKOR activity. Production of vitamin K quinone was 14 to 21-fold increased compared to untreated and mock-transfected cells. The activity was inhibited by warfarin in a dose-dependent manner (FIG. 10).

We also determined VKOR activity after transfection with mutated VKORC1 constructs (FIG. 10). Recombinant expression of the R98W mutation observed in the two VKCFD2 families did only slightly increase VKOR activity in HEK293 cells. Spontaneous bleeding episodes and high serum levels of vitamin K epoxide in these patients suggest that the efficiency of vitamin K recycling is also drastically decreased in vivo (Oldenburg et al. 2000). The five WR mutations showed a reduced VKOR activity ranging from 5% in the L128R variant to 96% in the V29L mutation. Mutations V45A, R58G and Y139C displayed about 23%, 21% and 48% activity, respectively (Table 1). Reduced VKOR activity associated with higher vitamin K demand and death from spontaneous bleeding has been observed in heterozygous and homozygous Rw rats (Martin et al. 1979, Thijssen & Pelz 2001, Fasco et al. 1983b). Similarly, in our expression system which mimics homozygous conditions WR mutations led to a lower functional efficiency of the VKOR complex. Whereas at the phenotypic level all WR variants exhibited at least partial resistance towards the anticoagulation effect of warfarin, both Wildtype and mutant proteins were sensitive to warfarin in vitro. At concentrations above 20 µM, mutations V29L and Y139C retained higher VKOR activities than the Wildtype while in mutations V45A, R58G, L128R, VKOR activity fell below the detection limit (FIG. 10).

Example 8

A Method of Diagnosing a VKORC1 Sequence Abnormality

Genomic DNA of the specimen (human patient or mammal) is isolated according to standard procedures generally known to the skilled worker. The genomic DNA of the desired Exon (1-3) of VKORC1 is amplified by PCR using specific primers which can also be designed by the skilled artisan. The PCR-product is then purified using e.g. SAP/Exo (shrimp alkaline phosphatase and exonuclease) under standard conditions.

The purified DNA is then subjected to standard sequencing procedures such as: addition of 0.3 µl primer which is 10 pmol/µl (forward or reverse primer) to 1 µl of the purified PCR-product; followed by addition of 8 µl DTCS-Mix (Beckman-Coulter) and 10.7 µl water; followed by cycle sequencing at

| First delay | 96° C. | 60 sec | |
|---|---|---|---|
| Danaturation | 95° C. | 30 sec | 30 Cycles |
| Annealing | Primerspecific (55-60° C.) | 30 sec | |
| Elongation | 60° C. | 4 min | |

After the cycle sequencing purification by precipitation follows:
ad 2 µl 100 mM EDTA, 2 µl 5M NaOAc (pH 4.8), 1 µl Glycogen vortex
ad von 60 µl 95% ethanol, vortex
centrifugation at 13000 g (10 min)
remove supernatant
wash pellet with 180 µl 70% Ethanol
dry pellet
resolve pellet in 35 µl Sample Loading Solution (SLS)

Then the probes are pipetted on a microtiter plate overlaid with a drop of paraffin-oil. Then separation in the sequencer at 4.2 V for 60-120 min follows. The raw data is analyzed and the sequences are aligned with control sequences using the CEQ 2000 XL software (Version 4.3.9, Beckman Coulter). Differences between the control sequences (preferably the genomic VKORC1 nucleic acid sequence or its coding sequence according to SEQ ID NO. 2) and the sequenced DNA is indicative of the probes sequence to represent a VKORC1 nucleic acid containing a sequence abnormality.

Example 9

PCR-Based Assay for Determining Warfarin Resistance in Rats

In order to determine whether or not a rat (*Rattus norvegicus*) is warfarin resistant, i.e. whether the VKORC1 coding sequence according to SEQ ID No. 13 carries a mutation Y139C (416A>G), the following assay based on ARMS-PCR was employed using rat feces as a source of rat genomic DNA.

It is the principle of the assay to include into the PCR reaction (1) one PCR primer (rVKORC1-innerF) that specifically hybridizes to the DNA sequence which contains the warfarin resistant mutated allele 416G and (2) another PCR primer (rVKORC1-innerR) which specifically hybridizes to the Wildtype DNA sequence which contains the Wildtype allele 416A. Moreover, these two primers are oriented in opposite direction such that they pair with one out of two additional PCR primers included into the reaction. The latter primers are located in different distances to and in opposite direction relative to the 416 site and as a result, depending on whether the 416 site is mutated or not either the rVKORC1-innerR primer or the rVKORC1-innerF primer will anneal and the PCR reaction will result in amplified DNA of a different size which is indicative of the genotype of the rat which DNA has been analyzed. In Wildtype rats the PCR reaction will result in a band of 123 bp, whereas in rats homozygous to the mutation 416G the PCR reaction will yield a band at 101 bp. Finally in rats with a heterozygous genotype, the PCR reaction will give rise to two bands, one at 101 and another band at 123 bp.

The genomic DNA was isolated from the feces using standard DNA isolation procedures generally known to the skilled artisan. The following components were combined to a PCR reaction: 1 µl DNA (rat), 1 µl 5M Betain (Sigma), 2 pmol outer-Primer-F (1 µl of a 1:50-dilution), 2 pmol outer-Primer-R (1 µl of a 1:50-dilution), 10 pmol inner-Primer-F (1 µl of a 1:10-dilution), 10 pmol inner-Primer-R (1 µl of a 1:10-dilution), 0.25 µl Taq/Pfu-Polymerase (1.25 U Taq (Invitrogen) and 0.25 U Pfu (Stratagene)), ad 25 µl PCR-buffer (1 ml PCR-buffer contains: 100 µl 10×PCR-buffer (Invitrogen), 160 µl nucleotide stem-solution (1.25 mM dNTPs), 30 µl $MgCl_2$, 610 µl aqua dest). The PCR conditions were: 95° C. for 3 min, followed by 32 cycles of: 95° C. for 20 sec, 62° C. for 20 sec, and 70° C. for 10 sec. Finally, the reaction is incubated at 70° C. for 3 min. The PCR Products were separated by gel electrophoresis on a 3.5% TAE-Agarose-Gel with ethidium bromide (10 µl of a 1%-stem solution for every 100 ml). The gelelectrophosesis was allowed to run for 30 min at 130 V.

The following primers were used:

```
rVKORC1-outerF:
                                    (SEQ ID No. 88)
ATC CTG AGT TCC CTG GTG TCT GTC GCT G rVKORC1-outerR:
                                    (SEQ ID No. 89)
TCA GGG CTT TTT GAC CTT GTG TTC TGG C 416G-mutant allele-specific PCR primer
"rVKORC1-innerF":
                                    (SEQ ID No. 90)
TGA TTT CTG CAT TGT TTG CAT CAC CAC ATG 416A-wildtype allele-specific PCR
primer "rVKORC1-innerR":
                                    (SEQ ID No. 91)
CAA CAT CAG GCC CGC ATT GAT GGA AT
```

Rats (*Rattus norvegicus*) with and without warfarin resistance were used for the assay. The results of the PCR are shown in FIG. 13. Wildtype rats exhibited a band at 123 bp, rats homozygous to the mutation exhibited a band at 101 bp and finally, rats with the heterozygous mutation showed two bands, one at 101 and another band at 123 bp.

As a result, this data demonstrate, that this assay can be employed to determine whether a given rat is warfarin resistant or not. Such assays are highly versatile in order to manage pest control in a given region, since knowledge of the frequency of warfarin resistant rats is critical for deciding which pesticide may be employed effectively. If in a given region there is a high prevalence of warfarin resistant rats warfarin and analogues thereof are an unsuitable means to kill the rats. If, however, the determined frequency of warfarin resistant rats is low, warfarin may be effectively used to fight rodents.

LIST OF REFERENCE NUMERALS

Altschul et al., 1997, Nucleic Acids Res., 25:3389-3402
Bandyopadhyay, P. K., Garrett, J. E., Shetty, R. P., Keate, T., Walker, C. S., and Olivera, B. M. (2002). gamma-Glutamyl carboxylation: An extracellular posttranslational modification that antedates the divergence of molluscs, arthropods, and chordates, Proc Natl Acad Sci USA 99, 1264-1269.

Boneh, A., and Bar-Ziv, J. (1996). Hereditary deficiency of vitamin K-dependent coagulation factors with skeletal abnormalities, Am J Med Genet 65, 241-243.

Brenner, B., Sanchez-Vega, B., Wu, S. M., Lanir, N., Stafford, D. W., and Solera, J. (1998). A missense mutation in gamma-glutamyl carboxylase gene causes combined deficiency of all vitamin K-dependent blood coagulation factors, Blood 92, 4554-4559.

Cain, D., Hutson, S. M., and Wallin, R. (1997). Assembly of the warfarin-sensitive vitamin K 2,3-epoxide reductase enzyme complex in the endoplasmic reticulum membrane, J Biol Chem 272, 29068-29075.

Chen, C A and Okayama, H. (1988). Calcium phosphate-mediated transfer: a highly efficient transfection system for stably transforming cells with plasmid DNA. Biotechniques 6, 632-638.

Dockal, M., Carter, D. C., and Ruker, F. (1999). The three recombinant domains of human serum albumin. Structural characterization and ligand binding properties, J Biol Chem 274, 29303-29310.

Dockal, M., Chang, M., Carter, D. C., and Ruker, F. (2000). Five recombinant fragments of human serum albumin-tools for the characterization of the warfarin binding site, Protein Sci 9, 1455-1465.

Doetschman, Gene Transfer in Embryonic Stem Cells, page 115 to 146 in Pinkert, 1994

Ekelund, H., Lindeberg, L., and Wranne, L. (1986). Combined deficiency of coagulation factors II, VII, IX, and X: a case of probable congenital origin, Pediatr Hematol Oncol 3, 187-193.

Esmon, C. T., Suttie, J. W., and Jackson, C. M. (1975). The functional significance of vitamin K action. Difference in phospholipid binding between normal and abnormal prothrombin, J Biol Chem 250, 40954099.

Fasco, M. J., Principe, L. M., Walsh, W. A., and Friedman, P. A. (1983). Warfarin inhibition of vitamin K 2,3-epoxide reductase in rat liver microsomes, Biochemistry 22, 5655-5660.

Fasco, M. J., Preusch, P. C., Hildebrandt, E. & Suttie, J. W. (1983b). Formation of hydroxyvitamin K by vitamin K epoxide reductase of warfarin-resistant rats. J Biol Chem 258, 43724380

Fischer, M., and E., Z. (1966). Kongenitaler Mangel der Faktoren II, VIII und X, Zeitschrift für Kinderheilkunde 95, 309-323.

Fregin, A., Rost, S., Wolz, W., Krebsova, A., Muller, C. R., and Oldenburg, J. (2002). Homozygosity mapping of a second gene locus for hereditary combined deficiency of vitamin K-dependent clotting factors to the centromeric region of chromosome 16, Blood 100, 3229-3232.

Furie, B., and Furie, B. C. (1988). The molecular basis of blood coagulation, Cell 53, 505-518.

Goldsmith, G. H., Jr., Pence, R. E., Ratnoff, O. D., Adelstein, D. J., and Furie, B. (1982). Studies on a family with combined functional deficiencies of vitamin K-dependent coagulation factors, J Clin Invest 69, 1253-1260.

Gossen M. et al. (1994) Curr. Opin. Biotechnol. 5, 516-20

Greavses, J. H., and Ayres, P. (1967). Heritable resistance to warfarin in rats, Nature 215, 877-878.

Guenthner, T. M., Cai, D., and Wallin, R. (1998). Co-purification of microsomal epoxide hydrolase with the warfarin-sensitive vitamin K1 oxide reductase of the vitamin K cycle, Biochem Pharmacol 55, 169-175.

Harlow & Lane, 1998, Using Antibodies: A Laboratory Manual, Cold Spring Harbor Press, New York, USA, Chapter 5, pp. 53-135

Jackson, M. R., Nilsson, T., and Peterson, P. A. (1990). Identification of a consensus motif for retention of transmembrane proteins in the endoplasmic reticulum, Embo J 9, 3153-3162.

Jackson, W. B., Ashton, A. D., and Delventhal, K. (1988). Overview of anticoagulant rodenticide usage and resistance. In Current advances in vitamin K research, J. W. Suttie, ed. (New York, Elsevier), pp. 381-397.

Johnson, C. A., Chung, K. S., McGrath, K. M., Bean, P. E., and Roberts, H. R. (1980). Characterization of a variant prothrombin in a patient congenitally deficient in factors II, VII, IX and X, Br J Haematol 44, 461-469.

Kohn, M. H., and Pelz, H. J. (1999). Genomic assignment of the warfarin resistance locus, Rw, in the rat, Mamm Genome 10, 696-698.

Kozak, 1987, Nucleic. Acids Res. 15: 8125-48

Lee et al. (1981) Nature 214, 228-232

Leonard, C. O. (1988). Vitamin K responsive bleeding disorder: a genocopy of the warfarin embryopathy, Proceedings of the Greenwood Genetic Center 7, 165-166.

Manfioletti, G., Brancolini, C., Avanzi, G., and Schneider, C. (1993). The protein encoded by a growth arrest-specific gene (gas6) is a new member of the vitamin K-dependent proteins related to protein S, a negative coregulator in the blood coagulation cascade, Mol Cell Biol 13, 4976-4985.

Martin, A. D., Steed, L. C., Redfern, R., Gill, J. E. & Huson, L. W. Warfarin-resistance genotype determination in the Norway rat, *Rattus norvegicus. Laboratory Animals,* 209-214 (1979).

McManus et al. 2002, Nature Reviews 3: 737-747, Gene Silencing in Mammals by small interfering RNAs McMillan, C. W., and Roberts, H. R. (1966). Congenital combined deficiency of coagulation factors II, VII, IX and X. Report of a case, N Engl J Med 274, 1313-1315.

Mutero, A., Pralavorio, M., Bride, J. M., and Fournier, D. (1994). Resistance-associated point mutations in insecticide-insensitive acetylcholinesterase, Proc Natl Acad Sci USA 91, 5922-5926.

Monastersky, Gene Transfer Technology; Alternative Techniques and Applications, page 177 to 220 in Pinkert, 1994, supra Mumberg et al. (1994) Nucl. Acids Res., 22, 5767 5768

Nellen and Lichtenstein, 1993, Trends Biochem. Sci. 18: 419-23; Stein, 1992, Leukemia 6: 967-74

Oldenburg, J., von Brederlow, B., Fregin, A., Rost, S., Wolz, W., Eberl, W., Eber, S., Lenz, E., Schwaab, R., Brackmann, H. H., et al. (2000). Congenital deficiency of vitamin K dependent coagulation factors in two families presents as a genetic defect of the vitamin K-epoxide-reductase-complex, Thromb Haemost 84, 937-941.

O'Reilly, R. A. (1970). The second reported kindred with hereditary resistance to oral anticoagulant drugs, N Engl J Med 282, 1448-1451.

O'Reilly, R. A., Aggeler, P. M., Silvija Hoag, M., Leong, L. S., and Kropatkin, M. L. (1964). Hereditary transmission of exceptional resistance to coumarin anticoagulant drugs: the first reported kindred, N Engl J Med 271, 809-815.

Pauli, R. M., Lian, J. B., Mosher, D. F., and Suttie, J. W. (1987). Association of congenital deficiency of multiple vitamin K-dependent coagulation factors and the phenotype of the warfarin embryopathy: clues to the mechanism of teratogenicity of coumarin derivatives, Am J Hum Genet 41, 566-583.

Pechlaner, C., Vogel, W., Erhart, R., Pumpel, E., and Kunz, F. (1992). A new case of combined deficiency of vitamin K dependent coagulation factors, Thromb Haemost 68, 617.

Petersen, C. E., Ha, C. E., Curry, S., and Bhagavan, N. V. (2002). Probing the structure of the warfarin-binding site on human serum albumin using site-directed mutagenesis, Proteins 47, 116-125.

Prentice, C. R. (1985). Acquired coagulation disorders, Clin Haematol 14, 413442. Presnell, S. R., and Stafford, D. W. (2002). The vitamin K-dependent carboxylase, Thromb Haemost 87, 937-946.

Polites and Pinkert, DNA Microinjection and Transgenic Animal Production, page 15 to 68 in Pinkert, 1994, Transgenic animal technology: a laboratory handbook, Academic Press, London, UK Price, P. A. (1988). Role of vitamin-K-dependent proteins in bone metabolism, Annu Rev Nutr 8, 565-583.

Russel et al. (1983), J. Biol. Chem. 258, 2674-2682

Sperling, R., Furie, B. C., Blumenstein, M., Keyt, B., and Furie, B. (1978). Metal binding properties of gamma-carboxyglutamic acid. Implications for the vitamin K-dependent blood coagulation proteins, J Biol Chem 253, 3898-3906.

Spronk, H. M., Farah, R. A., Buchanan, G. R., Vermeer, C., and Soute, B. A. (2000). Novel mutation in the gamma-glutamyl carboxylase gene resulting in congenital combined deficiency of all vitamin K-dependent blood coagulation factors, Blood 96, 3650-3652.

Stitt, T. N., Conn, G., Gore, M., Lai, C., Bruno, J., Radziejewski, C., Mattsson, K., Fisher, J., Gies, D. R., Jones, P. F., and et al. (1995). The anticoagulation factor protein S and its relative, Gas6, are ligands for the Tyro 3/Axl family of receptor tyrosine kinases, Cell 80, 661-670.

Suttie, J. W. (1987). The biochemical basis of warfarin therapy, Adv Exp Med Biol 214, 3-16.

Thijssen, H. H. & Peiz, H. J. in *Advances in vertebrate pest management* (eds. Pelz, H. J., Cowan, D. P. & Feare, C. J.) 181-192 (Filander-Verlag, Fürth, 2001).

Uhlmann, E. & Peyman, A. (1990) Chemical Reviews, 90, 543-584, No. 4

Vicente, V., Maia, R., Alberca, I., Tamagnini, G. P., and Lopez Borrasca, A. (1984). Congenital deficiency of vitamin K-dependent coagulation factors and protein C, Thromb Haemost 51, 343-346.

Wallace, M. E., and MacSwiney, F. J. (1976). A major gene controlling warfarin-resistance in the house mouse, J Hyg (Lond) 76, 173-181.

Wallin, R., and Martin, L. F. (1985). Vitamin K-dependent carboxylation and vitamin K metabolism in liver. Effects of warfarin, J Clin Invest 76, 1879-1884.

Winter and Milstein, 1991, Nature 349:293-299

Wood, Retrovirus-Mediated Gene Transfer, page 147 to 176 in Pinkert, 1994, supra Zheng and Kemeny, 1995, Clin. Exp. Immunol. 100: 380-2;

---

The invention claimed is:

1. A method of diagnosing warfarin resistance in a patient comprising the steps of:
   (I) amplifying a DNA sample obtained from the patient or reverse transcribing an RNA sample obtained from the patient into a DNA and amplifying the DNA; and
   (II) analyzing the amplified DNA of step (I) to determine at least one sequence mutation in an amino acid sequence of the vitamin K epoxide recycling (VKORC1) polypeptide as compared to the VKORC1 sequence set forth in SEQ ID NO: 1 wherein the presence of a mutation in the sequence of SEQ ID NO: 1 in the VKORC1 protein of said patient is indicative of the patient being warfarin resistant;
   wherein said mutation in the amino acid sequence set forth in SEQ ID NO: 1 is selected from the group consisting of V29L, R98W, and Y139C.

2. The method of claim 1, wherein the amplified DNA is analyzed by a technique selected from the group consisting of PCR-based analysis, restriction digestion analysis, and DNA sequencing analysis.

3. A method of diagnosing warfarin resistance in a patient comprising the steps of detecting in a sample the presence of a genetic variation in VKORC1, wherein said VKORC1 is encoded by the sequence of SEQ ID NO: 1 and said genetic variation results in one or more of the following substitutions in the VKORC1 polypeptide: V29L, R98W and Y139C, and wherein the presence of any of said substitutions is diagnostic of said patient having warfarin resistance.

4. A method of diagnosing warfarin resistance in a patient comprising the steps of detecting in a sample the presence of a V29L mutation in the VKORC1 sequence of SEQ ID NO: 1, wherein the presence of said mutation is diagnostic of said patient having warfarin resistance.

* * * * *

SEQUENCE LISTING

```
<160> NUMBER OF SEQ ID NOS: 94

<210> SEQ ID NO 1
<211> LENGTH: 163
<212> TYPE: PRT
<213> ORGANISM: Homo sapiens

<400> SEQUENCE: 1

Met Gly Ser Thr Trp Gly Ser Pro Gly Trp Val Arg Leu Ala Leu Cys
1               5                   10                  15

Leu Thr Gly Leu Val Leu Ser Leu Tyr Ala Leu His Val Lys Ala Ala
            20                  25                  30

Arg Ala Arg Asp Arg Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Gln Asp Ser Ile Leu Asn Gln Ser Asn
65                  70                  75                  80

Ser Ile Phe Gly Cys Ile Phe Tyr Thr Leu Gln Leu Leu Leu Gly Cys
                85                  90                  95

Leu Arg Thr Arg Trp Ala Ser Val Leu Met Leu Leu Ser Ser Leu Val
            100                 105                 110

Ser Leu Ala Gly Ser Val Tyr Leu Ala Trp Ile Leu Phe Phe Val Leu
        115                 120                 125

Tyr Asp Phe Cys Ile Val Cys Ile Thr Thr Tyr Ala Ile Asn Val Ser
    130                 135                 140

Leu Met Trp Leu Ser Phe Arg Lys Val Gln Glu Pro Gln Gly Lys Ala
145                 150                 155                 160

Lys Arg His
```

```
<210> SEQ ID NO 2
<211> LENGTH: 492
<212> TYPE: DNA
<213> ORGANISM: Homo sapiens

<400> SEQUENCE: 2
atgggcagca cctgggggag ccctggctgg gtgcggctcg ctcttttgcct gacgggctta    60 gtgctctcgc tctacgcgct gcacgtgaag gcggcgcgcg cccgggaccg ggattaccgc   120
gcgctctgcg acgtgggcac cgccatcagc tgttcgcgcg tcttctcctc caggtggggc   180
aggggtttcg ggctggtgga gcatgtgctg ggacaggaca gcatcctcaa tcaatccaac   240
agcatattcg gttgcatctt ctacacacta cagctattgt taggttgcct gcggacacgc   300
tgggcctctg tcctgatgct gctgagctcc ctggtgtctc tcgctggttc tgtctacctg   360
gcctggatcc tgttcttcgt gctctatgat ttctgcattg tttgtatcac cacctatgct   420
atcaacgtga gcctgatgtg gctcagtttc cggaaggtcc aagaacccca gggcaaggct   480
aagaggcact ga                                                        492

<210> SEQ ID NO 3
<211> LENGTH: 492
<212> TYPE: DNA
<213> ORGANISM: Homo sapiens

<400> SEQUENCE: 3
atgggcagca cctgggggag ccctggctgg gtgcggctcg ctcttttgcct gacgggctta    60 gtgctctcgc tctacgcgct gcacgtgaag gcggcgcgcg cccgggaccg ggattaccgc   120
gcgctctgcg acgtgggcac cgccatcagc tgttcgcgcg tcttctcctc caggtggggc   180
aggggtttcg ggctggtgga gcatgtgctg ggacaggaca gcatcctcaa tcaatccaac   240
agcatattcg gttgcatctt ctacacacta cagctattgt taggttgcct gtggacacgc   300
tgggcctctg tcctgatgct gctgagctcc ctggtgtctc tcgctggttc tgtctacctg   360
gcctggatcc tgttcttcgt gctctatgat ttctgcattg tttgtatcac cacctatgct   420
atcaacgtga gcctgatgtg gctcagtttc cggaaggtcc aagaacccca gggcaaggct   480
aagaggcact ga                                                        492

<210> SEQ ID NO 4
<211> LENGTH: 492
<212> TYPE: DNA
<213> ORGANISM: Homo sapiens

<400> SEQUENCE: 4
atgggcagca cctgggggag ccctggctgg gtgcggctcg ctcttttgcct gacgggctta    60 gtgctctcgc tctacgcgct gcacttgaag gcggcgcgcg cccgggaccg ggattaccgc   120
gcgctctgcg acgtgggcac cgccatcagc tgttcgcgcg tcttctcctc caggtggggc   180
aggggtttcg ggctggtgga gcatgtgctg ggacaggaca gcatcctcaa tcaatccaac   240
agcatattcg gttgcatctt ctacacacta cagctattgt taggttgcct gcggacacgc   300
tgggcctctg tcctgatgct gctgagctcc ctggtgtctc tcgctggttc tgtctacctg   360
gcctggatcc tgttcttcgt gctctatgat ttctgcattg tttgtatcac cacctatgct   420
atcaacgtga gcctgatgtg gctcagtttc cggaaggtcc aagaacccca gggcaaggct   480
aagaggcact ga                                                        492

<210> SEQ ID NO 5
<211> LENGTH: 492
```

```
<212> TYPE: DNA
<213> ORGANISM: Homo sapiens

<400> SEQUENCE: 5
atgggcagca cctggggag ccctggctgg gtgcggctcg ctctttgcct gacgggctta      60
gtgctctcgc tctacgcgct gcacgtgaag gcggcgcgcg cccgggaccg ggattaccgc    120
gcgctctgcg acgcgggcac cgccatcagc tgttcgcgcg tcttctcctc caggtggggc    180
aggggtttcg ggctggtgga gcatgtgctg ggacaggaca gcatcctcaa tcaatccaac    240
agcatattcg gttgcatctt ctacacacta cagctattgt taggttgcct gcggacacgc    300
tgggcctctg tcctgatgct gctgagctcc ctggtgtctc tcgctggttc tgtctacctg    360
gcctggatcc tgttcttcgt gctctatgat ttctgcattg tttgtatcac cacctatgct    420
atcaacgtga gcctgatgtg gctcagtttc cggaaggtcc aagaacccca gggcaaggct    480
aagaggcact ga                                                        492

<210> SEQ ID NO 6
<211> LENGTH: 492
<212> TYPE: DNA
<213> ORGANISM: Homo sapiens

<400> SEQUENCE: 6
atgggcagca cctggggag ccctggctgg gtgcggctcg ctctttgcct gacgggctta      60
gtgctctcgc tctacgcgct gcacgtgaag gcggcgcgcg cccgggaccg ggattaccgc    120
gcgctctgcg acgtgggcac cgccatcagc tgttcgcgcg tcttctcctc cgggtggggc    180
aggggtttcg ggctggtgga gcatgtgctg ggacaggaca gcatcctcaa tcaatccaac    240
agcatattcg gttgcatctt ctacacacta cagctattgt taggttgcct gcggacacgc    300
tgggcctctg tcctgatgct gctgagctcc ctggtgtctc tcgctggttc tgtctacctg    360
gcctggatcc tgttcttcgt gctctatgat ttctgcattg tttgtatcac cacctatgct    420
atcaacgtga gcctgatgtg gctcagtttc cggaaggtcc aagaacccca gggcaaggct    480
aagaggcact ga                                                        492

<210> SEQ ID NO 7
<211> LENGTH: 492
<212> TYPE: DNA
<213> ORGANISM: Homo sapiens

<400> SEQUENCE: 7
atgggcagca cctggggag ccctggctgg gtgcggctcg ctctttgcct gacgggctta      60
gtgctctcgc tctacgcgct gcacgtgaag gcggcgcgcg cccgggaccg ggattaccgc    120
gcgctctgcg acgtgggcac cgccatcagc tgttcgcgcg tcttctcctc caggtggggc    180
aggggtttcg ggctggtgga gcatgtgctg ggacaggaca gcatcctcaa tcaatccaac    240
agcatattcg gttgcatctt ctacacacta cagctattgt taggttgcct gcggacacgc    300
tgggcctctg tcctgatgct gctgagctcc ctggtgtctc tcgctggttc tgtctacctg    360
gcctggatcc tgttcttcgt gcgctatgat ttctgcattg tttgtatcac cacctatgct    420
atcaacgtga gcctgatgtg gctcagtttc cggaaggtcc aagaacccca gggcaaggct    480
aagaggcact ga                                                        492

<210> SEQ ID NO 8
<211> LENGTH: 492
<212> TYPE: DNA
<213> ORGANISM: Homo sapiens
```

<400> SEQUENCE: 8

```
atgggcagca cctgggggag ccctggctgg gtgcggctcg ctctttgcct gacgggctta      60
gtgctctcgc tctacgcgct gcacgtgaag gcggcgcgcg cccgggaccg ggattaccgc     120
gcgctctgtg acgtgggcac cgccatcagc tgttcgcgcg tcttctcctc caggtggggc     180
aggggtttcg ggctggtgga gcatgtgctg gacaggaca gcatcctcaa tcaatccaac      240
agcatattcg gttgcatctt ctacacacta cagctattgt taggttgcct gcggacacgc     300
tgggcctctg tcctgatgct gctgagctcc ctggtgtctc tcgctggttc tgtctacctg     360
gcctggatcc tgttcttcgt gctctatgat ttctgcattg tttgtatcac cacctatgct     420
atcaacgtga gcctgatgtg gctcagtttc cggaaggtcc aagaacccca gggcaaggct     480
aagaggcact ga                                                         492
```

<210> SEQ ID NO 9
<211> LENGTH: 492
<212> TYPE: DNA
<213> ORGANISM: Homo sapiens

<400> SEQUENCE: 9

```
atgggcagca cctgggggag ccctggctgg gtgcggctcg ctctttgcct gacgggctta      60
gtgctctcgc tctacgcgct gcacgtgaag gcggcgcgcg cccgggaccg ggattaccgc     120
gcgctctgcg acgtgggcac cgccatcagc tgttcgcgcg tcttctcctc caggtggggc     180
aggggtttcg ggctggtgga gcatgtgctg gacaggaca gcatcctcaa tcaatccaac      240
agcatattcg gttgcatctt ctacacacta cagctattgt taggttgcct gcggacacgc     300
tgggcctctg tcctgatgct gctgagctcc ctggtgtctc tcgctggttc tgtctacttg     360
gcctggatcc tgttcttcgt gctctatgat ttctgcattg tttgtatcac cacctatgct     420
atcaacgtga gcctgatgtg gctcagtttc cggaaggtcc aagaacccca gggcaaggct     480
aagaggcact ga                                                         492
```

<210> SEQ ID NO 10
<211> LENGTH: 176
<212> TYPE: PRT
<213> ORGANISM: Homo sapiens

<400> SEQUENCE: 10

```
Met Ala Ala Pro Val Leu Leu Arg Val Ser Val Pro Arg Trp Glu Arg
1               5                   10                  15
Val Ala Arg Tyr Ala Val Cys Ala Ala Gly Ile Leu Leu Ser Ile Tyr
            20                  25                  30
Ala Tyr His Val Glu Arg Glu Lys Glu Arg Asp Pro His Arg Ala
        35                  40                  45
Leu Cys Asp Leu Gly Pro Trp Val Lys Cys Ser Ala Ala Leu Ala Ser
    50                  55                  60
Arg Trp Gly Arg Gly Phe Gly Leu Leu Gly Ser Ile Phe Gly Lys Asp
65                  70                  75                  80
Gly Val Leu Asn Gln Pro Asn Ser Val Phe Gly Leu Ile Phe Tyr Ile
                85                  90                  95
Leu Gln Leu Leu Leu Gly Met Thr Ala Ser Ala Val Ala Ala Leu Ile
            100                 105                 110
Leu Met Thr Ser Ser Ile Met Ser Val Val Gly Ser Leu Tyr Leu Ala
        115                 120                 125
Tyr Ile Leu Tyr Phe Val Leu Lys Glu Phe Cys Ile Ile Cys Ile Val
```

```
            130                 135                 140
Thr Tyr Val Leu Asn Phe Leu Leu Ile Ile Asn Tyr Lys Arg Leu
145                 150                 155                 160

Val Tyr Leu Asn Glu Ala Trp Lys Arg Gln Leu Gln Pro Lys Gln Asp
                165                 170                 175

<210> SEQ ID NO 11
<211> LENGTH: 531
<212> TYPE: DNA
<213> ORGANISM: Homo sapiens

<400> SEQUENCE: 11
atggcggctc cgtcctgct  aagagtgtcg gtgccgcggt gggagcgggt ggcccggtat    60
gcagtgtgcg ctgccggaat cctgctctcc atctacgcct accacgtgga gcggagaag    120 gagcgggacc ccgagcaccg ggccctctgc gacctggggc cctgggtgaa gtgctccgcc    180
gcccttgcct ccagatgggg tcgaggattt ggtcttttgg gttccatttt tggaaaggat    240
ggtgtattaa accagccaaa cagtgtcttt ggacttatat tttatatact acagttatta    300
cttggcatga cagcaagcgc tgtggcggct ttgatcctca tgacgtcctc catcatgtcg    360
gtcgtggggt ccctgtacct ggcctacatt ctgtactttg tgctgaagga gttctgcatc    420
atctgcatcg tcacgtacgt gctgaacttc cttcttctca ttatcaacta caaacgacta    480
gtttacttga cgaggcctg  gaagcggcag ctgcaaccca agcaggactg a             531

<210> SEQ ID NO 12
<211> LENGTH: 161
<212> TYPE: PRT
<213> ORGANISM: Rattus norvegicus

<400> SEQUENCE: 12

Met Gly Thr Thr Trp Arg Ser Pro Gly Arg Leu Arg Leu Ala Leu Cys
1               5                   10                  15

Leu Ala Gly Leu Ala Leu Ser Leu Tyr Ala Leu His Val Lys Ala Ala
                20                  25                  30

Arg Ala Arg Asn Glu Asp Tyr Arg Ala Leu Cys Asp Val Gly Thr Ala
            35                  40                  45

Ile Ser Cys Ser Arg Val Phe Ser Ser Arg Trp Gly Arg Gly Phe Gly
        50                  55                  60

Leu Val Glu His Val Leu Gly Ala Asp Ser Ile Leu Asn Gln Ser Asn
65                  70                  75                  80

Ser Ile Phe Gly Cys Met Phe Tyr Thr Ile Gln Leu Leu Leu Gly Cys
                85                  90                  95

Leu Arg Gly Arg Trp Ala Ser Ile Leu Leu Ile Leu Ser Ser Leu Val
            100                 105                 110

Ser Val Ala Gly Ser Leu Tyr Leu Ala Trp Ile Leu Phe Phe Val Leu
        115                 120                 125

Tyr Asp Phe Cys Ile Val Cys Ile Thr Thr Tyr Ala Ile Asn Ala Gly
    130                 135                 140

Leu Met Leu Leu Ser Phe Gln Lys Val Pro Glu His Lys Val Lys Lys
145                 150                 155                 160

Pro

<210> SEQ ID NO 13
<211> LENGTH: 486
<212> TYPE: DNA
<213> ORGANISM: Rattus norvegicus
```

<400> SEQUENCE: 13

```
atgggcacca cctggaggag ccctggacgt ttgcggcttg cactatgcct cgctggccta    60
gccctctcac tgtacgcact gcacgtgaag gcggcgcgcg cccgcaatga ggattaccgc   120
gcgctctgcg acgtgggcac ggccatcagc tgttcccgcg tcttctcctc tcggtggggc   180
cggggctttg gctggtgga gcacgtgtta ggagctgaca gcatcctcaa ccaatccaac   240
agcatatttg gttgcatgtt ctacaccata cagctgttgt taggttgctt gaggggacgt   300
tgggcctcta tcctactgat cctgagttcc ctggtgtctg tcgctggttc tctgtacctg   360
gcctggatcc tgttctttgt cctgtatgat ttctgcattg tttgcatcac cacctatgcc   420
atcaatgcgg gcctgatgtt gcttagcttc agaaggtgc cagaacacaa ggtcaaaaag   480
ccctga                                                              486
```

<210> SEQ ID NO 14
<211> LENGTH: 486
<212> TYPE: DNA
<213> ORGANISM: Rattus norvegicus

<400> SEQUENCE: 14

```
atgggcacca cctggaggag ccctggacgt ttgcggcttg cactatgcct cgctggccta    60
gccctctcac tgtacgcact gcacgtgaag gcggcgcgcg cccgcaatga ggattaccgc   120
gcgctctgcg acgtgggcac ggccatcagc tgttcccgcg tcttctcctc tcggtggggc   180
cggggctttg gctggtgga gcacgtgtta ggagctgaca gcatcctcaa ccaatccaac   240
agcatatttg gttgcatgtt ctacaccata cagctgttgt taggttgctt gaggggacgt   300
tgggcctcta tcctactgat cctgagttcc ctggtgtctg tcgctggttc tctgtacctg   360
gcctggatcc tgttctttgt cctgtatgat ttctgcattg tttgcatcac cacctgtgcc   420
atcaatgcgg gcctgatgtt gcttagcttc agaaggtgc cagaacacaa ggtcaaaaag   480
ccctga                                                              486
```

<210> SEQ ID NO 15
<211> LENGTH: 176
<212> TYPE: PRT
<213> ORGANISM: Rattus norvegicus

<400> SEQUENCE: 15

```
Met Ala Ala Pro Val Leu Leu Arg Val Ser Val Pro Arg Trp Glu Arg
 1               5                  10                  15

Val Ala Arg Tyr Ala Val Cys Ala Ala Gly Ile Leu Leu Ser Ile Tyr
            20                  25                  30

Ala Tyr His Val Glu Arg Glu Lys Glu Arg Asp Pro Glu His Arg Ala
        35                  40                  45

Leu Cys Asp Leu Gly Pro Trp Val Lys Cys Ser Ala Ala Leu Ala Ser
    50                  55                  60

Arg Trp Gly Arg Gly Phe Gly Leu Leu Gly Ser Ile Phe Gly Lys Asp
65                  70                  75                  80

Gly Val Leu Asn Gln Pro Asn Ser Val Phe Gly Leu Ile Phe Tyr Ile
                85                  90                  95

Leu Gln Leu Leu Leu Gly Met Thr Ala Ser Ala Val Ala Ala Leu Val
            100                 105                 110

Leu Met Thr Ser Ser Ile Val Ser Val Gly Ser Leu Tyr Leu Ala
        115                 120                 125

Tyr Ile Leu Tyr Phe Val Leu Lys Glu Phe Cys Ile Ile Cys Val Thr
    130                 135                 140
```

Thr Tyr Val Leu Asn Phe Leu Leu Ile Ile Asn Tyr Lys Arg Leu
145                 150                 155                 160

Val Tyr Leu Asn Glu Ala Trp Lys Arg Gln Leu Gln Pro Lys Glu Asp
                165                 170                 175

<210> SEQ ID NO 16
<211> LENGTH: 531
<212> TYPE: DNA
<213> ORGANISM: Rattus norvegicus

<400> SEQUENCE: 16

```
atggcggcgc ccgtcctgct gagagtgtcg gtgccgcggt gggaacgggt ggcccggtat      60
gcagtgtgcg ccgccgggat cctgctctcc atctacgcct accacgtgga gcgggagaag     120
gagagggacc cggagcaccg ggccctctgc gacctggggc cctgggtgaa gtgctccgcc     180
gccctggcct ccagatgggg tcgaggattt ggtcttttgg gttccatttt tggaaaagat     240
ggtgtattaa accagccaaa cagtgtcttt ggacttatat tttatatact acagttatta     300
cttggcatga cagccagcgc agttgcagct ctggtcctca tgacctcctc catcgtgtcc     360
gtggtggggt ctttgtacct ggcctacatt ctgtactttg tgctgaagga gttttgcatc     420
atctgcgtca ccacatatgt gctgaacttc cttctcctca tcatcaacta caaacgactg     480
gtttacttga atgaggcctg gaagcgacaa ctgcagccta aggaagactg a              531
```

<210> SEQ ID NO 17
<211> LENGTH: 161
<212> TYPE: PRT
<213> ORGANISM: Mus musculus

<400> SEQUENCE: 17

Met Gly Thr Thr Trp Arg Ser Pro Gly Leu Val Arg Leu Ala Leu Cys
1               5                   10                  15

Leu Ala Gly Leu Ala Leu Ser Leu Tyr Ala Leu His Val Lys Ala Ala
                20                  25                  30

Arg Ala Arg Asp Glu Asn Tyr Arg Ala Leu Cys Asp Val Gly Thr Ala
            35                  40                  45

Ile Ser Cys Ser Arg Val Phe Ser Ser Arg Trp Gly Arg Gly Phe Gly
        50                  55                  60

Leu Val Glu His Met Leu Gly Ala Asp Ser Val Leu Asn Gln Ser Asn
65                  70                  75                  80

Ser Ile Phe Gly Cys Leu Phe Tyr Thr Leu Gln Leu Leu Leu Gly Cys
                85                  90                  95

Leu Arg Gly Arg Trp Ala Ser Ile Leu Leu Val Leu Ser Ser Leu Val
                100                 105                 110

Ser Val Ala Gly Ser Val Tyr Leu Ala Trp Ile Leu Phe Phe Val Leu
            115                 120                 125

Tyr Asp Phe Cys Ile Val Cys Ile Thr Thr Tyr Ala Ile Asn Val Gly
        130                 135                 140

Leu Met Leu Leu Ser Phe Gln Lys Val Pro Glu His Lys Thr Lys Lys
145                 150                 155                 160

His

<210> SEQ ID NO 18
<211> LENGTH: 486
<212> TYPE: DNA
<213> ORGANISM: Mus musculus

<400> SEQUENCE: 18

```
atgggcacca cctggaggag ccctggactc gtgcggcttg cactgtgcct cgctggctta    60
gccctctcac tgtacgcact gcacgtgaag gcggcgcgcg cccgcgatga aaattaccgc   120
gcgctctgcg atgtgggcac ggccatcagc tgttcccgcg tcttctcctc tcggtggggc   180
cggggctttg ggctggtgga gcacatgcta ggagcggaca gcgtcctcaa ccaatccaac   240
agcatatttg gttgcctgtt ctacaccttr cagctgttgt taggttgctt gaggggacgt   300
tgggcctcta tcctactggt gctgagttcc ctggtgtccg tcgctggttc cgtgtacctg   360
gcctggatcc tgttctttgt gttatatgat ttctgcattg tgtgcattac cacctatgcc   420
atcaatgtgg gtctgatgtt gcttagcttc cagaaggtac cagaacacaa gaccaaaaag   480
cactga                                                              486
```

<210> SEQ ID NO 19
<211> LENGTH: 176
<212> TYPE: PRT
<213> ORGANISM: Mus musculus

<400> SEQUENCE: 19

```
Met Ala Ala Pro Val Leu Leu Arg Val Ser Val Pro Arg Trp Glu Arg
1               5                   10                  15

Val Ala Arg Tyr Ala Val Cys Ala Ala Gly Ile Leu Leu Ser Ile Tyr
            20                  25                  30

Ala Tyr His Val Glu Arg Glu Lys Glu Arg Asp Pro Glu His Arg Ala
        35                  40                  45

Leu Cys Asp Leu Gly Pro Trp Val Lys Cys Ser Ala Ala Leu Ala Ser
    50                  55                  60

Arg Trp Gly Arg Gly Phe Gly Leu Leu Gly Ser Ile Phe Gly Lys Asp
65                  70                  75                  80

Gly Val Leu Asn Gln Pro Asn Ser Val Phe Gly Leu Ile Phe Tyr Ile
                85                  90                  95

Leu Gln Leu Leu Leu Gly Met Thr Ala Ser Ala Val Ala Ala Leu Val
            100                 105                 110

Leu Met Thr Ser Ser Ile Val Ser Val Val Gly Ser Leu Tyr Leu Ala
        115                 120                 125

Tyr Ile Leu Tyr Phe Val Leu Lys Glu Phe Cys Ile Ile Cys Val Thr
    130                 135                 140

Thr Tyr Val Leu Asn Phe Leu Leu Ile Ile Asn Tyr Lys Arg Leu
145                 150                 155                 160

Val Tyr Leu Asn Glu Ala Trp Lys Arg Gln Leu Gln Pro Lys Glu Asp
                165                 170                 175
```

<210> SEQ ID NO 20
<211> LENGTH: 531
<212> TYPE: DNA
<213> ORGANISM: Mus musculus

<400> SEQUENCE: 20

```
atggcggcgc ccgtcctgct gagagtgtcg gtgccgcgtt gggaacgggt ggcccggtat    60
gcagtgtgcg ccgccgggat cctgctctcc atctacgcct accacgtgga gcgggagaag   120
gagagggacc cggagcaccg ggccctctgc gacctggggc cctgggtgaa gtgctccgcc   180
gccctggcct ccagatgggg tcgaggattt ggtcttttgg gttccatttt tggaaaagat   240
ggtgtattaa accagccaaa cagtgtcttt ggacttatat tttatatact acagttatta   300
cttggcatga cagccagcgc agttgcagct ctggtcctca tgacctcctc cattgtgtct   360
```

```
gtggtgggct ctttgtacct ggcctacatt ctgtactttg tgctgaaaga gttttgcatc    420
atctgcgtca ccacatatgt gctgaacttc ctcctcctca tcatcaatta caaacgacta    480
gtttatttga atgaggcctg aagcgacag ctgcagccta aggaagactg a              531
```

<210> SEQ ID NO 21
<211> LENGTH: 163
<212> TYPE: PRT
<213> ORGANISM: Fugu rubripes

<400> SEQUENCE: 21

```
Met Ala Ile Pro Thr Trp Glu Arg Lys Val Arg Ile Phe Leu Cys Val
1               5                   10                  15

Phe Gly Leu Leu Leu Ser Val Tyr Ala Leu His Val Glu Leu Ser Arg
            20                  25                  30

Glu Arg Asn Pro Asp Tyr Arg Ala Met Cys Asp Leu Gly Glu Ser Val
        35                  40                  45

Ser Cys Ser Lys Val Phe Ser Ser Arg Trp Gly Arg Gly Phe Gly Leu
    50                  55                  60

Val Gln Tyr Phe Val Asp Lys Asp Ser Pro Leu Asn Gln Pro Asn Ser
65                  70                  75                  80

Val Leu Gly Ile Ile Phe Tyr Thr Leu Gln Met Cys Leu Gly Leu Ser
                85                  90                  95

Leu Ser Arg Lys Ala Ala Leu Phe Leu Val Phe Ser Ser Trp Val Ser
            100                 105                 110

Val Ala Gly Ser Leu Tyr Leu Ala Ser Ile Leu Ala Phe Val Leu Gly
        115                 120                 125

Asp Phe Cys Met Val Cys Val Ser Thr Tyr Leu Val Asn Phe Val Leu
    130                 135                 140

Leu Phe Thr Asn Leu Lys Arg Arg Arg Ala Ile Glu Gly Leu Lys Glu
145                 150                 155                 160

Lys Ser Gly
```

<210> SEQ ID NO 22
<211> LENGTH: 492
<212> TYPE: DNA
<213> ORGANISM: Fugu rubripes

<400> SEQUENCE: 22

```
atggcgatcc ccacatggga gagaaaagtg cgcatatttc tctgtgtttt tggattactt    60
ttgtctgttt acgcgctcca cgtcgagcta tcccgagaga aaacccggga ttacagggcg    120
atgtgcgacc tgggggagtc tgtgagctgc tctaaggttt tcagctccag atggggacgg    180
ggttttggcc tagtccagta ctttgttgac aaagatagcc ctctgaacca gcccaacagt    240
gtgcttggca tcattttta cactctgcag atgtgtcttg gactgtctct gtccagaaaa    300
gctgcgctgt ttttagtctt ctcctcctgg gtgtctgtgg ccggctccct ctatctggca    360
tcgattctag cgtttgttct gggagacttc tgtatggtct gtgtgtcaac atatcttgtt    420
aacttcgtac tgctcttcac taaccctgaaa cgacggagag caattgaagg actgaaggag    480
aagtctggat ag                                                        492
```

<210> SEQ ID NO 23
<211> LENGTH: 175
<212> TYPE: PRT
<213> ORGANISM: Fugu rubripes

<400> SEQUENCE: 23

```
Met Ala Ala Pro Val Leu Arg Val Ser Thr Pro Arg Trp Glu Arg Ile
1               5                   10                  15

Ala Arg Val Leu Val Cys Leu Leu Gly Ile Leu Leu Ser Leu Tyr Ala
            20                  25                  30

Phe His Val Glu Arg Glu His Ala Arg Asp Pro Ser Tyr Lys Ala Leu
        35                  40                  45

Cys Asp Val Ser Ser Ile Ser Cys Ser Lys Val Phe Gly Ser Arg
    50                  55                  60

Trp Gly Arg Gly Phe Gly Leu Leu Gly Ser Ile Phe Gly Asn Asp Ser
65              70                  75                  80

Ala Leu Asn Gln Pro Asn Ser Val Tyr Gly Ile Val Phe Tyr Ala Phe
            85                  90                  95

Gln Leu Leu Leu Gly Met Thr Val Ser Ala Met Ala Ala Leu Ile Leu
            100                 105                 110

Met Thr Thr Ser Ile Met Ser Val Val Gly Ser Leu Tyr Leu Gly Tyr
            115                 120                 125

Ile Leu Tyr Phe Val Leu Lys Asp Leu Cys Val Ile Cys Val Thr Thr
130                 135                 140

Tyr Ala Leu Asn Phe Ile Leu Phe Val Leu Asn Tyr Lys Arg Leu Val
145                 150                 155                 160

Tyr Leu Asn Glu Ala Trp Lys Gln Lys Leu Gln Ala Lys Gln Asp
            165                 170                 175

<210> SEQ ID NO 24
<211> LENGTH: 528
<212> TYPE: DNA
<213> ORGANISM: Fugu rubripes

<400> SEQUENCE: 24
atggcggcgc ccgtcctgag agtatccacc cctcggtggg aaagaatagc ccgggtcctc      60
gtgtgcctcc tgggcatact gctgtctctg tacgccttcc acgtggagag gaacatgct     120 cgggatccca gttataaggc tttgtgcgac gtcagtagct ccatcagctg ttctaaagtg    180
ttcggctcca ggtggggccg aggatttgga ctcttgggct ccattttgg gaatgacagc    240 gcactgaacc aacccaacag cgtctacggg atcgtctttt acgccttcca gcttttacta    300
ggaatgacgg tcagtgcgat ggcggccctg atcctcatga ccacgtccat catgtcggtg    360
gtgggctcgc tctacctggg ctacatcctc tactttgtcc tcaaggacct gtgcgtcatc    420
tgcgtcacca cgtacgcgct gaacttcatc cttttttgtcc tcaactacaa gcgactggtt    480
tacttgaacg aggcctggaa gcagaagctc caggccaagc aggactaa                 528

<210> SEQ ID NO 25
<211> LENGTH: 169
<212> TYPE: PRT
<213> ORGANISM: Xenopus laevis

<400> SEQUENCE: 25

Met Ser Val Pro Gly Trp Glu Arg Pro Val Arg Leu Leu Leu Cys Ser
1               5                   10                  15

Val Gly Ile Ala Leu Ser Leu Tyr Ala Phe His Val Glu Thr Ser Arg
            20                  25                  30

Glu Arg Asp Pro Asp Tyr Thr Ala Leu Cys Asp Ile Asn Pro Ser Ile
            35                  40                  45

Ser Cys Ser Lys Val Phe Thr Ser Arg Trp Gly Arg Gly Phe Gly Leu
    50                  55                  60

Val Glu Gln Phe Leu Gly Gln Gln Ser Leu Leu Asn Gln Pro Asn Ser
```

```
                65                  70                  75                  80
Val Phe Gly Val Leu Phe Tyr Gly Leu Gln Leu Leu Gly Phe Ser
                    85                  90                  95

Gly Ser Leu Ala Ala Ala Ser Thr Leu Leu Gly Thr Ser Leu Met Ser
                100                 105                 110

Ile Gly Gly Ser Met Tyr Leu Ala Tyr Ile Leu Val Tyr Val Leu Arg
            115                 120                 125

Asp Phe Cys Val Ile Cys Val Ser Thr Tyr Val Leu Asn Leu Leu
        130                 135                 140

Leu Leu Leu Asn Leu Lys Arg Leu Ser Ser Leu Arg Ala Pro Pro Lys
145                 150                 155                 160

Lys His Lys Asn Lys Arg Lys Lys Asn
                165

<210> SEQ ID NO 26
<211> LENGTH: 510
<212> TYPE: DNA
<213> ORGANISM: Xenopus laevis

<400> SEQUENCE: 26
atgtctgtgc cgggctggga gaggccagtg aggctgttgc tgtgctctgt gggtattgcc      60
ctgtcactat atgccttcca tgtagagacc tcccgggaaa gagacccega ctataccgct     120 ctgtgtgaca tcaaccccte catcagetge tccaaggtct tcacttccag atgggggcga     180
ggatttgggc tcgtggagca attcctgggg cagcagagtt tgctgaatca gcccaacagc     240
gtgtttggag tcctgttcta cggcctgcag ctcctgctgg gtttcagcgg atccctggct     300
gccgcctcca cgctactggg aacgtctctg atgtccatcg ggggctccat gtacttggcc     360
tatatcctgg tctatgtact gcgcgacttc tgcgttatct gcgtctccac ctacgtcctg     420
aacctcctcc tcctcctgct caacctcaag cgcctgtcct ccctccgagc gccccccaaa     480
aagcacaaga caaacgcaa gaagaactaa                                       510

<210> SEQ ID NO 27
<211> LENGTH: 176
<212> TYPE: PRT
<213> ORGANISM: Anopheles gambiae

<400> SEQUENCE: 27

Met Ser Ile Leu Ala Gly Asn Cys Lys Cys Thr Tyr Thr Leu Ala Leu
1               5                   10                  15

Val Gly Leu Ser Val Cys Gly Phe Leu Leu Ser Leu Tyr Thr Ser Tyr
            20                  25                  30

Val Glu Leu Arg Ala Glu His Asp His Thr Tyr Gln Ala Met Cys Asp
        35                  40                  45

Ile Ser Glu Arg Ile Ser Cys Thr Lys Val Phe Thr Ser Arg Tyr Gly
    50                  55                  60

Arg Gly Phe Gly Ile Val Gly Pro Leu Leu Gly Asp Asp Ser Leu Leu
65                  70                  75                  80

Asn Val Pro Asn Gly Phe Tyr Gly Ile Phe Tyr Phe Leu Val Ala
                85                  90                  95

Gly Leu Ser Phe Ser Asn Asn Leu Ala Val Ser Arg Leu Thr Ser Tyr
                100                 105                 110

Leu Ile Leu Leu Ser Asn Gly Leu Ser Leu Tyr Leu Ala Tyr Leu Leu
            115                 120                 125

Tyr Phe Val Leu Gln Asp Met Cys Val Val Cys Val Thr Thr Tyr Ala
        130                 135                 140
```

Val Asn Leu Val Ser Leu Ile Leu Ala Leu Gln Lys Ile Gln Ala Leu
145                 150                 155                 160

Ile Arg Glu Glu Gln Val Met Arg Ala Leu Lys Val Gly Lys Ala Lys
                165                 170                 175

<210> SEQ ID NO 28
<211> LENGTH: 528
<212> TYPE: DNA
<213> ORGANISM: Anopheles gambiae

<400> SEQUENCE: 28
atgagcatcc tggcgggcaa ctgcaaatgc acgtacacgc tcgcgctcgt cggcctgagc        60
gtgtgcggct ttctgctgtc gctgtacacg tcctacgtgg agctgcgggc cgagcacgac       120
catacctacc aggccatgtg cgacattagc gagcgcatca gctgcaccaa agtgtttacc       180
tccaggtacg gcgtggtttt tggcattgtc gggccgttgc tcggcgacga ctcgctgctg       240
aacgtgccga cgggttcta cggcatcttc tactacttcc tagtggccgg cctcagcttc        300
agcaacaatc tggccgtctc gcggctgacc agctacctca tactgctgtc caacgggctg       360
tcgctctacc tcgcctacct gctctacttc gtgctgcagg acatgtgcgt cgtgtgcgtc       420
accacgtacg cggtcaatct ggtcagcctg atactggcgc tgcagaaaat tcaggctctg       480
atccgggagg agcaggtaat gcgcgcgctc aaggttggca aggcaaag                    528

<210> SEQ ID NO 29
<211> LENGTH: 21
<212> TYPE: RNA
<213> ORGANISM: Artificial sequence
<220> FEATURE:
<223> OTHER INFORMATION: siRNA sequence 1 homo sapiens vitamin K
      epoxide reductase complex subunit 1 (Hs_VKORC1)

<400> SEQUENCE: 29
gguugcaucu ucuacacacu u                                                  21

<210> SEQ ID NO 30
<211> LENGTH: 21
<212> TYPE: RNA
<213> ORGANISM: Artificial sequence
<220> FEATURE:
<223> OTHER INFORMATION: siRNA sequence 2 of homo sapiens vitamin K
      epoxide reductase complex subunit 1 (Hs_VKORC1)

<400> SEQUENCE: 30
uuccaacgua gaagaugugu g                                                  21

<210> SEQ ID NO 31
<211> LENGTH: 57
<212> TYPE: DNA
<213> ORGANISM: Artificial sequence
<220> FEATURE:
<223> OTHER INFORMATION: Downstream primer 1 for homo sapiens vitamin
      K epoxide reductase complex subunit 1 (Hs_VKORC1) siRNA sequence

<400> SEQUENCE: 31
caaaaactgt aaaaggttg catcttctac acacggtgtt tcgtcctttc cacaaga           57

<210> SEQ ID NO 32
<211> LENGTH: 57
<212> TYPE: DNA
<213> ORGANISM: Artificial sequence
<220> FEATURE:
<223> OTHER INFORMATION: Downstream primer 2 for homo sapiens vitamin
      K epoxide reductase complex subunit 1 (Hs_VKORC1) siRNA sequence

```
<400> SEQUENCE: 32
caaaaactgt aaaaagtgtg tagaagatgc aaccggtgtt tcgtcctttc cacaaga         57

<210> SEQ ID NO 33
<211> LENGTH: 21
<212> TYPE: RNA
<213> ORGANISM: Artificial sequence
<220> FEATURE:
<223> OTHER INFORMATION: siRNA sequence 3  homo sapiens vitamin K
      epoxide reductase complex subunit 1 (Hs_VKORC1)

<400> SEQUENCE: 33
gucucucgcu gguucugucu u                                               21

<210> SEQ ID NO 34
<211> LENGTH: 21
<212> TYPE: RNA
<213> ORGANISM: Artificial sequence
<220> FEATURE:
<223> OTHER INFORMATION: siRNA sequence 4 homo sapiens vitamin K
      epoxide reductase complex subunit 1 (Hs_VKORC1)

<400> SEQUENCE: 34
uucagagagc gaccaagaca g                                               21

<210> SEQ ID NO 35
<211> LENGTH: 57
<212> TYPE: DNA
<213> ORGANISM: Artificial sequence
<220> FEATURE:
<223> OTHER INFORMATION: Downstream primer 3 for homo sapiens vitamin
      K epoxide reductase complex subunit 1 (Hs_VKORC1) siRNA sequence

<400> SEQUENCE: 35
caaaaactgt aaaagtctc tcgctggttc tgtcggtgtt tcgtcctttc cacaaga         57

<210> SEQ ID NO 36
<211> LENGTH: 57
<212> TYPE: DNA
<213> ORGANISM: Artificial sequence
<220> FEATURE:
<223> OTHER INFORMATION: Downstream primer 4 for homo sapiens vitamin
      K epoxide reductase complex subunit 1 (Hs_VKORC1) siRNA sequence

<400> SEQUENCE: 36
caaaaactgt aaaagacag aaccagcgag agacggtgtt tcgtcctttc cacaaga         57

<210> SEQ ID NO 37
<211> LENGTH: 21
<212> TYPE: RNA
<213> ORGANISM: Artificial sequence
<220> FEATURE:
<223> OTHER INFORMATION: siRNA sequence 5 homo sapiens vitamin K
      epoxide reductase complex subunit 1 (Hs_VKORC1)

<400> SEQUENCE: 37
ggccuggauc cuguucuucu u                                               21

<210> SEQ ID NO 38
<211> LENGTH: 21
<212> TYPE: RNA
<213> ORGANISM: Artificial sequence
<220> FEATURE:
<223> OTHER INFORMATION: siRNA sequence 6 homo sapiens vitamin K
      epoxide reductase complex subunit 1 (Hs_VKORC1)

<400> SEQUENCE: 38
```
uuccggaccu aggacaagaa g                                         21

<210> SEQ ID NO 39
<211> LENGTH: 57
<212> TYPE: DNA
<213> ORGANISM: Artificial sequence
<220> FEATURE:
<223> OTHER INFORMATION: Downstream primer 5 for homo sapiens vitamin
      K epoxide reductase complex subunit 1 (Hs_VKORC1) siRNA sequence

<400> SEQUENCE: 39
caaaaactgt aaaaaggcct ggatcctgtt cttcggtgtt tcgtcctttc cacaaga      57

<210> SEQ ID NO 40
<211> LENGTH: 57
<212> TYPE: DNA
<213> ORGANISM: Artificial sequence
<220> FEATURE:
<223> OTHER INFORMATION: Downstream primer 6 for homo sapiens vitamin
      K epoxide reductase complex subunit 1 (Hs_VKORC1) siRNA sequence

<400> SEQUENCE: 40
caaaaactgt aaaagaaga acaggatcca ggccggtgtt tcgtcctttc cacaaga       57

<210> SEQ ID NO 41
<211> LENGTH: 21
<212> TYPE: RNA
<213> ORGANISM: Artificial sequence
<220> FEATURE:
<223> OTHER INFORMATION: siRNA sequence 7 homo sapiens vitamin K
      epoxide reductase complex subunit 1 (Hs_VKORC1)

<400> SEQUENCE: 41
gauccuguuc uucgugcucu u                                         21

<210> SEQ ID NO 42
<211> LENGTH: 21
<212> TYPE: RNA
<213> ORGANISM: Artificial sequence
<220> FEATURE:
<223> OTHER INFORMATION: siRNA sequence 8 homo sapiens vitamin K
      epoxide reductase complex subunit 1 (Hs_VKORC1)

<400> SEQUENCE: 42
uucuaggaca agaagcacga g                                         21

<210> SEQ ID NO 43
<211> LENGTH: 57
<212> TYPE: DNA
<213> ORGANISM: Artificial sequence
<220> FEATURE:
<223> OTHER INFORMATION: Downstream primer 7 for homo sapiens vitamin
      K epoxide reductase complex subunit 1 (Hs_VKORC1) siRNA sequence

<400> SEQUENCE: 43
caaaaactgt aaaagatcc tgttcttcgt gctcggtgtt tcgtcctttc cacaaga      57

<210> SEQ ID NO 44
<211> LENGTH: 57
<212> TYPE: DNA
<213> ORGANISM: Artificial sequence
<220> FEATURE:
<223> OTHER INFORMATION: Downstream primer 8 for homo sapiens vitamin
      K epoxide reductase complex subunit 1 (Hs_VKORC1) siRNA sequence

<400> SEQUENCE: 44
caaaaactgt aaaagagca cgaagaacag gatcggtgtt tcgtcctttc cacaaga      57

```
<210> SEQ ID NO 45
<211> LENGTH: 21
<212> TYPE: RNA
<213> ORGANISM: Artificial sequence
<220> FEATURE:
<223> OTHER INFORMATION: siRNA sequence 9 homo sapiens vitamin K
      epoxide reductase complex subunit 1 (Hs_VKORC1)

<400> SEQUENCE: 45
gcauuguuug uaucaccacu u                                            21

<210> SEQ ID NO 46
<211> LENGTH: 21
<212> TYPE: RNA
<213> ORGANISM: Artificial sequence
<220> FEATURE:
<223> OTHER INFORMATION: siRNA sequence 10 homo sapiens vitamin K
      epoxide reductase complex subunit 1 (Hs_VKORC1)

<400> SEQUENCE: 46
uucguaacaa acauaguggu g                                            21

<210> SEQ ID NO 47
<211> LENGTH: 57
<212> TYPE: DNA
<213> ORGANISM: Artificial sequence
<220> FEATURE:
<223> OTHER INFORMATION: Downstream primer 9 for homo sapiens vitamin
      K epoxide reductase complex subunit 1 (Hs_VKORC1) siRNA sequence

<400> SEQUENCE: 47
caaaaactgt aaaaagcatt gtttgtatca ccacggtgtt tcgtcctttc cacaaga     57

<210> SEQ ID NO 48
<211> LENGTH: 57
<212> TYPE: DNA
<213> ORGANISM: Artificial sequence
<220> FEATURE:
<223> OTHER INFORMATION: Downstream primer 10 for homo sapiens vitamin
      K epoxide reductase complex subunit 1 (Hs_VKORC1) siRNA sequence

<400> SEQUENCE: 48
caaaaactgt aaaaagtggt gatacaaaca atgcggtgtt tcgtcctttc cacaaga     57

<210> SEQ ID NO 49
<211> LENGTH: 21
<212> TYPE: RNA
<213> ORGANISM: Artificial sequence
<220> FEATURE:
<223> OTHER INFORMATION: siRNA sequence 11 homo sapiens vitamin K
      epoxide reductase complex subunit 1 (Hs_VKORC1)

<400> SEQUENCE: 49
gcucaguuuc cggaaggucu u                                            21

<210> SEQ ID NO 50
<211> LENGTH: 21
<212> TYPE: RNA
<213> ORGANISM: Artificial sequence
<220> FEATURE:
<223> OTHER INFORMATION: siRNA sequence 12 homo sapiens vitamin K
      epoxide reductase complex subunit 1 (Hs_VKORC1)

<400> SEQUENCE: 50
uucgagucaa aggccuucca g                                            21
```

```
<210> SEQ ID NO 51
<211> LENGTH: 57
<212> TYPE: DNA
<213> ORGANISM: Artificial sequence
<220> FEATURE:
<223> OTHER INFORMATION: Downstream primer 11 for homo sapiens vitamin
      K epoxide reductase complex subunit 1 (Hs_VKORC1) siRNA
      sequence

<400> SEQUENCE: 51
caaaaactgt aaaaagctca gtttccggaa ggtcggtgtt tcgtcctttc cacaaga       57

<210> SEQ ID NO 52
<211> LENGTH: 57
<212> TYPE: DNA
<213> ORGANISM: Artificial sequence
<220> FEATURE:
<223> OTHER INFORMATION: Downstream primer 12 for homo sapiens vitamin
      K epoxide reductase complex subunit 1 (Hs_VKORC1) siRNA
      sequence

<400> SEQUENCE: 52
caaaaactgt aaaagacct tccggaaact gagcggtgtt tcgtcctttc cacaaga        57

<210> SEQ ID NO 53
<211> LENGTH: 37
<212> TYPE: DNA
<213> ORGANISM: Artificial sequence
<220> FEATURE:
<223> OTHER INFORMATION: PCR primer for amplification of the complete
      coding sequence of homo sapiens vitamin K epoxide reductase
      complex subunit 1 (VKORC1-HindIII-F)

<400> SEQUENCE: 53
attaagcttc accatgggca gcacctgggg gagccct                             37

<210> SEQ ID NO 54
<211> LENGTH: 31
<212> TYPE: DNA
<213> ORGANISM: Artificial sequence
<220> FEATURE:
<223> OTHER INFORMATION: PCR primer for amplification of the complete
      coding sequence of homo sapiens vitamin K epoxide reductase
      complex subunit 1 (VKORC1-EcoRI-R)

<400> SEQUENCE: 54
attgaattcc gtgcctctta gccttgccct g                                   31

<210> SEQ ID NO 55
<211> LENGTH: 18
<212> TYPE: DNA
<213> ORGANISM: Artificial sequence
<220> FEATURE:
<223> OTHER INFORMATION: PCR primer for Hs_VKORC1-Ex1-F

<400> SEQUENCE: 55
caatcgccga gtcagagg                                                  18

<210> SEQ ID NO 56
<211> LENGTH: 20
<212> TYPE: DNA
<213> ORGANISM: Artificial sequence
<220> FEATURE:
<223> OTHER INFORMATION: PCR primer for Hs_VKORC1-Ex1-R

<400> SEQUENCE: 56
taatcatctg gcatcctggc                                                20
```

-continued

```
<210> SEQ ID NO 57
<211> LENGTH: 19
<212> TYPE: DNA
<213> ORGANISM: Artificial sequence
<220> FEATURE:
<223> OTHER INFORMATION: PCR primer for Hs_VKORC1-Ex2-F

<400> SEQUENCE: 57
caaggcactg ggttgacag                                                  19

<210> SEQ ID NO 58
<211> LENGTH: 18
<212> TYPE: DNA
<213> ORGANISM: Artificial sequence
<220> FEATURE:
<223> OTHER INFORMATION: PCR primer for Hs_VKORC1-Ex2-R

<400> SEQUENCE: 58
gagtggggct gagctgac                                                   18

<210> SEQ ID NO 59
<211> LENGTH: 20
<212> TYPE: DNA
<213> ORGANISM: Artificial sequence
<220> FEATURE:
<223> OTHER INFORMATION: PCR primer for Hs_VKORC1-Ex3-F

<400> SEQUENCE: 59
gacatcatgg agtgttcggg                                                 20

<210> SEQ ID NO 60
<211> LENGTH: 20
<212> TYPE: DNA
<213> ORGANISM: Artificial sequence
<220> FEATURE:
<223> OTHER INFORMATION: PCR primer for Hs_VKORC1-Ex3-R

<400> SEQUENCE: 60
cttaggcaag gctcacatgc                                                 20

<210> SEQ ID NO 61
<211> LENGTH: 18
<212> TYPE: DNA
<213> ORGANISM: Artificial sequence
<220> FEATURE:
<223> OTHER INFORMATION: PCR primer for Hs_VKORC1-cDNA-F

<400> SEQUENCE: 61
ggcacgaggg ttttctcc                                                   18

<210> SEQ ID NO 62
<211> LENGTH: 19
<212> TYPE: DNA
<213> ORGANISM: Artificial sequence
<220> FEATURE:
<223> OTHER INFORMATION: PCR primer for Hs_VKORC1-cDNA-R

<400> SEQUENCE: 62
ctcacatgcc aaagcaaag                                                  19

<210> SEQ ID NO 63
<211> LENGTH: 18
<212> TYPE: DNA
<213> ORGANISM: Artificial sequence
<220> FEATURE:
<223> OTHER INFORMATION: PCR primer for Rn_VKORC1-cDNA-F

<400> SEQUENCE: 63
```
ggcgggttct tccctctt                    18

<210> SEQ ID NO 64
<211> LENGTH: 20
<212> TYPE: DNA
<213> ORGANISM: Artificial sequence
<220> FEATURE:
<223> OTHER INFORMATION: PCR primer for Rn_VKORC1-cDNA-R

<400> SEQUENCE: 64
catgtgctaa ggcaaagcaa                   20

<210> SEQ ID NO 65
<211> LENGTH: 21
<212> TYPE: DNA
<213> ORGANISM: Artificial sequence
<220> FEATURE:
<223> OTHER INFORMATION: PCR primer for Rn_VKORC1-cDNA-F-nes

<400> SEQUENCE: 65
ttgtgtctgc gctgtactgt c                 21

<210> SEQ ID NO 66
<211> LENGTH: 18
<212> TYPE: DNA
<213> ORGANISM: Artificial sequence
<220> FEATURE:
<223> OTHER INFORMATION: PCR primer for Rn_VKORC1-cDNA-R-nes

<400> SEQUENCE: 66
gtcagcctgg catgaggt                     18

<210> SEQ ID NO 67
<211> LENGTH: 22
<212> TYPE: DNA
<213> ORGANISM: Artificial sequence
<220> FEATURE:
<223> OTHER INFORMATION: PCR primer for Fr_VKORC1-cDNA-F

<400> SEQUENCE: 67
tcttttccat ttgattggtc ct                22

<210> SEQ ID NO 68
<211> LENGTH: 21
<212> TYPE: DNA
<213> ORGANISM: Artificial sequence
<220> FEATURE:
<223> OTHER INFORMATION: PCR primer for Fr_VKORC1-cDNA-R

<400> SEQUENCE: 68
tcagtttagt cgcacctcct g                 21

<210> SEQ ID NO 69
<211> LENGTH: 20
<212> TYPE: DNA
<213> ORGANISM: Artificial sequence
<220> FEATURE:
<223> OTHER INFORMATION: PCR primer for Fr_VKORC1-cDNA-F-nes

<400> SEQUENCE: 69
gtggccatct gagcagaaac                   20

<210> SEQ ID NO 70
<211> LENGTH: 20
<212> TYPE: DNA
<213> ORGANISM: Artificial sequence

```
<220> FEATURE:
<223> OTHER INFORMATION: PCR primer for Fr_VKORC1-cDNA-R-nes

<400> SEQUENCE: 70
tgctggattt cagtgggaac                                              20

<210> SEQ ID NO 71
<211> LENGTH: 18
<212> TYPE: DNA
<213> ORGANISM: Artificial sequence
<220> FEATURE:
<223> OTHER INFORMATION: PCR primer for Hs_VKORC1L1-cDNA-F

<400> SEQUENCE: 71
tgggtcgggc cccgacgg                                                18

<210> SEQ ID NO 72
<211> LENGTH: 22
<212> TYPE: DNA
<213> ORGANISM: Artificial sequence
<220> FEATURE:
<223> OTHER INFORMATION: PCR primer for Hs_VKORC1L1-cDNA-R

<400> SEQUENCE: 72
tttaaatcca tcggctaaaa ac                                           22

<210> SEQ ID NO 73
<211> LENGTH: 16
<212> TYPE: DNA
<213> ORGANISM: Artificial sequence
<220> FEATURE:
<223> OTHER INFORMATION: PCR primer for Hs_VKORC1L1-cDNA-F-nes

<400> SEQUENCE: 73
ggcggctgag gtggag                                                  16

<210> SEQ ID NO 74
<211> LENGTH: 21
<212> TYPE: DNA
<213> ORGANISM: Artificial sequence
<220> FEATURE:
<223> OTHER INFORMATION: PCR primer for Hs_VKORC1L1-cDNA-R-nes

<400> SEQUENCE: 74
agcaatggtt gctcacttta c                                            21

<210> SEQ ID NO 75
<211> LENGTH: 20
<212> TYPE: DNA
<213> ORGANISM: Artificial sequence
<220> FEATURE:
<223> OTHER INFORMATION: PCR primer for Fr_VKORC1L1-cDNA-F

<400> SEQUENCE: 75
cgagctccct gcgtatgtat                                              20

<210> SEQ ID NO 76
<211> LENGTH: 26
<212> TYPE: DNA
<213> ORGANISM: Artificial sequence
<220> FEATURE:
<223> OTHER INFORMATION: PCR primer for Fr_VKORC1L1-cDNA-R

<400> SEQUENCE: 76
gacgttgttg tttgtttatt tgattt                                       26
```

```
<210> SEQ ID NO 77
<211> LENGTH: 21
<212> TYPE: DNA
<213> ORGANISM: Artificial sequence
<220> FEATURE:
<223> OTHER INFORMATION: PCR primer for Fr_VKORC1L1-cDNA-F-nes

<400> SEQUENCE: 77
cgtatgtatg cgtgtctcca g                                          21

<210> SEQ ID NO 78
<211> LENGTH: 18
<212> TYPE: DNA
<213> ORGANISM: Artificial sequence
<220> FEATURE:
<223> OTHER INFORMATION: PCR primer for Fr_VKORC1L1-cDNA-Rnes

<400> SEQUENCE: 78
ttttcaccgc cgttctga                                              18

<210> SEQ ID NO 79
<211> LENGTH: 18
<212> TYPE: DNA
<213> ORGANISM: Artificial sequence
<220> FEATURE:
<223> OTHER INFORMATION: PCR primer for PCR primer for Rn_VKORC1L1-
      cDNA-F

<400> SEQUENCE: 79
ggcggcgtct gagtggag                                              18

<210> SEQ ID NO 80
<211> LENGTH: 20
<212> TYPE: DNA
<213> ORGANISM: Artificial sequence
<220> FEATURE:
<223> OTHER INFORMATION: PCR primer for Rn_VKORC1L1-cDNA-R

<400> SEQUENCE: 80
acaggtttaa atccatcggc                                            20

<210> SEQ ID NO 81
<211> LENGTH: 17
<212> TYPE: DNA
<213> ORGANISM: Artificial sequence
<220> FEATURE:
<223> OTHER INFORMATION: PCR primer for Rn_VKORC1L1-cDNA-F-nes

<400> SEQUENCE: 81
ctgagtggag gcggagg                                               17

<210> SEQ ID NO 82
<211> LENGTH: 24
<212> TYPE: DNA
<213> ORGANISM: Artificial sequence
<220> FEATURE:
<223> OTHER INFORMATION: PCR primer for Rn_VKORC1L1-cDNA-R-nes

<400> SEQUENCE: 82
tttcatgttc atgatcacat tttg                                       24

<210> SEQ ID NO 83
<211> LENGTH: 20
<212> TYPE: DNA
<213> ORGANISM: Artificial sequence
<220> FEATURE:
<223> OTHER INFORMATION: PCR primer for Rn_VKORC1L1-cDNA-R-short
```

```
<400> SEQUENCE: 83
ctggctgtca tgccaagtaa                                                20

<210> SEQ ID NO 84
<211> LENGTH: 18
<212> TYPE: DNA
<213> ORGANISM: Artificial sequence
<220> FEATURE:
<223> OTHER INFORMATION: PCR primer for Mm_VKORC1L1-cDNA-F

<400> SEQUENCE: 84
ggaagatggc ggcgcccg                                                  18

<210> SEQ ID NO 85
<211> LENGTH: 20
<212> TYPE: DNA
<213> ORGANISM: Artificial sequence
<220> FEATURE:
<223> OTHER INFORMATION: PCR primer for Mm_VKORC1L1-cDNA-R

<400> SEQUENCE: 85
tctgctgtca acactgcacc                                                20

<210> SEQ ID NO 86
<211> LENGTH: 17
<212> TYPE: DNA
<213> ORGANISM: Artificial sequence
<220> FEATURE:
<223> OTHER INFORMATION: PCR primer for Mm_VKORC1L1-cDNA-F-nes

<400> SEQUENCE: 86
ggtatgcagt gtgcgcc                                                   17

<210> SEQ ID NO 87
<211> LENGTH: 20
<212> TYPE: DNA
<213> ORGANISM: Artificial sequence
<220> FEATURE:
<223> OTHER INFORMATION: PCR primer for Mm_VKORC1L1-cDNA-R-nes

<400> SEQUENCE: 87
gcatttccca agatgttctg                                                20

<210> SEQ ID NO 88
<211> LENGTH: 28
<212> TYPE: DNA
<213> ORGANISM: Artificial Sequence
<220> FEATURE:
<223> OTHER INFORMATION: rVKORC1-outerF PCR-primer

<400> SEQUENCE: 88
atcctgagtt ccctggtgtc tgtcgctg                                       28

<210> SEQ ID NO 89
<211> LENGTH: 28
<212> TYPE: DNA
<213> ORGANISM: Artificial sequence
<220> FEATURE:
<223> OTHER INFORMATION: rVKORC1-outerR PCR-primer

<400> SEQUENCE: 89
tcagggcttt ttgaccttgt gttctggc                                       28

<210> SEQ ID NO 90
<211> LENGTH: 30
<212> TYPE: DNA
```

<213> ORGANISM: Artificial Sequence
<220> FEATURE:
<223> OTHER INFORMATION: rVKORC1-innerF PCR-primer

<400> SEQUENCE: 90
tgatttctgc attgtttgca tcaccacatg 30

<210> SEQ ID NO 91
<211> LENGTH: 26
<212> TYPE: DNA
<213> ORGANISM: Artificial sequence
<220> FEATURE:
<223> OTHER INFORMATION: rVKORC1-innerR PCR-primer

<400> SEQUENCE: 91
caacatcagg cccgcattga tggaat 26

<210> SEQ ID NO 92
<211> LENGTH: 25
<212> TYPE: DNA
<213> ORGANISM: artificial sequence
<220> FEATURE:
<223> OTHER INFORMATION: VKORC1-pcdna3-F PCR-primer

<400> SEQUENCE: 92
gggcggaagc ttgagataat gggca 25

<210> SEQ ID NO 93
<211> LENGTH: 22
<212> TYPE: DNA
<213> ORGANISM: Artificial sequence
<220> FEATURE:
<223> OTHER INFORMATION: VKORC1-pcdna3-R PCR-primer

<400> SEQUENCE: 93
gcttgaattc agggctcagt gc 22

<210> SEQ ID NO 94
<211> LENGTH: 492
<212> TYPE: DNA
<213> ORGANISM: Artificial sequence
<220> FEATURE:
<223> OTHER INFORMATION: Homo sapiens VKORC1 with rat warfarin
resistance mutation 416A>G

<400> SEQUENCE: 94
atgggcagca cctgggggag ccctggctgg gtgcggctcg ctctttgcct gacgggctta 60
gtgctctcgc tctacgcgct gcacgtgaag gcggcgcgcg cccgggaccg ggattaccgc 120
gcgctctgcg acgtgggcac cgccatcagc tgttcgcgcg tcttctcctc caggtggggc 180
aggggtttcg ggctggtgga gcatgtgctg ggacaggaca gcatcctcaa tcaatccaac 240
agcatattcg gttgcatctt ctacacacta cagctattgt taggttgcct gcggacacgc 300
tgggcctctg tcctgatgct gctgagctcc ctggtgtctc tcgctggttc tgtctacctg 360
gcctggatcc tgttcttcgt gctctatgat ttctgcattg tttgtatcac cacctgtgct 420
atcaacgtga gcctgatgtg gctcagtttc cggaaggtcc aagaacccca gggcaaggct 480
aagaggcact ga 492